US012569259B2

(12) United States Patent
Chandanson et al.

(10) Patent No.: US 12,569,259 B2
(45) Date of Patent: *Mar. 10, 2026

(54) UNIVERSAL ADAPTER FOR HANDHELD SURGICAL SYSTEMS

(71) Applicant: SpineGuard, Vincennes (FR)

(72) Inventors: Thibault Chandanson, Vincennes (FR); Stephane Bette, Vincennes (FR); Francois Teyssere, Vincennes (FR); Maurice Bourlion, Rive de Gier (FR)

(73) Assignee: SpineGuard, Vincennes (FR)

( * ) Notice: Subject to any disclaimer, the term of this patent is extended or adjusted under 35 U.S.C. 154(b) by 159 days.

This patent is subject to a terminal disclaimer.

(21) Appl. No.: 18/622,512

(22) Filed: Mar. 29, 2024

(65) Prior Publication Data

US 2024/0237994 A1    Jul. 18, 2024

Related U.S. Application Data

(63) Continuation-in-part of application No. 17/935,853, filed on Sep. 27, 2022.

(Continued)

(51) Int. Cl.
*A61B 17/16* (2006.01)

(52) U.S. Cl.
CPC ........ *A61B 17/1617* (2013.01); *A61B 17/162* (2013.01)

(58) Field of Classification Search
CPC . A61B 17/16; A61B 17/1613; A61B 17/1615; A61B 17/1617; A61B 17/162;

(Continued)

(56) References Cited

U.S. PATENT DOCUMENTS

| | | | |
|---|---|---|---|
| 6,470,207 B1 | 10/2002 | Simon et al. | |
| 6,635,062 B2 | 10/2003 | Ray, III et al. | |

(Continued)

FOREIGN PATENT DOCUMENTS

| | | | | |
|---|---|---|---|---|
| CN | 103948412 A | | 7/2014 | |
| CN | 107921554 A | * | 4/2018 | ......... A61B 17/1626 |

(Continued)

OTHER PUBLICATIONS

U.S. Appl. No. 15/115,988, filed Feb. 3, 2015.

(Continued)

*Primary Examiner* — Eric S Gibson
(74) *Attorney, Agent, or Firm* — Greenberg Traurig, LLP; Christopher C. Bolten; Albert K. Heng

(57) ABSTRACT

Adapters for surgical drilling systems, and methods of use, are provided for performing surgical procedures, such as surgical drilling into bony structures, while guided by a conductivity sensing system. The adapters may be configured to be coupled to a surgical drilling tool such as a conventional surgical drill and a drill bit having conductivity sensing capabilities, e.g., via a sensing drill bit, or a surgical hand tool having conductivity sensing capabilities. The adapters further include a controller configured to receive one or more signal indicative of measured electrical conductivity and/or penetration depth measurement, detect a condition associated with a change of measured electrical conductivity based on the signal, and arrest advancement of the surgical drilling tool responsive to detection of the condition.

29 Claims, 28 Drawing Sheets

Related U.S. Application Data

(60) Provisional application No. 63/455,531, filed on Mar. 29, 2023, provisional application No. 63/249,451, filed on Sep. 28, 2021.

(58) Field of Classification Search
CPC ............ A61B 17/1622; A61B 17/1624; A61B 17/1626; A61B 17/1628; A61B 17/1633; A61B 17/1655; A61B 17/1657; A61B 17/1671; A61B 2017/00123; A61B 2090/034; A61B 2090/062; A61B 2090/064
See application file for complete search history.

(56) References Cited

U.S. PATENT DOCUMENTS

| | | | | |
|---|---|---|---|---|
| 6,796,985 | B2 | 9/2004 | Bolger et al. | |
| 7,580,743 | B2 * | 8/2009 | Bourlion | A61B 5/053 606/80 |
| 8,092,457 | B2 * | 1/2012 | Oettinger | A61B 17/1626 606/80 |
| 8,361,152 | B2 | 1/2013 | McCormack et al. | |
| 8,419,746 | B2 * | 4/2013 | Bourlion | A61B 17/1626 606/102 |
| 8,486,119 | B2 | 7/2013 | Bourlion | |
| 8,634,897 | B2 | 1/2014 | Simon et al. | |
| 8,795,285 | B2 | 8/2014 | Kwon | |
| 8,939,979 | B2 * | 1/2015 | Del Rio | A61B 17/1637 606/80 |
| 9,066,751 | B2 | 6/2015 | Sasso | |
| 9,204,830 | B2 | 12/2015 | Zand et al. | |
| 9,538,935 | B2 | 1/2017 | Bourlion et al. | |
| 9,855,060 | B2 * | 1/2018 | Ardel | A61B 17/162 |
| 9,901,283 | B2 | 2/2018 | Bourlion et al. | |
| 9,937,009 | B2 * | 4/2018 | Schroeder | F16D 9/10 |
| 10,064,630 | B2 * | 9/2018 | Forman | A61B 17/1626 |
| 10,092,300 | B2 * | 10/2018 | del Rio | A61B 17/1631 |
| 10,149,729 | B2 | 12/2018 | Smaby et al. | |
| 10,624,572 | B2 * | 4/2020 | Bourlion | A61B 17/1671 |
| 10,987,113 | B2 * | 4/2021 | McGinley | A61B 17/1626 |
| 11,000,292 | B2 * | 5/2021 | McGinley | A61B 17/1626 |
| 11,058,436 | B2 * | 7/2021 | McGinley | A61B 17/142 |
| 11,083,469 | B2 * | 8/2021 | del Rio | A61B 17/1617 |
| 11,344,372 | B2 * | 5/2022 | Bourlion | A61B 34/10 |
| 11,399,902 | B2 * | 8/2022 | Bourlion | B25J 9/1635 |
| 11,903,591 | B2 * | 2/2024 | Chen | A61B 90/39 |
| 12,213,683 | B2 * | 2/2025 | del Rio | A61B 17/162 |
| 2002/0120197 | A1 | 8/2002 | Kleffner et al. | |
| 2003/0078495 | A1 | 4/2003 | Goodwin | |
| 2005/0116673 | A1 * | 6/2005 | Carl | A61B 17/1626 318/432 |
| 2005/0119660 | A1 | 6/2005 | Bourlion et al. | |
| 2006/0241628 | A1 * | 10/2006 | Parak | A61B 17/1626 606/80 |
| 2007/0239187 | A1 | 10/2007 | Brunnett et al. | |
| 2008/0262526 | A1 | 10/2008 | Neubardt et al. | |
| 2009/0157059 | A1 | 6/2009 | Allen et al. | |
| 2010/0024981 | A1 | 2/2010 | Wallace et al. | |
| 2010/0286694 | A1 * | 11/2010 | Rio | A61B 17/1631 606/80 |
| 2011/0015649 | A1 | 1/2011 | Anvari et al. | |
| 2012/0046668 | A1 | 2/2012 | Gantes | |
| 2012/0296213 | A1 | 11/2012 | Mauldin, Jr. et al. | |
| 2013/0085413 | A1 | 4/2013 | Tsamir et al. | |
| 2013/0085505 | A1 | 4/2013 | Markey et al. | |
| 2013/0152746 | A1 * | 6/2013 | Kerboul | B25B 23/1427 81/475 |
| 2013/0296734 | A1 | 11/2013 | Bourlion et al. | |
| 2014/0094808 | A1 | 4/2014 | Herndon | |
| 2014/0276002 | A1 | 9/2014 | West et al. | |
| 2014/0276950 | A1 | 9/2014 | Smaby et al. | |
| 2014/0324044 | A1 | 10/2014 | Haufe et al. | |
| 2015/0066030 | A1 * | 3/2015 | McGinley | A61B 90/30 606/79 |
| 2015/0148176 | A1 * | 5/2015 | Schroeder | A61B 17/1622 464/33 |
| 2015/0196306 | A1 * | 7/2015 | del Rio | A61B 17/1617 606/80 |
| 2015/0366624 | A1 | 12/2015 | Kostrzewski et al. | |
| 2016/0074123 | A1 | 3/2016 | Bly et al. | |
| 2016/0302871 | A1 | 10/2016 | Gregerson et al. | |
| 2016/0361069 | A1 * | 12/2016 | Ardel | A61B 17/1626 |
| 2017/0007199 | A1 | 1/2017 | Bourlion et al. | |
| 2017/0056116 | A1 | 3/2017 | Kostrzewski | |
| 2017/0100822 | A1 * | 4/2017 | Cutler | F16D 7/044 |
| 2017/0360493 | A1 | 12/2017 | Zucker et al. | |
| 2018/0042514 | A1 | 2/2018 | Verard et al. | |
| 2018/0098714 | A1 * | 4/2018 | Bourlion | A61B 17/1671 |
| 2018/0177556 | A1 | 6/2018 | Noonan | |
| 2019/0175886 | A1 | 6/2019 | Abdelwahed et al. | |
| 2019/0201011 | A1 * | 7/2019 | del Rio | A61B 17/1631 |
| 2019/0388173 | A1 | 12/2019 | Pak et al. | |
| 2020/0324408 | A1 * | 10/2020 | Bourlion | A61B 34/76 |
| 2020/0337782 | A1 * | 10/2020 | Glassman | A61B 34/32 |
| 2021/0068905 | A1 | 3/2021 | Quaid et al. | |
| 2021/0282862 | A1 * | 9/2021 | Bourlion | A61B 34/10 |
| 2021/0298795 | A1 * | 9/2021 | Bowling | B25J 9/1689 |
| 2022/0022891 | A1 * | 1/2022 | del Rio | A61B 17/1679 |
| 2022/0104901 | A1 | 4/2022 | Lawrie | |
| 2022/0168048 | A1 | 6/2022 | Shoham et al. | |
| 2022/0175455 | A1 | 6/2022 | Ungi et al. | |
| 2022/0175462 | A1 | 6/2022 | Turgeman et al. | |
| 2022/0218421 | A1 * | 7/2022 | Junio | A61B 17/1626 |
| 2022/0233250 | A1 * | 7/2022 | Bette | A61B 5/0538 |
| 2022/0361896 | A1 * | 11/2022 | Bette | A61B 17/164 |
| 2022/0361897 | A1 * | 11/2022 | Chen | A61B 17/1631 |
| 2023/0088846 | A1 * | 3/2023 | Laing | A61B 17/1628 606/80 |
| 2023/0095197 | A1 * | 3/2023 | Chandanson | A61B 17/162 606/80 |
| 2024/0237994 | A1 * | 7/2024 | Chandanson | A61B 17/1626 |

FOREIGN PATENT DOCUMENTS

| | | | | |
|---|---|---|---|---|
| CN | 110882037 | A | | 3/2020 |
| CN | 118251181 | A * | 6/2024 | ........... A61B 17/162 |
| EP | 1474046 | A1 | | 11/2004 |
| EP | 3319539 | A1 | | 5/2018 |
| EP | 3525696 | A1 | | 8/2019 |
| EP | 3761870 | A1 | | 1/2021 |
| EP | 3883491 | A1 | | 9/2021 |
| FR | 2795624 | A1 | | 1/2001 |
| FR | 3034643 | A1 | | 10/2016 |
| JP | 2005525150 | A | | 8/2005 |
| JP | 2016518878 | A | | 6/2016 |
| WO | WO-03068076 | A1 | | 8/2003 |
| WO | WO-2014146090 | A1 | | 9/2014 |
| WO | WO-2015006296 | A1 | | 1/2015 |
| WO | WO-2016043676 | A1 | | 3/2016 |
| WO | WO-2016162634 | A1 | | 10/2016 |
| WO | WO-2016199152 | A1 * | 12/2016 | ........... A61B 17/162 |
| WO | WO-2019002578 | A1 | | 1/2019 |
| WO | WO-2019110119 | A1 * | 6/2019 | ........ A61B 17/1673 |
| WO | WO-2020000038 | A1 | | 1/2020 |
| WO | WO-2020097481 | A1 | | 5/2020 |
| WO | WO-2021046247 | A1 | | 3/2021 |
| WO | WO-2021111439 | A1 * | 6/2021 | ........ A61B 17/1622 |
| WO | WO-2021178706 | A1 * | 9/2021 | ............ A61B 90/08 |
| WO | WO-2022170185 | A1 | | 8/2022 |

OTHER PUBLICATIONS

U.S. Appl. No. 16/757,937 / U.S. Pat. No. 11,399,902, filed Apr. 21, 2020 / Aug. 2, 2022.

U.S. Appl. No. 17/334,566 / U.S. Pat. No. 11,344,372, filed May 28, 2021 / May 31, 2022.

U.S. Appl. No. 17/659,167, filed Apr. 13, 2022.

U.S. Appl. No. 17/661,719, filed May 2, 2022.

U.S. Appl. No. 17/781,578, filed Jun. 1, 2022.

U.S. Appl. No. 17/935,853, filed Sep. 27, 2022.

U.S. Appl. No. 18/518,428, filed Nov. 22, 2023.

(56)     References Cited

OTHER PUBLICATIONS

International Search Report & Written Opinion dated Aug. 31, 2022 in Int'l PCT Patent Appl. Serial No. PCT/EP2022/061868 (0310).
International Search Report & Written Opinion dated Dec. 15, 2022 in Int'l PCT Patent Appl. No. PCT/IB2022/059201 (0410).
International Search Report & Written Opinion for PCT Application No. PCT/IL2020/051241, mailed Mar. 22, 2021, 13 pages.
International Search Report & Written Opinion for PCT Application No. PCT/IL2022/050585, mailed Nov. 3, 2022, 15 pages.
International Search Report for PCT Application No. PCT/FR2015/050241 mailed May 4, 2015, 08 Pages.
International Search Report & Written Opinion dated Jan. 7, 2019 in Int'l PCT Patent Appl. Serial No. PCT/FR2018/052640.

* cited by examiner

150

Controller

Processor(s) — 152

Communication Circuitry — 154

Power Supply — 156

User interface — 157

Memory — 158

Adapter Interface Module — 160

Electric Generator Interface Module — 162

Conductivity Sensing Module — 164

Depth Sensing Module — 166

Condition Detection Module — 168

Alert Generation Module — 170

Angle Sensing Module — 172

Display Interface Module — 174

Operating System — 176

450

Controller

Processor(s) — 452

Communication Circuitry — 454

Power Supply — 456

User interface — 457

Memory — 458

Electric Generator Interface Module — 460

Conductivity Sensing Module — 462

Depth Sensing Module — 464

Condition Detection Module — 466

Alert Generation Module — 468

Brake Mechanism Interface Module — 470

Angle Sensing Module — 472

Display Interface Module — 474

Operating System — 476

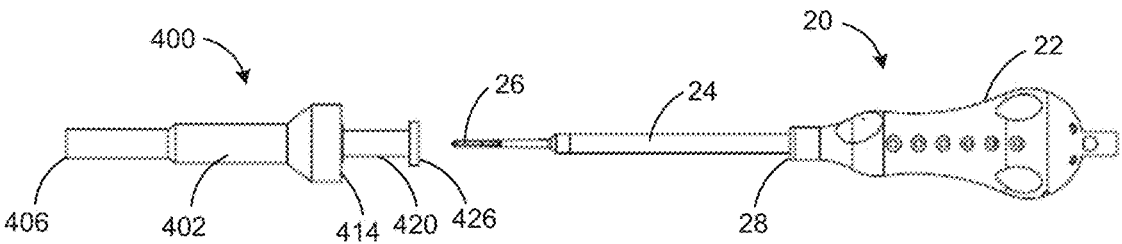
FIG. 11A
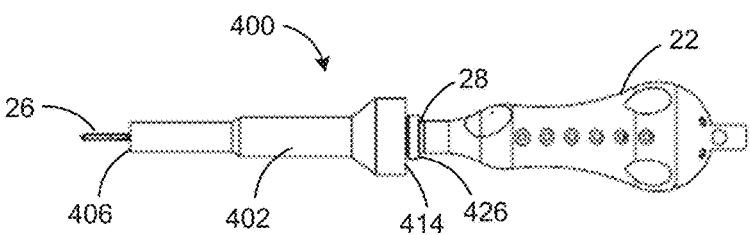
FIG. 11B
FIG. 11C
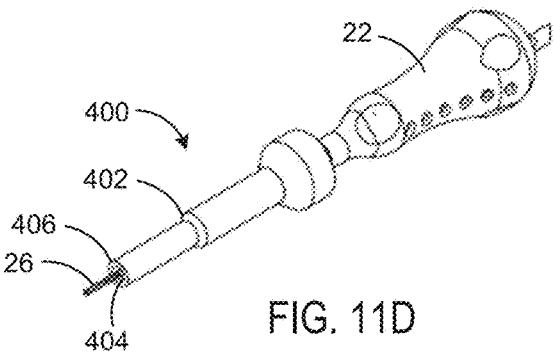
FIG. 11D

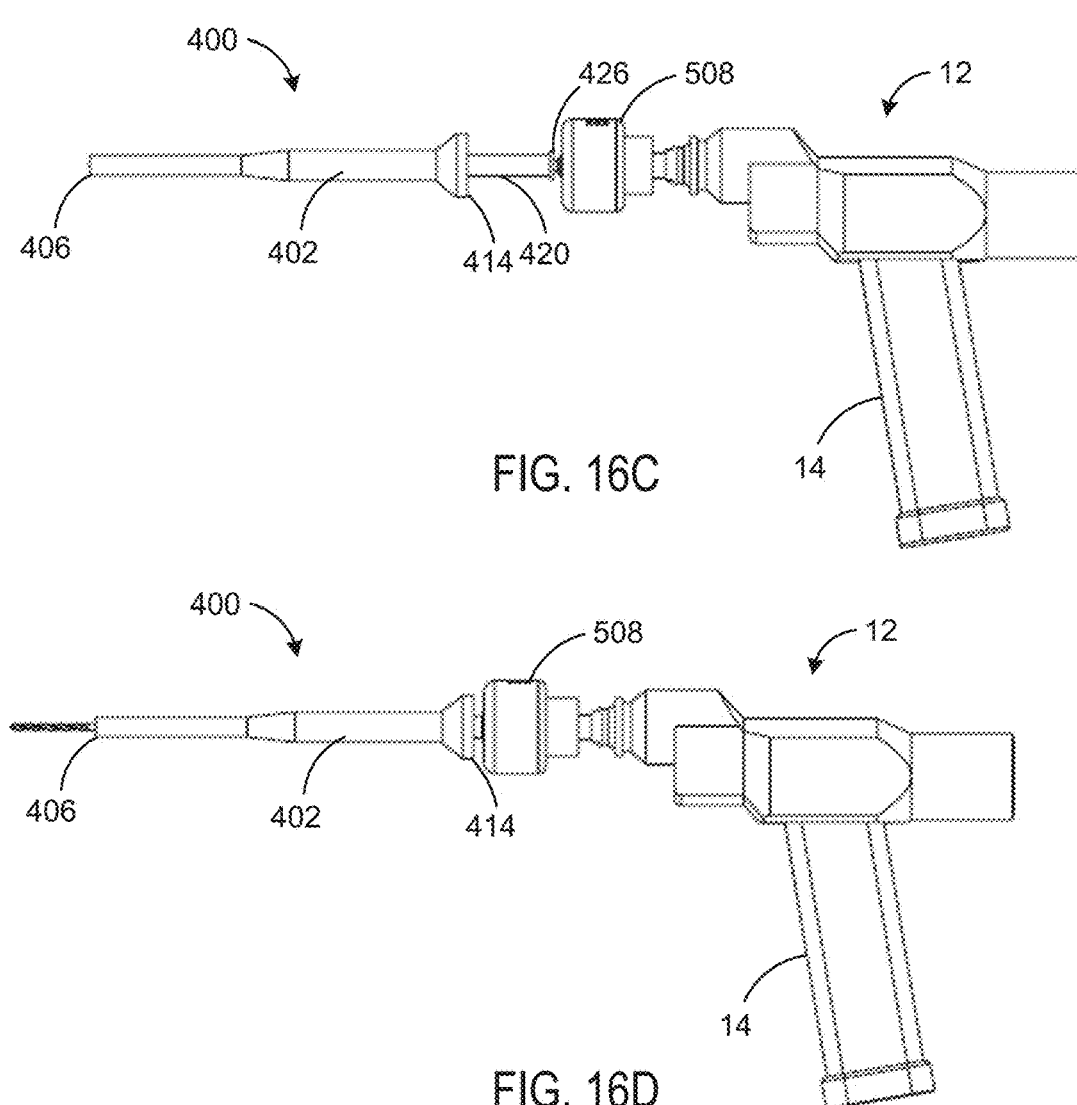
FIG. 16C
FIG. 16D
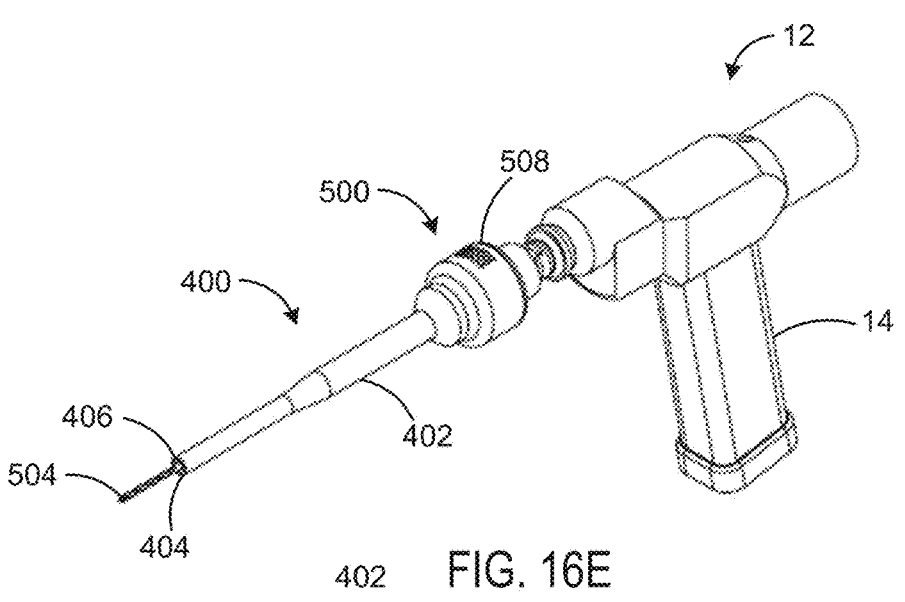
FIG. 16E

508

512a
512b
512c
512d

⊚○○○  Low conductivity

⊚⊚○○  Medium conductivity

⊚⊚⊚○  High conductivity

⊚⊚⊚⊚  Very high conductivity 512d
512c
512a
512b

⊚○○○  Low conductivity

⊚⊚○○  Medium conductivity

⊚⊚⊚○  High conductivity

⊚⊚⊚⊚  Very high conductivity

⊚○○○  Low conductivity

⊚○○○  Medium conductivity

⊚○⊚○  High conductivity

⊚○⊚⬤  Very high conductivity

⊚○○○  Low conductivity

⊚○○○  Medium conductivity

⊚○⊚○  High conductivity

⊚○⊚⬤  Very high conductivity

508

514a

514b

514c

514d

Low conductivity

Medium conductivity

High conductivity

Very high conductivity

514d

514c

514a

514b

Low conductivity

Medium conductivity

High conductivity

Very high conductivity

508

514a

514b

514c

514d

| | Low conductivity |
| | Medium conductivity |
| | High conductivity |
| | Very high conductivity |

514d
514c

| | Low conductivity |
| | Medium conductivity |
| | High conductivity |
| | Very high conductivity |

514a
514b

UNIVERSAL ADAPTER FOR HANDHELD SURGICAL SYSTEMS

CROSS-REFERENCE TO RELATED APPLICATION

This application claims priority to U.S. Provisional Patent Appl. No. 63/455,531, filed Mar. 29, 2023, and is a continuation-in-part application of U.S. patent application Ser. No. 17/935,853, filed Sep. 27, 2022, which claims priority to U.S. Provisional Patent Appl. No. 63/249,451, filed Sep. 28, 2021, the entire contents of each of which are incorporated herein by reference.

FIELD OF USE

A universal adapter is provided for use with surgical instruments for performing surgical procedures guided by a feedback-based sensing system.

BACKGROUND

Image-based surgical techniques have been used to aid physicians in performing a wide variety of delicate surgical procedures. These surgical procedures are used, for example, when patient anatomy obscures visualization of a surgical tool, or when a working end of a surgical tool is difficult to visualize in three dimensions. Surgical procedures in which such concerns frequently arise include, for example, spinal implant placement, alignment of broken bone fragments, and fixation of bone fractures.

Surgical navigation systems are known that use x-ray or fluoroscopic images to assist a physician in visualizing the location of a working end of a surgical tool within patient anatomy. Such systems repeatedly acquire x-ray or CT images during a surgical procedure, thereby permitting near real-time display of a position of the working end of the surgical tool relative to the patient anatomy. Fluoroscopically-based surgical navigation systems also may track a trajectory of the surgical tool and superimpose a representation of the surgical tool onto pre-acquired images of the patient anatomy, without x-rays being taken repeatedly during the surgical procedure. An example of such a system is the Stealth Station® navigation system sold by Medtronic, Inc., which provides a surgeon with CT-imaging feedback of the position and trajectory of instruments.

Adoption of previously known surgical navigation systems has been limited because the accuracy of such systems may be compromised by a variety of factors. For example, a patient or the surgeon may reposition the patient's body on the surgical table, thereby causing mis-registration of the working end of the surgical tool relative to pre-acquired images. One solution to this problem, to periodically update the fluoroscopic or CT-images during the surgical procedure, disadvantageously subjects the patient and the surgeon to greater exposure to ionizing radiation.

Yet another inherent limitation of previously known navigation systems is the inability to provide a high degree of confidence of the location of the working end of a surgical tool in three-dimensions, based on two-dimensional displayed images. While navigation systems may provide multiple views of the patient's anatomy and the working end, it may be challenging for the surgeon to mentally integrate such views in real time to achieve a high degree of confidence about the location of the working end of the surgical tool, especially if there is a need to limit advancement of the surgical tool to avoid penetrating sensitive structure or tissues.

Accordingly, it would be desirable to provide systems and methods that improve upon known surgical navigation systems, and which enable a surgeon accurately to confirm the location of the working end of a surgical tool, and particularly, when the working end of the surgical tool is approaching a sensitive portion of the patient's anatomy.

It further would be desirable to provide systems and methods that not only alerts a surgeon when the working end is approaching a transition in the anatomy in near real-time, but automatically stops further advancement of the working end when the working end approaches an undesirable condition.

SUMMARY

Provided herein are systems and methods that overcome the drawbacks of previously-known systems. In accordance with one aspect of the invention, a system for use with a surgical drill is provided. The system may include a sensing drill bit comprising a proximal portion configured to be removably coupled to and receive rotary motion from the surgical drill, and an elongated drilling portion having a distal end configured to penetrate an anatomic portion, the elongated drilling portion configured to sense electrical conductivity. The system further may include an adapter having a lumen sized and shaped to receive the elongated drilling portion of the sensing drill bit. The adapter may comprise a brake mechanism configured to be actuated to arrest advancement of the elongated drilling portion relative to the adapter. In addition, the system may include a controller operatively coupled to the elongated drilling portion and the brake mechanism. The controller may be programmed to: receive a signal indicative of the electrical conductivity sensed by the elongated drilling portion as the elongated drilling portion penetrates the anatomic portion; and responsive to the signal, cause the brake mechanism to arrest advancement of the elongated drilling portion and the surgical drill relative to the adapter.

The sensing drill bit may comprise a hub configured to house electronic components electrically coupled to the elongated drilling portion. For example, the electronic components may be configured to generate and transmit the signal indicative of the electrical conductivity to the controller. Moreover, the hub may comprise one or more indicators configured to illuminate in one or more colors in a manner to indicate one or more predetermined ranges of electrical conductivity sensed by the elongated drilling portion. Accordingly, the controller may be configured to cause the one or more indicators to illuminate in the one or more colors based on the signal indicative of the electrical conductivity sensed by the elongated drilling portion. For example, the one or more indicators may be configured to illuminate in a plurality of colors, each color of the plurality of colors indicative of a predetermined range of electrical conductivity sensed by the elongated drilling portion. Accordingly, the controller may be configured to cause the one or more indicators to illuminate in a color of the plurality of colors based on the signal indicative of the electrical conductivity sensed by the elongated drilling portion. Alternatively, the one or more indicators may be configured to illuminate in a plurality of intensities, each intensity of the plurality of intensities indicative of a predetermined range of electrical conductivity sensed by the elongated drilling portion. Accordingly, the controller may be configured to cause the one or more indicators to illuminate in an intensity of the plurality of intensities based on the signal indicative of the electrical conductivity sensed by the elongated drilling portion.

In some embodiments, the one or more indicators may be configured to illuminate in a blinking manner. Accordingly, the controller may be configured to cause the one or more indicators to illuminate in the blinking manner with at least one of a pitch or cadence based on the signal indicative of the electrical conductivity sensed by the elongated drilling portion. Moreover, the one or more indicators may comprise one or more ring-shaped indicators. The elongated drilling portion may be configured to penetrate bone. In addition, the controller may be configured to sense changes in electrical conductivity caused by the elongated drilling portion transitioning from a first tissue or fluid type to a second tissue or fluid type. For example, the sensed electrical conductivity may change as the elongated drilling portion transition between, e.g., air, blood, cerebral spinal fluid, soft tissue, e.g., skin, and/or hard tissue, e.g., bone. Moreover, the elongated drilling portion may comprise at least two electrodes configured to sense electrical conductivity and to generate the signal indicative of the electrical conductivity sensed by the elongated drilling portion.

Additionally, the controller further may be configured to: detect a predetermined condition associated with a change of measured electrical conductivity based on the signal; and cause the brake mechanism to arrest advancement of the elongated drilling portion and responsive to detection of the predetermined condition. The controller may be configured to generate an alarm upon detection of the signal satisfying a predetermined condition. The adapter may comprise a stationary component comprising a spring, and a plunger coupled to the spring. The plunger may be configured to be slidably movable within the stationary component responsive to a force applied by the sensing drill bit. Further, the lumen may extend through the plunger and the stationary component, and the brake mechanism may be configured to lock the plunger relative to the stationary component to thereby arrest advancement of the elongated drilling portion relative to the adapter. A proximal end of the plunger may comprise an abutment portion configured to engage with a hub of the sensing drill bit, such that the sensing drill bit may apply the force to the plunger via the engagement between the abutment portion and the hub. Moreover, an outer surface of the plunger may comprise a first mating surface, and the braking mechanism may comprise a second mating surface configured to transition between an unlocked state where the second mating surface is disengaged from the plunger, and a locked state where the second mating surface releasably engages with the first mating surface of the plunger to thereby lock the plunger relative to the stationary component. For example, the first mating surface may comprise a plurality of grooves, holes, or teeth, and the second mating surface may be a fork, a pin, or a tooth.

The sensor further may include a sensor configured to measure an angle of the system relative to a surface of the anatomic portion in 3D space. Accordingly, the controller may be configured to: receive a signal indicative of the measured angle from the sensor; and cause a display operatively coupled to the controller to display information indicative of the measured angle. Additionally, the controller may be configured to cause the display to display a virtual representation of the measured angle overlaid on a virtual model of the anatomic portion in real time. The sensor may comprise at least one of a gravity angle sensor chip, an accelerometer, a compass, or gyroscope. The sensor may be disposed on at least one of the adapter, the sensing drill bit, or the surgical drill. The controller may be configured to, during a calibration phase, set a reference orientation of the system when the system is positioned vertically against the anatomic portion while a reference axis of the system points in a cephalic direction. In addition, the system may include a sensor configured to measure a penetration depth of the elongated drilling portion within the anatomic portion. Accordingly, the controller may be configured to: receive a signal indicative of the penetration depth of the elongated drilling portion from the sensor; and cause the brake mechanism to arrest advancement of the elongated drilling portion when changes in at least one of electrical conductivity, depth of penetration of the elongated drilling portion, or electrical conductivity as a function of depth of penetration satisfy one or more predetermined conditions. Moreover, the controller may be configured to cause a display operatively coupled to the controller to display information indicative of at least one of the electrical conductivity sensed by the elongated drilling portion or the penetration depth of the elongated drilling portion.

In addition, the sensing drill bit may comprise one or more indicators configured to illuminate in a plurality of colors, each color of the plurality of colors indicative of at least one of a predetermined range of electrical conductivity sensed by the elongated drilling portion or a predetermined range of penetration depth of the elongated drilling portion. Accordingly, the controller may be configured to cause the one or more indicators to illuminate in a color of the plurality of colors based on at least one of the signal indicative of the electrical conductivity sensed by the elongated drilling portion or the signal indicative of the penetration depth of the elongated drilling portion. The system further may include an external computing device operatively coupled to the adapter and the sensing drill bit via a wired or wireless connection. For example, the controller may be disposed within the external computing device.

In accordance with another aspect of the invention, a computer implemented system for operating an adapter for use with a sensing drill bit comprising an elongated drilling portion configured to receive rotary motion from a surgical drill is provided. The system may comprise at least one processor configured to: receive a signal indicative of the electrical conductivity sensed by the elongated drilling portion as the elongated drilling portion penetrates an anatomic portion through a lumen of a sleeve of the adapter via the surgical drill; detect a predetermined condition associated with a change of measured electrical conductivity based on the signal; and cause a brake mechanism of the adapter to arrest advancement of the elongated drilling portion and the surgical drill relative to the adapter responsive to detection of the predetermined condition. The at least one processor further may be configured to: detect a predetermined condition associated with a change of measured electrical conductivity based on the signal; and generate an alert when changes in electrical conductivity satisfy one or more predetermined conditions. In addition, the at least one processor may be configured to: receive, from one or more sensors, a signal indicative of an angle of the adapter relative to a surface of the anatomic portion in 3D space as the elongated drilling portion penetrates the anatomic portion; and cause a display operatively coupled to the at least one processor to display information indicative of the angle. For example, the at least one processor may be configured to cause the display to display a virtual representation of the angle overlaid on a virtual model of the anatomic portion in real time.

Moreover, the at least one processor may be configured to: receive, from one or more depth sensors, a signal indicative of a depth of penetration of the elongated drilling portion within the anatomic portion; and cause the brake mechanism to arrest advancement of the elongated drilling portion when changes in at least one of electrical conductivity, depth of penetration of the elongated drilling portion, or electrical conductivity as a function of depth of penetration satisfy one or more predetermined conditions. Additionally, the at least one processor may be configured to cause one or more indicators of the sensing drill bit to illuminate in a color of a plurality of colors or an intensity of a plurality of intensities based on the signal indicative of the electrical conductivity sensed by the elongated drilling portion, each color of the plurality of colors or each intensity of the plurality of intensities indicative of a predetermined range of electrical conductivity sensed by the elongated drilling portion. Moreover, the at least one processor may be configured to cause one or more indicators of the sensing drill bit to illuminate in a blinking manner with at least one of a pitch or cadence indicative of a predetermined range of electrical conductivity sensed by the elongated drilling portion. The at least one processor further may be configured to cause, responsive to detection of the predetermined condition, a first mating surface of the brake mechanism to transition from an unlocked state where the first mating surface is disengaged from a plunger of the adapter, to a locked state where the first mating surface releasably engages with a second mating surface disposed on an outer surface of the plunger to thereby lock the plunger relative to a stationary component of the adapter and arrest advancement of the elongated drilling portion and the surgical drill relative to the adapter. For example, the first mating surface may be a fork, a pin, or a tooth, and the second mating surface may comprise a plurality of grooves, holes, or teeth.

In accordance with another aspect of the invention, an adapter is provided for use in surgical drilling systems for preventing injury during a surgical procedure such as a procedure involving drilling of bone, e.g., the spine. For example, the adapter may be provided for use with a surgical tool comprising an elongated drilling portion. The adapter may include a sleeve having a lumen sized and shaped to receive the elongated drilling portion of the surgical tool therethrough, a brake mechanism configured to be actuated to arrest advancement of the elongated drilling portion relative to the sleeve, and a controller programmed to: receive a signal indicative of an electrical conductivity sensed by the elongated drilling portion, and responsive to the signal, cause the brake mechanism to arrest advancement of the elongated drilling portion relative to the sleeve.

The controller may further be programmed to receive a signal indicative of penetration depth of the elongated drilling portion, and cause the brake mechanism to arrest advancement of the elongated drilling portion when changes in at least one of electrical conductivity or depth of penetration of the elongated drilling portion satisfy one or more predetermined conditions. The elongated drilling portion may be configured to penetrate bone. Additionally, the controller may be programmed to sense changes in electrical conductivity caused by the elongated drilling portion transitioning from a first tissue or fluid type to a second tissue or fluid type. Moreover, the controller may be programmed to sense changes in electrical conductivity during penetration by the elongated drilling portion, such that the controller causes the brake mechanism to arrest advancement of the elongated drilling portion when the changes in electrical conductivity satisfy one or more predetermined conditions.

In some embodiments, an external computing device may be operatively coupled to the adapter, such that the controller may be disposed within the external computing device via a wired or wireless connection. The controller further may be programmed to generate an alarm upon detection of the signal satisfying a predetermined condition. In addition, the controller further may be programmed to monitor penetration of the elongated drilling portion into a bony structure based on the signal, detect a condition associated with a change of measured electrical conductivity, and cause the brake mechanism to arrest advancement of the elongated drilling portion responsive to detection of the condition.

The sleeve may include a stationary component comprising a spring, and the adapter may further include a plunger coupled to the spring, such that the plunger is configured to be slidably movable within the stationary component responsive to a force applied by the surgical tool. Accordingly, the lumen may extend through the plunger and the stationary component. Moreover, the brake mechanism may be configured to lock the plunger relative to the stationary component to thereby arrest advancement of the elongated drilling portion relative to the adapter. Additionally, a proximal end of the plunger may include an abutment portion configured to engage with a stopper of the surgical tool, such that the surgical tool applies the force to the plunger via the engagement between the abutment portion and the stopper. The stationary component may include a contact sensor, and the plunger may include a screw configured to engage with the contact sensor as the plunger moves relative to the stationary component, such that the controller is programmed to determine penetration depth of the elongated drilling portion based on electrical impedance responsive to engagement between the screw and the contact sensor. In some embodiments, the stationary component of the adapter may be configured to be coupled to a distal end of a robot arm programmed to determine at least one of an entry point or a trajectory of the surgical tool for a predetermined surgical procedure.

In accordance with some aspects of the present disclosure, the surgical tool may comprise a drill bit, and the sleeve may comprise a chuck configured to receive the drill bit. Accordingly, the adapter further may include a proximal end configured to be coupled to a surgical drill to selectively transmit rotary motion from the surgical drill to drill bit, such that the controller is programmed to, responsive to the signal, cease transmission of the rotary motion from the surgical drill to the drill bit to arrest advancement of the drill bit. The proximal end of the adapter may include a first rotor configured to be coupled to the surgical drill and a second rotor coupled to the chuck, wherein the first and second rotors are configured to engage each other to transmit rotary motion, and responsive to the signal, the controller decouples the second rotor from the first rotor to cease transmission of the rotary motion from the surgical drill to the drill bit. The brake mechanism may be configured to be actuated by the controller to lock the drill bit relative to the adapter to stop rotary motion of the drill bit following the decoupling of the second rotor from the first rotor. In some embodiments, the second rotor may be selectively coupled to the first rotor via mechanical force or electromagnetic force. For example, the mechanical force may be achieved via at least one of interlocking teeth or friction.

In a default condition, the second rotor may be decoupled from the first rotor, such that the controller is programmed to cause the second rotor to couple to the first rotor upon actuation of the surgical drill. Alternatively, in a default condition, the brake mechanism may be configured to lock the drill bit relative to the adapter, such that the controller is programmed to actuate the brake mechanism to unlock the drill bit relative to the adapter upon actuation of the surgical drill. The braking mechanism may be configured to lock the drill bit relative to the adapter via at least one of a friction plate and pads, clamping jaws, or biting teeth. Moreover, the chuck may comprise a telescoping channel configured to measure a depth of penetration of the drill bit.

In accordance with another aspect of the present disclosure, the adapter may include a linear actuator having a channel that extends therethrough, a shaft slidably disposed within the channel of the linear actuator. Accordingly, the brake mechanism may be disposed in communication with the linear actuation, such that, responsive to the signal, the controller causes the brake mechanism to lock the shaft relative to the linear actuator to arrest advancement of the drill bit. For example, in a default condition, the brake mechanism may be configured to lock the shaft relative to the linear actuator, and the controller may be programmed to actuate the brake mechanism to unlock the shaft relative to the linear actuator upon actuation of the surgical drill. A distal end of the shaft may be configured to contact a bony structure, such that as the drill bit advances through the bony structure, the shaft remains stationary relative to the bony structure and slides through the channel. Alternatively, a proximal end of the shaft may be configured to contact the surgical drill, such that as the drill bit advances through a bony structure, a distance between the surgical drill and the adapter decreases as the shaft slides through the channel. The adapter further may comprise a handle. In addition, a system comprising the adapter is provided. For example, the system may include the surgical tool. The surgical tool may include at least two electrodes configured to measure electrical conductivity and to generate the signal indicative of the electrical conductivity sensed by the elongated drilling portion.

In accordance with another aspect of the present disclosure, another adapter for use with a surgical tool comprising an elongated drilling portion is provided. For example, the adapter may include a sleeve comprising a lumen sized and shaped to receive the elongated drilling portion of the surgical tool therethrough, a brake mechanism configured to be actuated to arrest advancement of the elongated drilling portion relative to the sleeve, and a controller programmed to: receive a signal indicative of penetration depth of the elongated drilling portion, and responsive to the signal, cause the brake mechanism to arrest advancement of the elongated drilling portion relative to the sleeve.

In accordance with yet another aspect of the present disclosure, another adapter for use with a surgical tool comprising an elongated drilling portion is provided. For example, the adapter may include a sleeve comprising a lumen sized and shaped to receive the elongated drilling portion of the surgical tool therethrough, a brake mechanism configured to be actuated to arrest advancement of the elongated drilling portion relative to the sleeve, and a controller programmed to: receive a signal indicative of an electrical conductivity sensed by the elongated drilling portion; receive a signal indicative of penetration depth of the elongated drilling portion; and cause the brake mechanism to arrest advancement of the elongated drilling portion relative to the sleeve when changes in at least one of electrical conductivity or depth of penetration of the elongated drilling portion satisfy one or more predetermined conditions.

In accordance with another aspect of the present disclosure, a computer implemented system for operating an adapter for use with a surgical tool comprising an elongated drilling portion is provided. The system may include at least one processor configured to: receive a signal indicative of an electrical conductivity sensed by the elongated drilling portion as the elongated drilling portion penetrates an anatomic portion through a lumen of a sleeve of the adapter; and responsive to the signal, cause a brake mechanism to arrest advancement of the elongated drilling portion relative to the sleeve. The at least one processor may further be configured to: receive a signal indicative of penetration depth of the elongated drilling portion; and cause the brake mechanism to arrest advancement of the elongated drilling portion when changes in at least one of electrical conductivity or depth of penetration of the elongated drilling portion satisfy one or more predetermined conditions.

In addition, the at least one processor may further be configured to: sense changes in electrical conductivity during penetration by the elongated drilling portion; and cause the brake mechanism to arrest advancement of the elongated drilling portion when the changes in electrical conductivity satisfy one or more predetermined conditions. Moreover, the at least one processor may further be configured to: monitor penetration of the elongated drilling portion into a bony structure based on the signal; detect a condition associated with a change of measured electrical conductivity; and cause the brake mechanism to arrest advancement of the elongated drilling portion responsive to detection of the condition.

In some embodiments, the sleeve may include a stationary component comprising a spring, and the adapter may include a plunger coupled to the spring, such that the plunger may be configured to be slidably movable within the stationary component responsive to a force applied by the surgical tool. Accordingly, the at least one processor may be configured to cause the brake mechanism to arrest advancement of the elongated drilling portion relative to the sleeve by causing the brake mechanism to lock the plunger relative to the stationary component to thereby arrest advancement of the elongated drilling portion relative to the adapter. Additionally, the at least one processor may further be configured to: receive a signal indicative of penetration depth of the elongated drilling portion from a depth sensor coupled to the adapter; and cause the brake mechanism to arrest advancement of the elongated drilling portion when changes in at least one of electrical conductivity or depth of penetration of the elongated drilling portion satisfy one or more predetermined conditions.

In accordance with another aspect of the present disclosure, another adapter for use with a surgical tool comprising an elongated drilling portion is provided. For example, the adapter may include a sleeve comprising a lumen sized and shaped to receive the elongated drilling portion of the surgical tool therethrough, an alert mechanism operatively coupled to the elongated drilling portion, and configured to generate an alarm, and a controller programmed to: receive a signal indicative of an electrical conductivity sensed by the elongated drilling portion during penetration by the elongated drilling portion; and responsive to the signal, cause the alert mechanism to generate the alarm when changes in electrical conductivity satisfy one or more predetermined conditions. The controller may further be programmed to: receive a signal indicative of penetration depth of the elongated drilling portion; and cause the alert mechanism to generate the alarm when changes in at least one of electrical conductivity or depth of penetration of the elongated drilling portion satisfy one or more predetermined conditions. In addition, the adapter further may include a brake mechanism configured to be actuated to arrest advancement of the elongated drilling portion relative to the sleeve. Accordingly, the controller may further be programmed to cause the brake mechanism to arrest advancement of the elongated drilling portion when the changes in electrical conductivity satisfy the one or more predetermined conditions. Moreover, the controller may be further programmed to: receive a signal indicative of penetration depth of the elongated drilling portion; and cause the brake mechanism to arrest advancement of the elongated drilling portion when changes in at least one of electrical conductivity or depth of penetration of the elongated drilling portion satisfy one or more predetermined conditions.

In accordance with another aspect of the present disclosure, another computer implemented system for operating an adapter for use with a surgical tool comprising an elongated drilling portion is provided. The system may include at least one processor configured to: receive a signal indicative of an electrical conductivity sensed by the elongated drilling portion as the elongated drilling portion penetrates an anatomic portion through a lumen of a sleeve of the adapter; and responsive to the signal, cause an alert mechanism to generate an alarm when changes in electrical conductivity satisfy one or more predetermined conditions. The at least one processor may further be configured to: receive a signal indicative of penetration depth of the elongated drilling portion; and cause the alert mechanism to generate the alarm when changes in at least one of electrical conductivity or depth of penetration of the elongated drilling portion satisfy one or more predetermined conditions. Moreover, the at least one processor may further be configured to: cause a brake mechanism to arrest advancement of the elongated drilling portion when the changes in electrical conductivity satisfy the one or more predetermined conditions. In addition, the at least one processor may further be configured to: receive a signal indicative of penetration depth of the elongated drilling portion; and cause the brake mechanism to arrest advancement of the elongated drilling portion when changes in at least one of electrical conductivity or depth of penetration of the elongated drilling portion satisfy one or more predetermined conditions.

BRIEF DESCRIPTION OF THE DRAWINGS

FIGS. 11A to 11D illustrate use of the adapter of FIGS. 9A to 9D with an exemplary surgical hand tool in accordance with the principles of the present disclosure.

FIGS. 16A to 16E illustrate use of the adapter of FIGS. 9A to 9D with an exemplary sensing drill bit and a conventional surgical drill in accordance with the principles of the present disclosure.

DETAILED DESCRIPTION

Surgical drilling systems and methods are provided for performing surgical procedures, such as surgical drilling into bony structures, while guided by a conductivity sensing system. Systems configured in accordance with the principles of the present disclosure include a universal adapter which may be coupled to any conventional surgical drill, e.g., a handheld surgical drill, and a drill bit having conductivity sensing capabilities. Alternatively, the universal adapter may be coupled to a robotic arm of a surgical robotic system. To prevent injury to the patient, the adapter automatically arrests advancement of the drill bit responsive to a sensed conductivity by the drill in near real-time, e.g. within a few milliseconds to seconds.

Adapters described herein are particularly advantageous for use in the field of orthopedic surgery and spine surgery to assist a surgeon during a surgical procedure in placing an implant in one or more vertebrae of a patient's spine. The adapter thus enables improved placement precision and prevents risk of damage related to unintended intrusion into sensitive functional tissues, such as the spinal cord, nerve endings, and vascular structures. Although the devices and methods of the invention are described herein with respect to an application in a vertebra, and more generally in bony structure, they are not limited to such an application. Instead, the principles of the present invention advantageously may be applied to any anatomic portion comprising different mediums and having an electrical characteristic, such as a conductivity or resistivity, which varies as a function of the capacities of the mediums to conduct an electric current.

Figure 1:
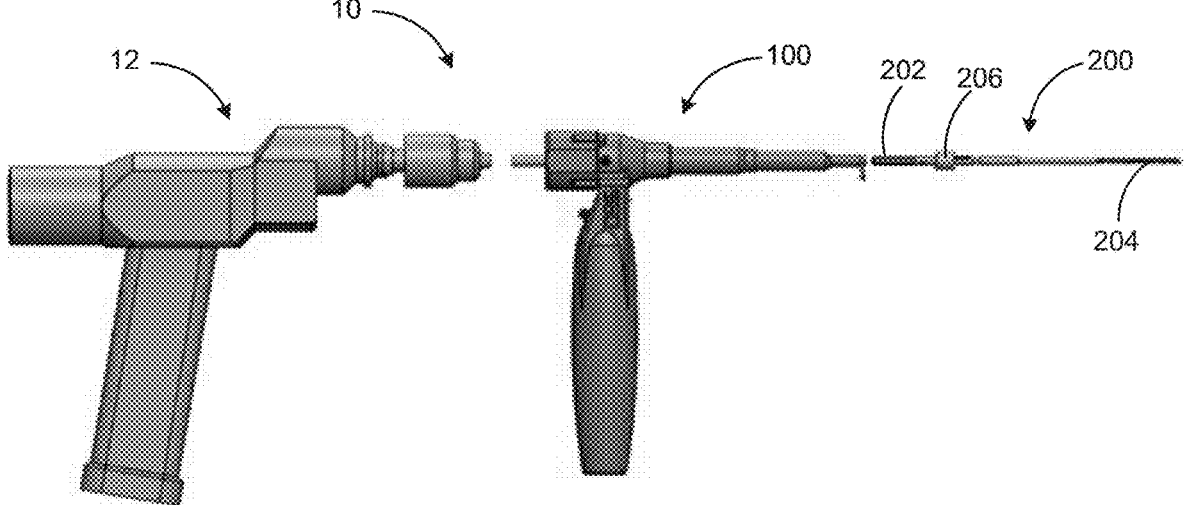
FIG. 1 illustrates an exemplary surgical drilling system constructed in accordance with the principles of the present disclosure.

Referring now to FIG. 1, an exemplary surgical drilling system configured in accordance with one aspect of the present disclosure is described. As shown in FIG. 1, surgical drilling system 10 includes universal adapter 100, conventional surgical drill 12, and conductivity-sensing drill bit 200. Surgical drill 12 may be any conventional surgical drill configured to receive and transmit rotary motion to a drill bit. Adapter 100 may be coupled to surgical drill 12 at its proximal end and may have a sleeve configured to receive drill bit 200 at its distal end, such that surgical drill 12 transmits rotary motion to drill bit 200 via adapter 100, as described in detail below. Drill bit 200 may include proximal end 202 sized and shaped to be received by adapter 100, e.g., a chuck of adapter 100, distal end 204 configured to contact and penetrate, e.g., tissue and/or bone, and conductor 206 for electrically coupling drill bit 200 to adapter 100.

Figure 2:
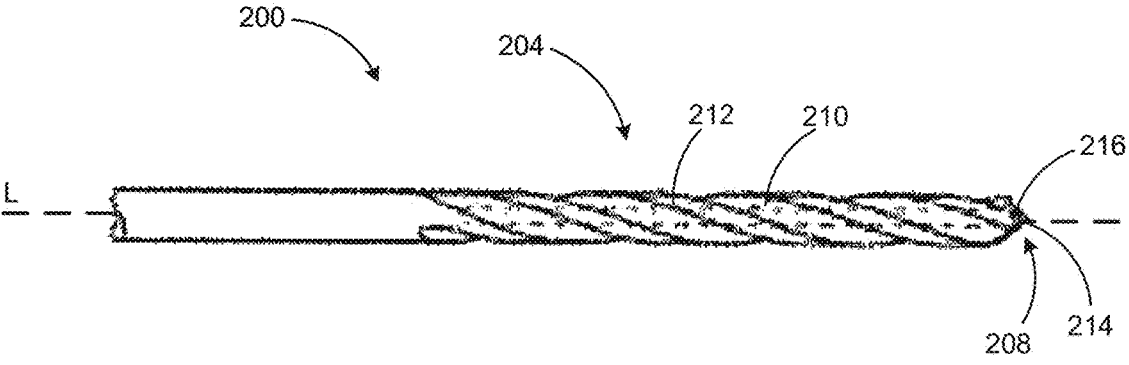
FIG. 2 illustrates an exemplary surgical drill bit for use with a surgical drill system of the present disclosure.

Referring now to FIG. 2, distal end 204 of drill bit 200 is described. Distal end 204 of drill bit 200 is configured to penetrate an anatomic portion, such as a region that includes a vertebra and surrounding tissue. As is well understood in the surgical arts, it is important to ensure precise positioning of drill bit 200 to avoid damaging or transiting the inner layer of cortical bone that delimits the foramen, or the outer layer, of cortical bone near the nerve endings. Adapter 100 preferably is configured to emit a warning signal that varies as a function of the sensed electrical characteristic by drill bit 200 when it is moved within an anatomic portion, and to arrest penetration by drill bit 200 if drill bit 200 approaches an anatomic portion that should not be penetrated, e.g., a breach condition.

Drill bit 200 operates analogously to the hand tool described in U.S. Pat. No. 7,580,743, the entire contents of which are incorporated herein by reference, which device is commercially available from the assignee of the present application under the tradename PediGuard®. Drill bit 200 also may constitute an implant to be placed in the anatomical structure, such as a screw, and in particular a pedicle screw.

Referring still to FIG. 2, drill bit 200 extends along longitudinal axis L between proximal end 202 and distal end 204, forming tip 208 for penetrating bony structure. Drill bit 200 generally has a cylindrical external surface of circular cross-section extending along longitudinal axis L and includes one or more spiral cutting edges that extend proximally from tip 208. The body of drill bit 200 could, however, have any other shape, in particular cylindrical with a polygonal or other cross-section. Additionally or alternatively, drill bit 200 may be a threaded drill bit. Drill bit 200 comprises first electrode 210, cylindrical and of conductive material, extending inside drill bit 200 parallel to longitudinal axis L. In particular, first electrode 210 is arranged in a central bore of drill bit 200 and extends coaxially to longitudinal axis L up to a free end having first contact surface 214, which is flush with the external surface of drill bit 200 at tip 208.

Drill bit 200 also includes second electrode 212, annular and of conductive material, extending along longitudinal axis L around first electrode 210. In particular, second electrode 212 is formed by a portion of drill bit 200 itself, made in this case of a conductive material. Second electrode 212 has second contact surface 216 composed of a cylindrical portion parallel to longitudinal axis L and corresponding to a lateral surface of drill bit 200, and an annular portion transverse to longitudinal axis L corresponding to a distal surface of drill bit 200.

A layer of electrically insulating material is interposed between first electrode 210 and second electrode 212 such that first contact surface 214 and second contact surface 216 can come into contact, at a distance from one another, with the anatomic portion during penetration of drill bit 200 into the anatomic portion. It should be understood, however, that the invention is not limited to the embodiment illustrated by drill bit 200, and other shapes are possible, such as, for example, that first electrode 210 and second electrode 212 are not arranged coaxially but may be formed from a rod of conductive material inserted into drill bit 200. Furthermore, first electrode 210 and second electrode 212 each may have a point-like or other contact surface 214, 216, flush with the lateral surface or distal surface of drill bit 200. Alternatively, drill bit 200 could support two or more first electrodes 210 and two or more second electrodes 212.

Figure 3A:
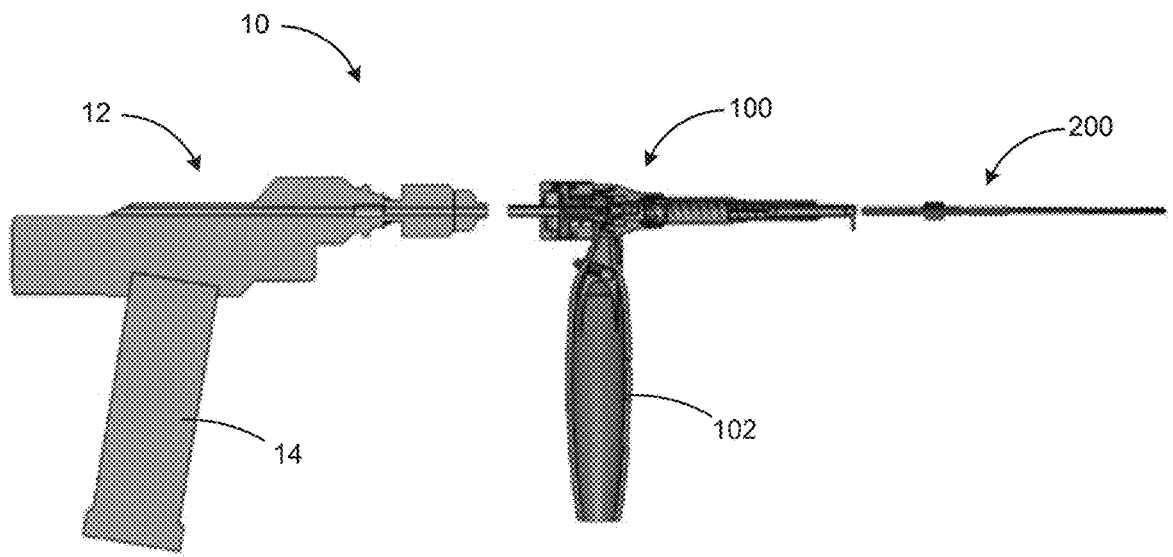
FIGS. 3A and 3B are a cross-sectional view of the surgical drilling system of FIG. 1.
Figure 3B:
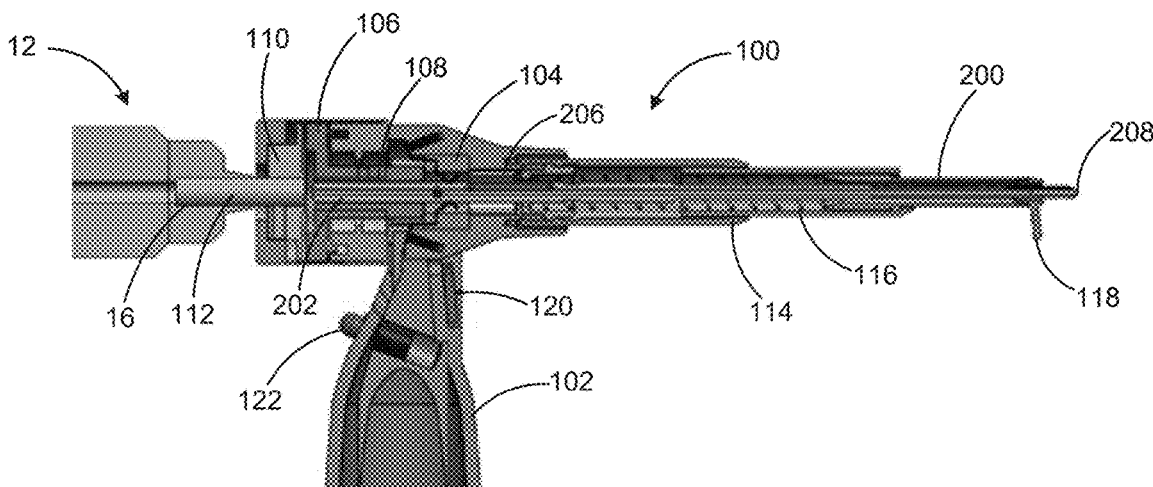

Referring now to FIGS. 3A and 3B, internal components of adapter 100 of system 10 are described. In FIG. 3B, adapter 100 may include a sleeve, e.g., chuck 104, for securely receiving proximal end 202 of drill bit 200 therethrough. Chuck 104 may include components that establish electrical connection to first and second electrodes 210 and 212 of drill bit 200, thus enabling electronics disposed within adapter 100 to emit an appropriate warning signal. Those components may include an electric generator, coupled to controller 150 (see FIG. 3C), e.g., an electric processing device mounted on a circuit board. The electric generator is connected to first electrode 210 and second electrode 212, and is suitable for applying one or more voltages across first contact surface 214 and second contact surface 216, e.g., via conductor 206. Controller 150 may be connected to the electric generator and to first electrode 210 and second electrode 212, e.g., via conductor 206, and is suitable for determining a measurement parameter related to the electrical characteristic based on a measurement electric current(s) induced by the applied voltage(s), and for emitting the warning signal corresponding to the measurement parameter. The measurement parameter may in particular be a voltage, an intensity of the electric current, conductivity or resistivity, or may be the result of processing one or more measurement electric currents, such as by integration, averaging, or the like, or may be the result of frequency analysis.

Adapter 100 also may enclose a device to supply electric power to the electric generator and controller 150, e.g., a battery. It also may include a communication interface communicating with controller 150, described below, by any suitable means, wired or wirelessly, e.g., via Bluetooth. In alternative embodiments, the electric generator and/or controller 150, as well as the other electronic components of drill bit 200, could be located remote from the body of the adapter 100. For example, at least some of the components could be carried by an external computing device, as described below.

Referring now to FIG. 3B, adapter 100 may include first rotor 110 configured to releasably engage surgical drill 12. For example, first rotor 110 may include shaft 112 sized and shaped to be securely received by chuck 16 of surgical drill 12. Accordingly, surgical drill 12 may transmit rotary motion to first rotor 110 upon actuation of surgical drill 12. In addition, adapter 100 may include second rotor 106 having channel 108 for securely receiving proximal end 202 of drill bit 200, such that rotation of second rotor 106 transmits rotary motion to drill bit 200. Additionally or alternatively, the first and/or second rotors may be, e.g., a shaft, a disc, an axis, a cylinder, etc.

First rotor 110 may be releasably coupled to second rotor 106, e.g., via an electromagnet clutch mechanism, such that surgical drill 12 may transmit rotary motion to drill bit 200 via first rotor 110 and second rotor 106 when first rotor 110 is mechanically coupled to second rotor 106. For example, controller 150 may cause a magnetic field to occur in second rotor 106 that causes it to electromagnetically couple to first rotor 110. Alternatively, the magnetic field may cause mechanical elements on rotors 106 and 110 to interengage, e.g., interlocking teeth or friction forces. Upon detection of a condition, as described below, controller 150 may cause the magnetic field to cease, thereby causing first rotor 110 to decouple from second rotor 106. This in turn will cease transmission of rotary motion from surgical drill 12 to drill bit 200, resulting in "auto-stop" of drill bit 200. In a default condition, prior to actuation of surgical drill 12, first rotor 110 may be decoupled from second rotor 106, such that, upon actuation of surgical drill 12, controller 150 causes first rotor 110 and second rotor 106 to couple together to transmit rotary motion from surgical drill 12 to drill bit 200.

In FIG. 3B, adapter 100 further may include one or more actuators 120. For example, actuator 120 may permit the user to override controller 150 and continue drilling despite the presence of a signal to auto-stop drill bit 200. Accordingly, actuation of actuator 120 may temporarily disable the auto-stop of drill bit 200, and cause controller 150 to cause re-engagement of first rotor 110 to second rotor 106, to thereby permit continued transmission of rotary motion from surgical drill 12 to drill bit 200. Upon release of actuator 120, controller 150 may proceed to auto-stop drill bit 200 if the condition is still detected based on the measured real-time electrical conductivity. Additionally or alternatively, one or more actuators 120 may permit the user to turn off the auto-stop functionality of controller 150, e.g., disable system 10, such that surgical drill 12 directly commands drill bit 200. In some embodiments, actuator 120 may be a voice-controlled actuator such that the surgeon may provide voice commands to cause controller 150 to either temporarily disable or disable system 10 in the manner described above.

Figure 3C:
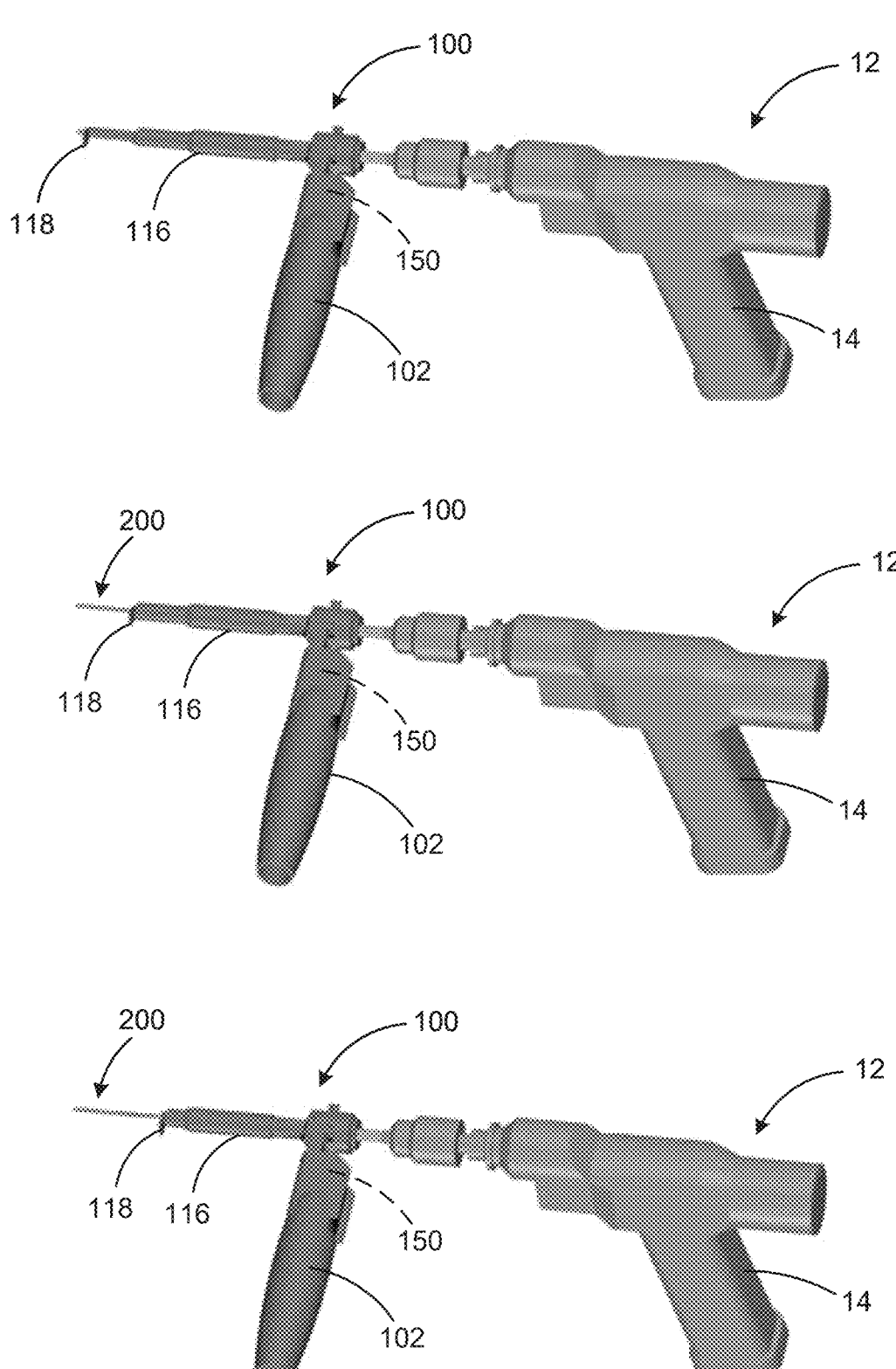
FIG. 3C illustrates operation of the surgical drilling system of FIG. 1.

In addition, adapter 100 may include telescoping channel 114 extending distally therefrom. Telescoping channel 114 may have spring 116 disposed therein to provide tension to telescoping channel 114. For example, spring 116 may apply a spring force to telescoping channel 114 to bias telescoping channel 114 in an extended configuration. The distal end of telescoping channel 114 may include lip 118, sized and shaped to contact and press against a surface adjacent to the entry point of drill bit 200 into, e.g., tissue or bone. Accordingly, as drill bit 200 penetrates into an anatomic portion, lip 118 will contact the surface adjacent to the drill bit entry point to cause telescoping channel 114 to contract axially as drill bit 200 advances into the anatomic portion, e.g., lip 118. The resulting telescoping action of telescoping channel 114 is illustrated in FIG. 3C. Moreover, telescoping channel 114 may include markings on its outer surface to facilitate depth measurement of drill bit 200 into the anatomic portion as telescoping channel 114 contracts. In some embodiments, adapter 100 may be coupled to surgical drill 12 such that handle 102 of adapter 100 may be angled, e.g., at 90 degrees, from surgical drill 12, to thereby improve stability and control of system 10.

Figure 4:
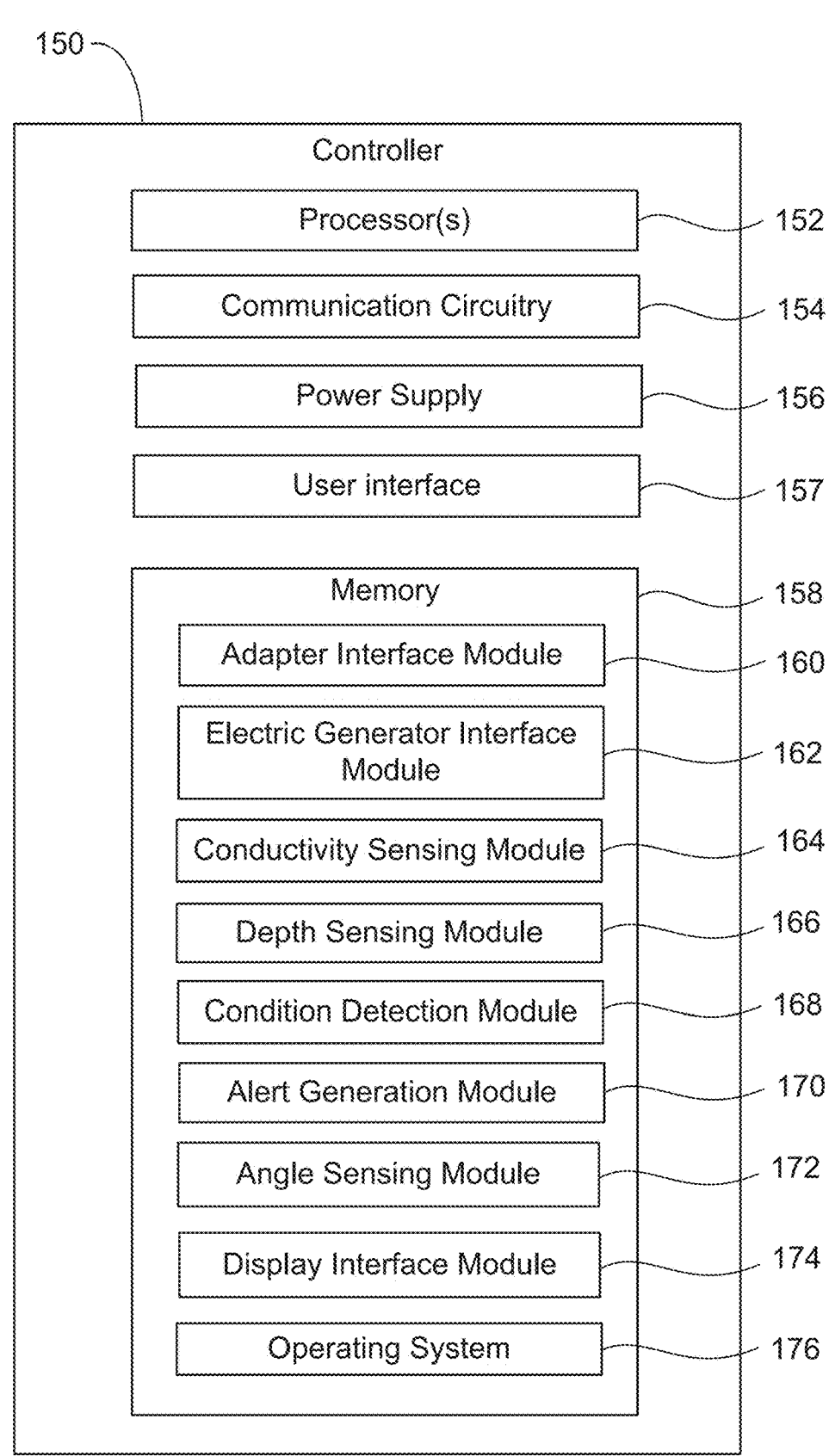
FIG. 4 is a schematic diagram of an exemplary controller constructed in accordance with the principles of the present disclosure.

Referring now to FIG. 4, components that may be included in controller 150 used in conjunction with adapter 100 are described. Controller 150 may be operatively coupled to adapter 100 and drill bit 200, such that controller 150 may receive signals indicative of electrical conductivity measurements from drill bit 200, e.g., based on electrical impedance of the surround tissue and/or bone, detect a condition, e.g., a breach during a surgical drilling procedure, based on the signals, and instruct adapter 100 to cease transmission of the rotary motion from surgical drill 12 to drill bit 200. Controller 150 may include one or more processors 152, communication circuitry 154, power supply 156, user interface 157, and/or memory 158.

Controller 150 includes memory, which may be RAM, ROM, Flash, or other known memory, or some combination thereof, and preferably includes storage in which data may be selectively saved. For example, programmable instructions may be stored to execute algorithms for detecting a breach or near breach of the drill bit during a surgical drilling procedure into bone. One or more electrical components and/or circuits may perform some of or all the roles of the various components described herein. Although described separately, it is to be appreciated that electrical components need not be separate structural elements. For example, controller 150 and communication circuitry 154 may be embodied in a single chip. In addition, while controller 150 is described as having memory, a memory chip(s) may be separately provided.

Controller 150 may incorporate processor 152, which may consist of one or more processors and may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. The controller also may be implemented as a combination of computing devices, e.g., a combination of a DSP and a microprocessor, a plurality of microprocessors, one or more microprocessors in conjunction with a DSP core, or any other such configuration.

Controller 150 may contain memory and/or be coupled, via one or more buses, to read information from, or write information to, memory. The memory may include processor cache, including a multi-level hierarchical cache in which different levels have different capacities and access speeds. The memory may also include random access memory (RAM), other volatile storage devices, or non-volatile storage devices. The storage devices can include, for example, hard drives, optical discs, flash memory, and Zip drives.

Controller 150, in conjunction with firmware/software stored in the memory may execute an operating system (e.g., operating system 176), such as, for example, Windows, Mac OS, Unix or Solaris 5.10. Controller 150 also executes software applications stored in the memory. In one non-limiting embodiment, the software comprises, for example, Unix Korn shell scripts. In other embodiments, the software may be programs in any suitable programming language known to those skilled in the art, including, for example, C++, PHP, or Java.

Communication circuitry 154 may include circuitry that allows controller 150 to communicate with the electronic components of adapter 100, e.g., the electric generator, one or more depth sensors, power supply 156, an alarm system, one or more actuators 120, first rotor 110, second rotor 106, etc., and with electrodes 210, 212 via conductor 206. Communication circuitry 154 may be configured for wired and/or wireless communication over a network such as the Internet, a telephone network, a Bluetooth network, and/or a WiFi network using techniques known in the art. Communication circuitry 154 may be a communication chip known in the art such as a Bluetooth chip and/or a WiFi chip. Communication circuitry 154 permits controller 150 to transfer information, such as signals indicative of a breach or near breach associated with spinal drilling, locally and/or to a remote location such as a server.

Power supply 156 may supply alternating current or direct current. In direct current embodiments, power supply may include a suitable battery such as a replaceable battery or rechargeable battery and apparatus may include circuitry for charging the rechargeable battery, and a detachable power cord. Power supply 156 may be charged by a charger via an inductive coil within the charger and inductive coil. Alternatively, power supply 156 may be a port to allow the adapter to be plugged into a conventional wall socket, e.g., via a cord with an AC to DC power converter and/or a USB port, for powering components within the device. Power supply 156 may be designed to supply power to the components of the adapter.

User interface 157 may be used to receive inputs from, and/or provide outputs to, a user. For example, user interface 157 may provide information to the user on the detection of a breach or near breach during the drilling procedure. User interface 157 further may include an audible device and/or volume control to selectively increase or decrease an audio output. User interface 157 may include a touchscreen, switches, dials, lights, an LED, e.g., LED 122 (shown in FIG. 3B), an LED matrix, other LED indicators, or other input/output devices for receiving inputs from, and/or providing outputs to, a user. In other embodiments, user interface 157 may not be present on the adapter, but is instead provided on a remote, external computing device communicatively connected to the adapter via the communication circuitry 154. User interface 157 also may be a combination of elements on the adapter and a remote computing device.

Memory 158, which is one example of a non-transitory computer-readable medium, may be used to store operating system (OS) 176, adapter interface module 160, electric generator interface module 162, conductivity sensing module 164, depth sensing module 166, condition detection module 168, alert generation module 170, angle sensing module 172, and display interface module 174. The modules are provided in the form of computer-executable instructions that may be executed by processor 152 for performing various operations in accordance with the disclosure. Instructions may be stored, for example, for executing algorithms associated with the breach detection as described in U.S. Pat. No. 11,344,372 to Bourlion or U.S. Patent Appl. No. 2022/0361896 to Bette, the entire contents of each of which are incorporated herein by reference.

Adapter interface module 160 may be executed by processor 152 for communicating with and actuating electronic components of adapter 100. For example, adapter interface module 160 may be operatively coupled to second rotor 106, such that adapter interface module 160 may be executed by processor 152 to cause second rotor 106 to generate a magnetic field to couple with first rotor 110 upon actuation of surgical drill 12. Accordingly, adapter interface module 160 may receive a signal from first rotor 110 indicating that surgical drill 12 is being actuated, to thereby cause second rotor 106 to be coupled to first rotor 110, such that rotary motion may be transmitted from surgical drill 12 to drill bit 200. Moreover, adapter interface module 160 may cause cessation of the magnetic field to cause second rotor 106 to decouple from first rotor 110 upon detection of a condition by condition detection module 168, as described in further detail below.

Electric generator interface module 162 may be executed by processor 152 for causing the electric generator of adapter 100 to apply one or more voltages across first contact surface 214 and second contact surface 216 of drill bit 200 during penetration of the anatomic portion by drill bit 200.

Conductivity sensing module 164 may be executed by processor 152 for receiving one or more signals from first electrode 210 and second electrode 212 indicative of measured electrical conductivity as drill bit 200 penetrates the anatomic portion. Specifically, conductivity sensing module 164 may determine a measurement parameter related to the electrical characteristic, e.g., voltage, an intensity of the electric current, conductivity or resistivity, based on a measurement electric current(s) induced by the applied voltage(s). Accordingly, conductivity sensing module 164 may measure the electrical conductivity, e.g., based on electrical impedance of the tissue and/or bone surrounding tip 208 of drill bit 200, as drill bit 200 penetrates the anatomic portion in real-time.

Depth sensing module 168 may be executed by processor 152 for receiving one or more signals from one or more depth sensors coupled to adapter 100 and/or drill bit 200, and determining the depth of penetration of drill bit 200 into the anatomic portion based on the one or more signals. For example, a first depth sensor may be positioned on a stationary portion of adapter 100, and a second depth sensor may be positioned on the distal end of telescoping channel 114, such that the depth sensing module 166 may determine the distance between the first and second depth sensors by receiving signals from each of the first and second depth sensors indicative of the relative position of the first and second depth sensor. Alternatively or additionally, an optical depth sensor may be positioned at the distal end of telescoping channel 114 and may emit a laser to determine the depth of tip 208 of drill bit 200. Accordingly, depth sensing module 166 may determine the depth of penetration of drill bit 200 into the anatomic portion based on one or more signals received from the optical depth sensor.

Condition detection module 168 may be executed by processor 152 for detecting a condition, e.g., a breach during a surgical drilling procedure, based on signals indicative of at least one of the measured electrical conductivity by conductivity sensing module 164 or the determined depth of penetration of drill bit 200 by depth sensing module 166. Specifically, condition detection module 168 may execute one or more algorithms stored therein to mathematically detect when changes in electrical conductivity and/or penetration depth, e.g., as drill bit 200 penetrates into the anatomic portion, satisfy predetermined conditions, indicating a breach condition. For example, based on the signals indicative of electrical conductivity and/or penetration depth measurements, condition detection module 168 may detect a breach condition such as transition to the inner layer of cortical bone delimiting the foramen, or transition to the outer layer of cortical bone near the nerve endings. A goal may be to cease transmission of rotary motion from surgical drill 12 to drill bit 200 when rapid variations in the signals are observed, and a delay of more than one second may cause a breach at the end of drilling. Moreover, based on the signals indicative of electrical conductivity and/or penetration depth measurements, condition detection module 168 may determine that one or more additional predetermined conditions are satisfied, e.g., when a predetermined maximum depth of penetration is reached, when a predetermined depth of penetration a predetermined distance beyond the depth when a breach condition is detected is reached, e.g., 3 mm beyond the breach condition depth such that the cortex is completely perforated so that a bone screw may be inserted such that its first threads bite the cortical wall for a "bicortical fixation" technique, when a cancellous and/or cortical is reached, etc. In some embodiments, condition detection module 168 may detect a condition based on changes in measured electrical conductivity as a function of penetration depth.

Condition detection module 168 may integrate an algorithm during signal preprocessing, which executes a reversed filter:

$$s(t) = \frac{\sigma(t) - (1 - \alpha)\sigma(t-1)}{\alpha}$$

As described in U.S. Pat. No. 11,344,372, this makes it possible to recover the unprocessed value of the signal at time t from the filtered signal, and at the same time to cancel out the delays. The warning signal may then be used to cease generation of the magnetic field to cause second rotor 106 to decouple from first rotor 110 to auto-stop drill bit 200 when one or more predetermined conditions are satisfied, e.g., just before a breach is made, as indicated by the predetermined change in electrical conductivity and/or penetration depth.

Penetration into the cortical bone is detected when the warning signal drops below a critical threshold $sc_1$. When the cortical bone has been penetrated, an impending breach is detected when the signal rises above its minimum value $s_{min}$ with a deviation greater than a threshold $sc_2$. In the experiments conducted, the thresholds $sc_1$ and $sc_2$ are imposed before the experiment (adjustment made based on initial tests). By contrast, the minimum reference value $s_{min}$ is not very repeatable from one drilling to another; it is therefore calculated automatically online.

The interpretation of the instrument signal can be described by the following pseudo-code:

---

Initialization: $s_{min} \leftarrow \infty$ ; $flag_{cortical} = 0$

---

For each new value received from the signal (t), loop as follows:

---

1. Calculate the minimum signal value:
If $s(t) < S_{min}$, then $S_{min} \leftarrow s(t)$
2. Detect entry into the cortical bone:
If $s(t) < S_1$ and $flag_{cortical} = 0$, then $flag_{cortical} \leftarrow 1$
3. In the cortical bone, detect an impending breach:
If $flag_{cortical} = 1$ and $(s(t) - s_{min}) > s_2$, then cease transmission of rotary motion.

---

Adapter interface module 160 may cause electronic components within adapter 100 to cease generation of the magnetic field to cause second rotor 106 to decouple from first rotor 110 to auto-stop drill bit 200 upon detection of a condition by condition detection module 168, as described above. In addition, adapter interface module 160 further may receive a signal, upon actuation of one or more actuators 120 of adapter 100, to temporarily disable or disable the system 10, to permit the user to override the auto-stop of drill bit 200, as described above.

Alert generation module 170 may be executed by processor 152 for generating a warning signal when condition detection module 168 detects a condition, and causing an alarm system of system 10 to emit a warning, e.g., an audible, visual, and/or tactile warning, based on the warning signal via, for example user interface 157. For example, alert generation module 170 may cause the alarm system, e.g., LED lights 122 (see FIG. 3B), to emit a flashing warning. Additionally or alternatively, alert generation module 170 may cause the alarm system, e.g., a speaker, to emit an audible warning signal frequency-modulated and possibly intensity-modulated, which may vary based on the change in electrical conductivity detected by condition detection module 168. Additionally or alternatively, alert generation module 170 may cause the alarm system, e.g., a vibrator, to emit a tactile warning signal frequency-modulated and possibly intensity-modulated, which may vary based on the change in electrical conductivity detected by condition detection module 168. In addition, the intensity of the alert generated may vary based on the measured depth of penetration by drill bit 200.

Angle sensing module 172 may be executed by processor 152 for receiving one or more signals from one or more angle sensors, e.g., a gravity angle sensor chip, an angular encoder, accelerometer, compass, and/or gyroscope, configured to sense an angle of adapter 100 relative to the position of the adapter in space and/or relative to a surface of the anatomic portion in 3D space. For example, the angle sensor may be disposed on adaptor 100 and/or on surgical drill 12, as described in further detail below. Angle sensing module 172 may determine the angle of adapter 100 relative to the position of the adapter in space and/or relative to the surface of the anatomic portion in 3D space, e.g., about the x, y, and z axes in three planes, based on the one or more signal received from the angle sensors. For example, angle sensing module 172 may calculate the angle based on the position of adaptor 100 in 3D space, and not based on the position of the anatomic portion as adaptor 100 is not tracked relatively to the anatomic portion. However, angle sensing module 172 may define the actual orientation of the anatomic portion, e.g., the spine or vertebrae, relative to adaptor 100 during a calibration phase, e.g., at the beginning of the surgery or between each drilling procedure. For example, during the calibration phase, adaptor 100 may be positioned vertically against the anatomic portion to be penetrated, e.g., a given vertebrae, while pointing one reference axis of the surgical instrument in a cephalic direction, e.g., towards the head of the patient, and this orientation may be set as a reference.

In another example, during the calibration phase, adaptor 100 may be positioned along a surgeon estimated direction in space that corresponds to the local orientation of the vertebra, e.g., given from the orientation of the spinal process, or along the estimated drilling trajectory e.g., the pedicle, and this orientation may be set as a reference. Accordingly, angle sensing module 172 may know both the space frame and the patient frame, such that angle sensing module 172 may determine the angle of adaptor 100 relative to the surface of the anatomic portion. Alternatively, the reference orientation may be used by the surgeon to help match specific anatomic angles known in scientific literature, such as the vertebral pedicle convergence angle, and align the instrument according such angle. Additionally, or alternatively, the drilling orientation as well as the angles on one side of the patient may be displayed, allowing the surgeon to replicate the angles on the opposite side of the patient for subsequent drillings.

Display interface module 174 may be executed by processor 152 for rendering and transmitting data to a display operatively coupled to controller 150, e.g., disposed on user interface 157 and/or a remote computing device, for displaying information associated with the transmitted data.

Figure 19A:
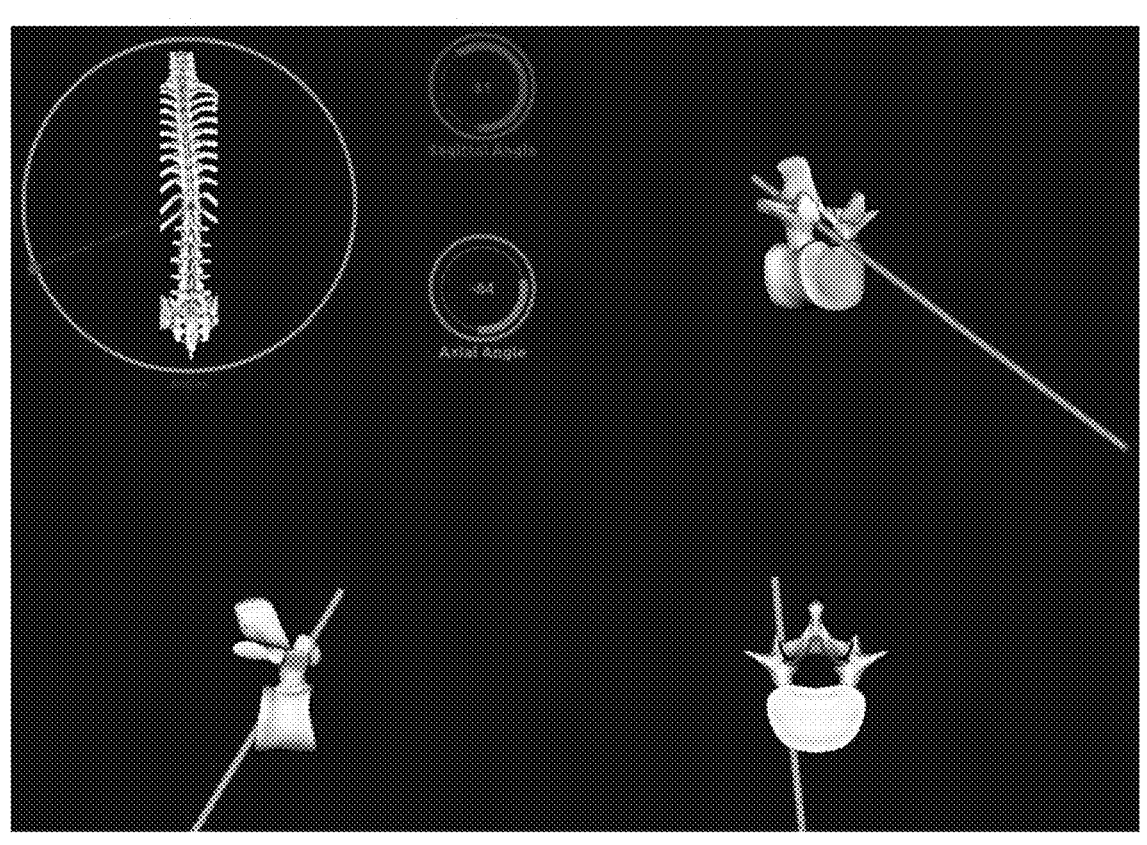
FIGS. 19A to 19D illustrate exemplary displays for displaying information in accordance with the principles of the present disclosure.
Figure 19B:
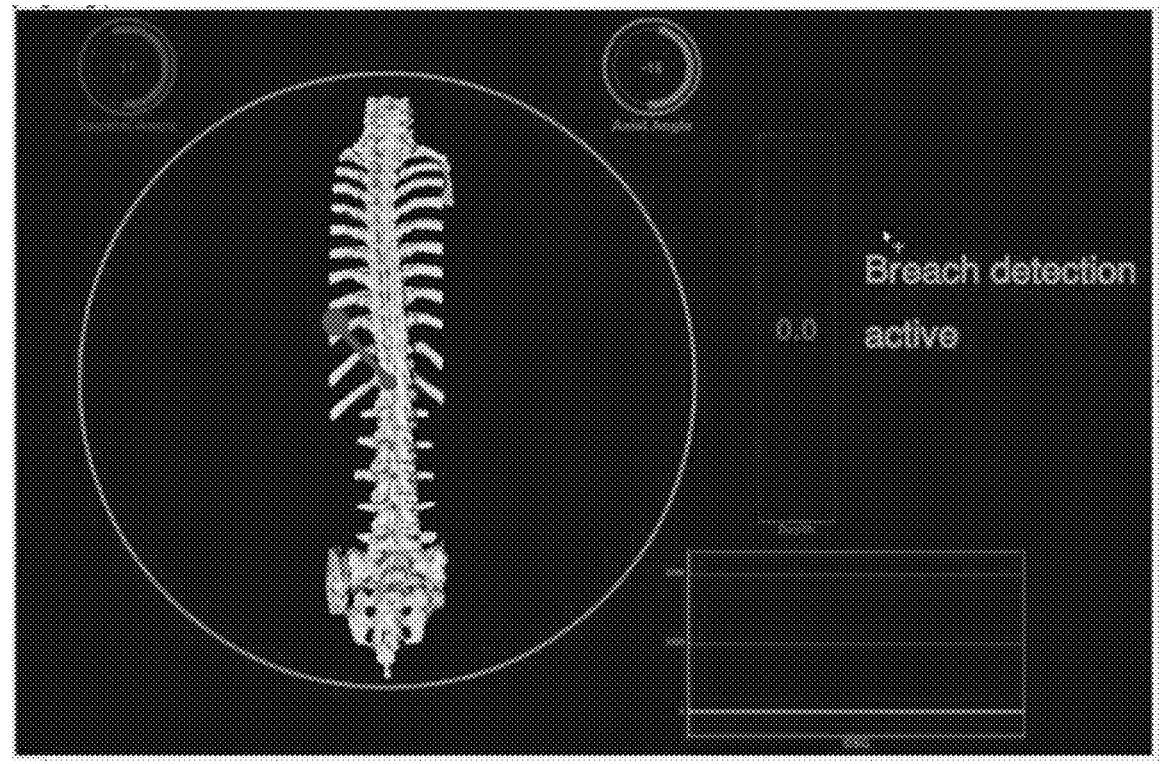
Figure 19C:
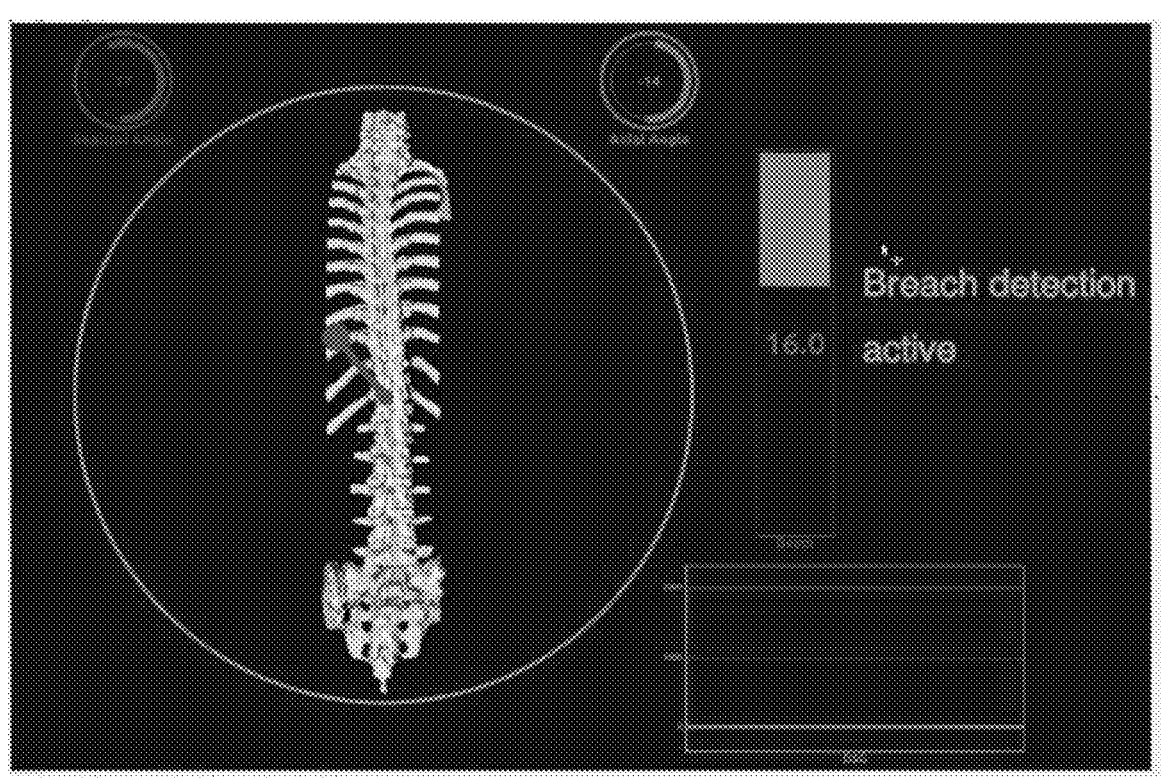
Figure 19D:
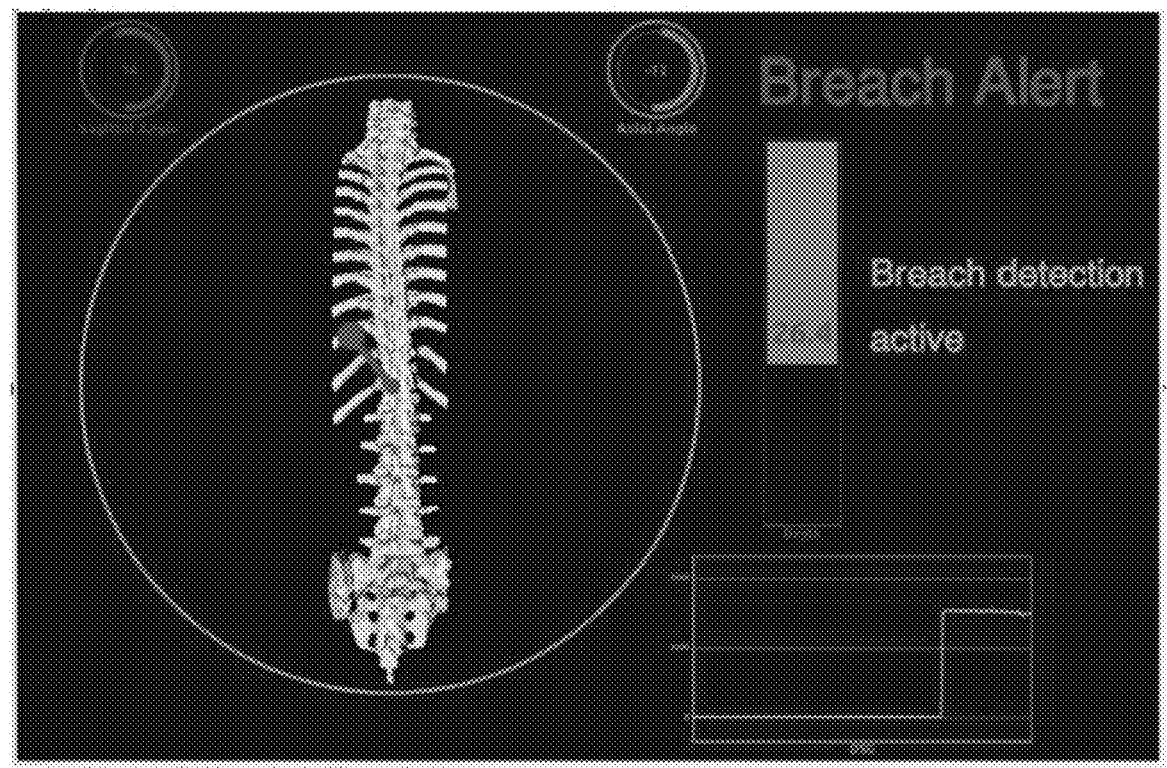

For example, display interface module 174 may generate or load virtual 3D models representative of one or more anatomic portions, e.g., the bone being penetrated, as well as indicators of the penetration path/angle, for display, as shown in FIG. 19A. As shown in FIG. 19A, information indicative of the angle of the penetration path, e.g., the sagittal angle and/or the axial angle, may be displayed alongside virtual 3D models of the bone and/or specific vertebrae being penetrated in real time. For example, the display may show the bone being penetrated at various angles. Moreover, display interface module 174 also may cause information indicative of the conductivity as determined by conductivity sensing module 164 and/or information indicative of the depth of penetration as determined by depth sensing module 166 to be displayed, as shown in FIGS. 19B to 19D. Moreover, display interface module 174 may cause the display to display an alert generated by alert generation module 170, e.g., when a breach is detected, as shown in FIG. 19D.

Figure 5:
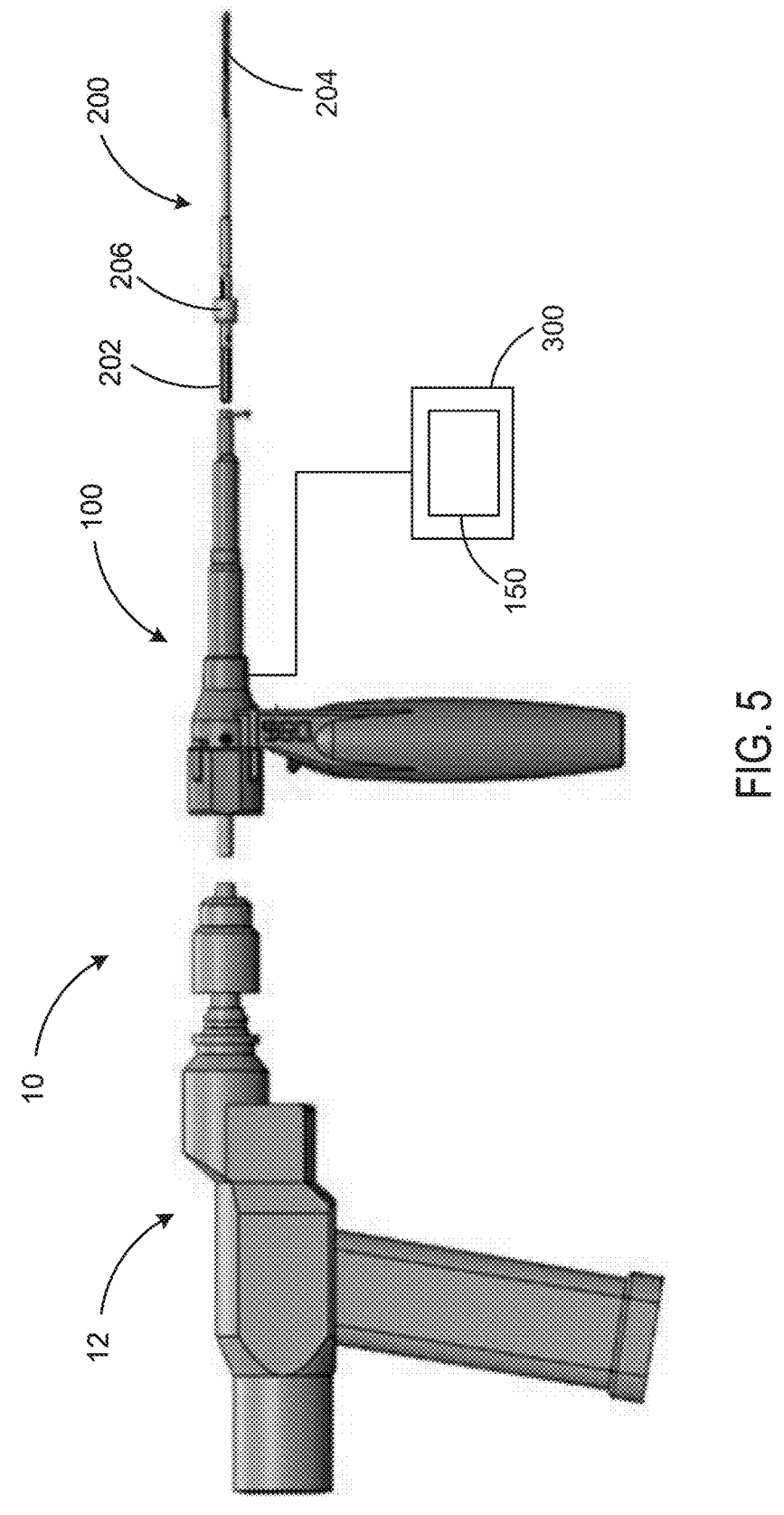
FIG. 5 illustrates the surgical drilling system of FIG. 1 with an external computing device.

Referring now to FIG. 5, in some alternative embodiments, system 10 further may include external computing device 300. For example, controller 150 may be disposed in external computing device 300, as opposed to within adapter 100. Accordingly, controller 150 may be operatively coupled to the electronic components of adapter 100 via a wired connection, e.g., one or more cables, or a wireless connection, e.g., Bluetooth connection. In addition, power supply 156 may be positioned in external computing device 300 for powering the electronic components of adapter 100. In some embodiments, external computing device 300 may include a display screen for displaying information regarding the measured electrical conductivity and/or depth of penetration of drill bit 200, as well as a visual warning message if a condition is detected, as described above.

Figure 6A:
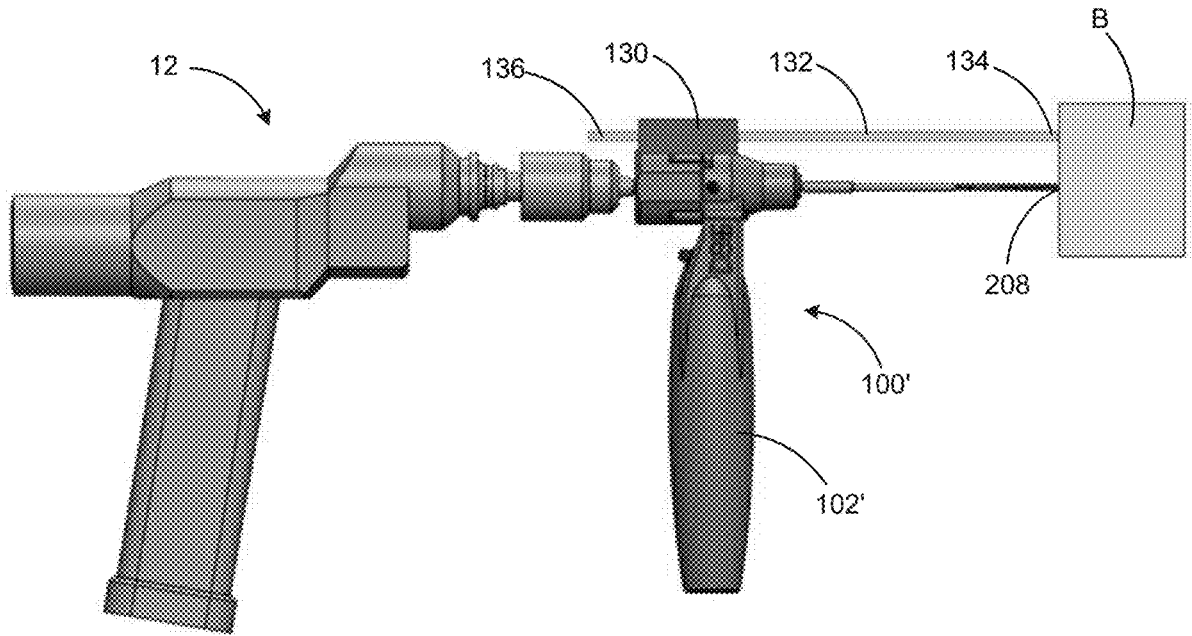
FIGS. 6A and 6B illustrate an alternative exemplary surgical drilling system constructed in accordance with the principles of the present disclosure.
Figure 6B:
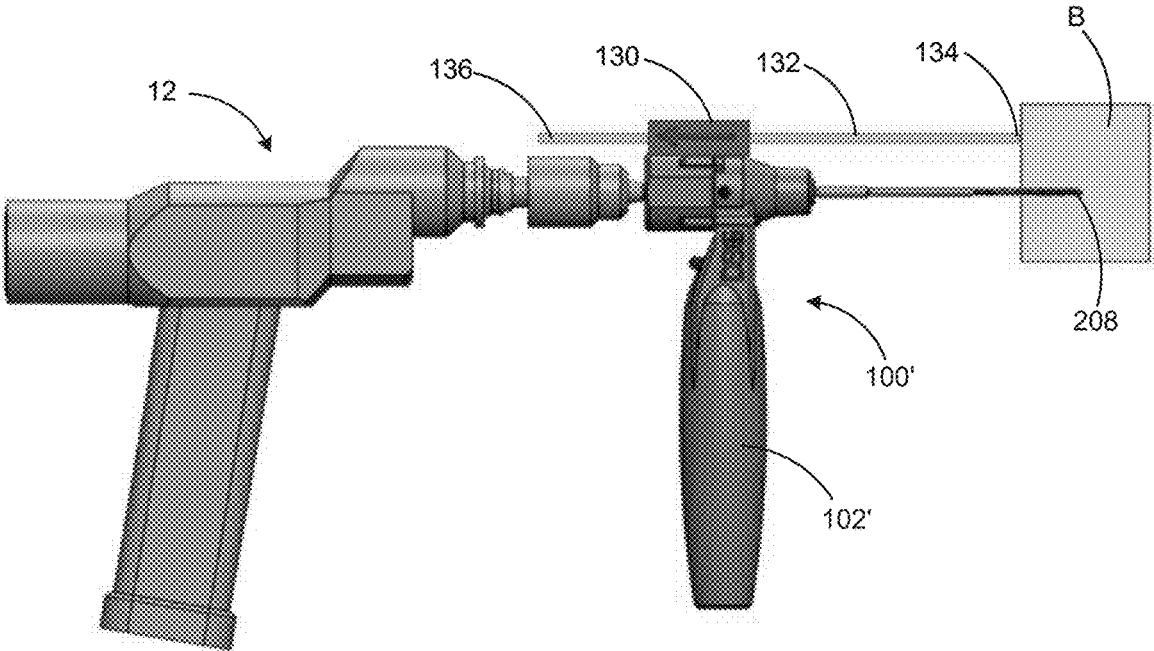

Referring to FIGS. 6A and 6B, an alternative adapter having a linear depth control mechanism is described. Adapter 100' may be constructed similarly to adapter 100, with similar components having like-prime reference numerals. For example, handle 102' corresponds with handle 102. Adapter 100' differs from adapter 100 in that adapter 100' includes linear actuator 130. In addition, adapter 100' may not include selectively engageable first and second rotors. Instead, drill bit 200 may be directly received by the chuck of surgical drill 12 within adapter 200 for transmission of rotary motion from surgical drill 12 to drill bit 200. Alternatively, adapter 100' may include first and second rotors similar to adapter 100. Moreover, adapter 100' may or may not include a telescoping channel. FIGS. 6A and 6B depict adapter 100' with the telescoping channel omitted. As shown in FIGS. 6A and 6B, linear actuator 130 may be disposed on an upper surface of adapter 100'. Alternatively, linear actuator 130 may be disposed on a side of adapter 100'. Linear actuator 130 has a channel extending therethrough, sized and shaped to slidably receive shaft 132. Shaft 132 includes proximal end 136, and distal end 134 configured to contact and engage with the surface of the anatomic portion, e.g., bone B.

Linear actuator 130 includes a brake mechanism disposed therein and configured to engage with shaft 132. The brake mechanism is operatively coupled to controller 150, such that upon detection of a condition by condition detection module 168, adapter interface module 160 of controller 150 causes the brake mechanism to lock shaft 132 relative to linear actuator 130. For example, during operation, distal end 134 of shaft 132 is positioned in contact with the surface of bone B. As tip 208 of drill bit 200 penetrates bone B, shaft 132 slides proximally through the channel of linear actuator 130 as handle 102' of adapter 100' advances towards bone B. Upon detection of the condition, controller 150 causes the brake mechanism to lock shaft 132 relative to linear actuator 130, which arrests advancement, e.g., further penetration, of drill bit 200 into bone B, due to the contact between distal end 134 of shaft 132 and bone B. Thus, even though rotary motion may continuously be transmitted from surgical drill 12 to drill bit 200, advancement of drill bit 200 is stopped. In some embodiments, shaft 132 may include markings on its outer surface to facilitate depth measurement of drill bit 200 into bone B. In a default condition, prior to actuation of surgical drill 12, the brake mechanism may be activated such that shaft 132 is locked relative to linear actuator 130. Accordingly, upon actuation of surgical drill 12, controller 150 causes the brake mechanism to unlock lock shaft 132 relative to linear actuator 130 to thereby permit advancement of drill bit 200.

Figure 7A:
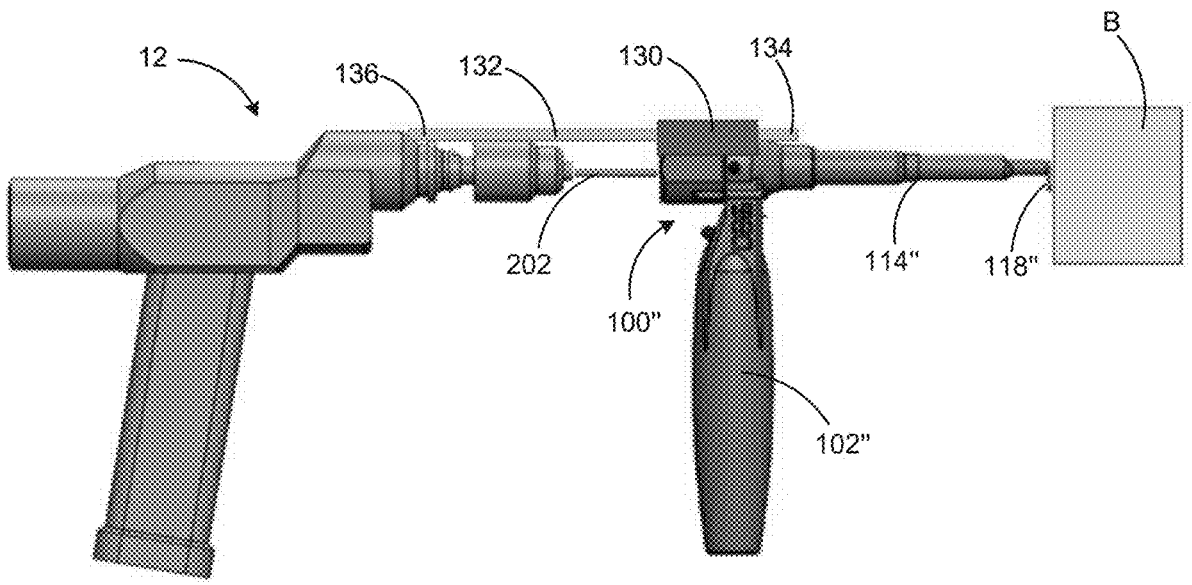
FIGS. 7A and 7B illustrate another alternative exemplary surgical drilling system constructed in accordance with the principles of the present disclosure.
Figure 7B:
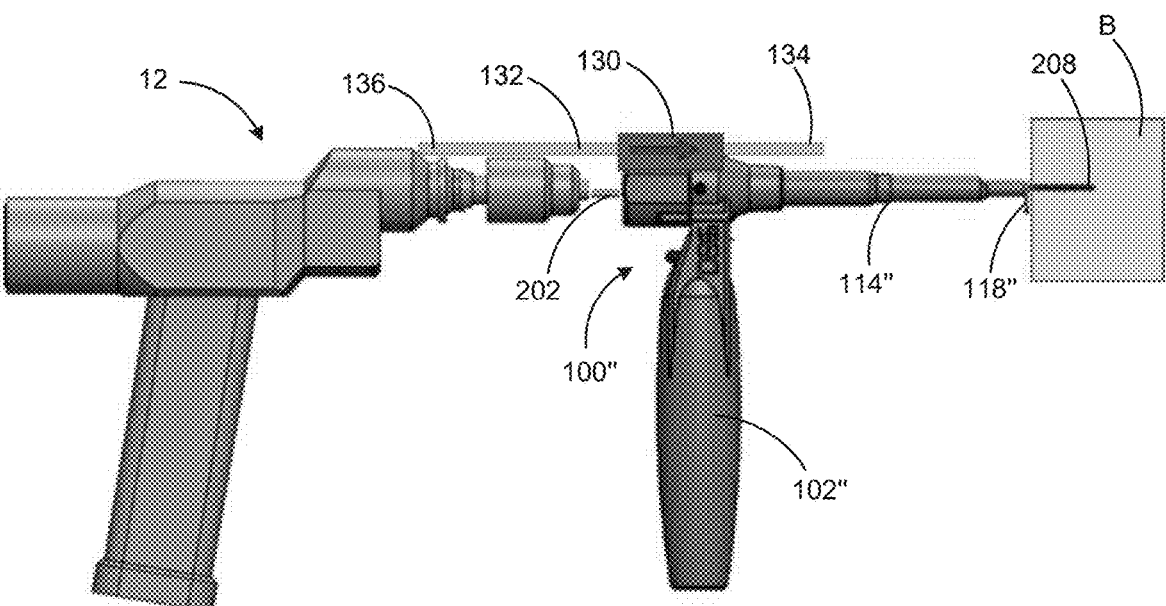

With respect to FIGS. 7A and 7B, another alternative exemplary surgical drilling system employing an inventive adapter having linear depth control is described. Adapter 100" may be constructed similarly to adapter 100', 100 with similar components having like-double prime reference numerals. For example, handle 102" corresponds with handle 102', telescoping channel 114" corresponds with telescoping channel 114, and lip 118" corresponds with lip 118. Unlike adapter 100, adapter 100" does not include selectively engageable first and second rotors for coupling surgical drill 12 to drill bit 200. Instead, drill bit 200 may be directly received by the chuck of surgical drill 12 for transmission of rotary motion from surgical drill 12 to drill bit 200. Moreover, telescoping channel 118" may be locked in position such that it does not contract during operation. Linear actuator 130 may be disposed on an upper surface of adapter 100" or alternatively, disposed on a side of adapter 100', such that proximal end 136 is in contact with surgical drill 12, as described below.

Unlike adapter 100', proximal end 136 is configured to contact and engage with a surface of surgical drill 12. A brake mechanism is operatively coupled to controller 150, such that upon detection of a condition by condition detection module 168, adapter interface module 160 of controller 150 causes the brake mechanism to lock shaft 132 relative to linear actuator 130. For example, during operation, lip 118" is positioned in contact with the surface of bone B, and proximal end 136 of shaft 132 is positioned in contact with surgical drill 12. As tip 208 of drill bit 200 penetrates bone B, shaft 132 slides distally through the channel of linear actuator 130 as surgical drill 12 advances towards handle 102" of adapter 100", while adapter 100" remains stationary relative to bone B via telescoping channel 114" and lip 118". Upon detection of the condition, controller 150 causes the brake mechanism to lock shaft 132 relative to linear actuator 130, which arrests advancement, e.g., further penetration, of drill bit 200 into bone B, due to the contact between proximal end 136 of shaft 132 and surgical drill 12. Thus, even though rotary motion may continuously be transmitted from surgical drill 12 to drill bit 200, advancement of drill bit 200 is stopped. In some embodiments, shaft 132 may include markings on its outer surface to facilitate depth measurement of drill bit 200 into bone B. In a default condition, prior to actuation of surgical drill 12, the brake mechanism may be activated such that shaft 132 is locked relative to linear actuator 130. Accordingly, upon actuation of surgical drill 12, controller 150 causes the brake mechanism to unlock lock shaft 132 relative to linear actuator 130 to thereby permit advancement of drill bit 200.

Figure 8A:
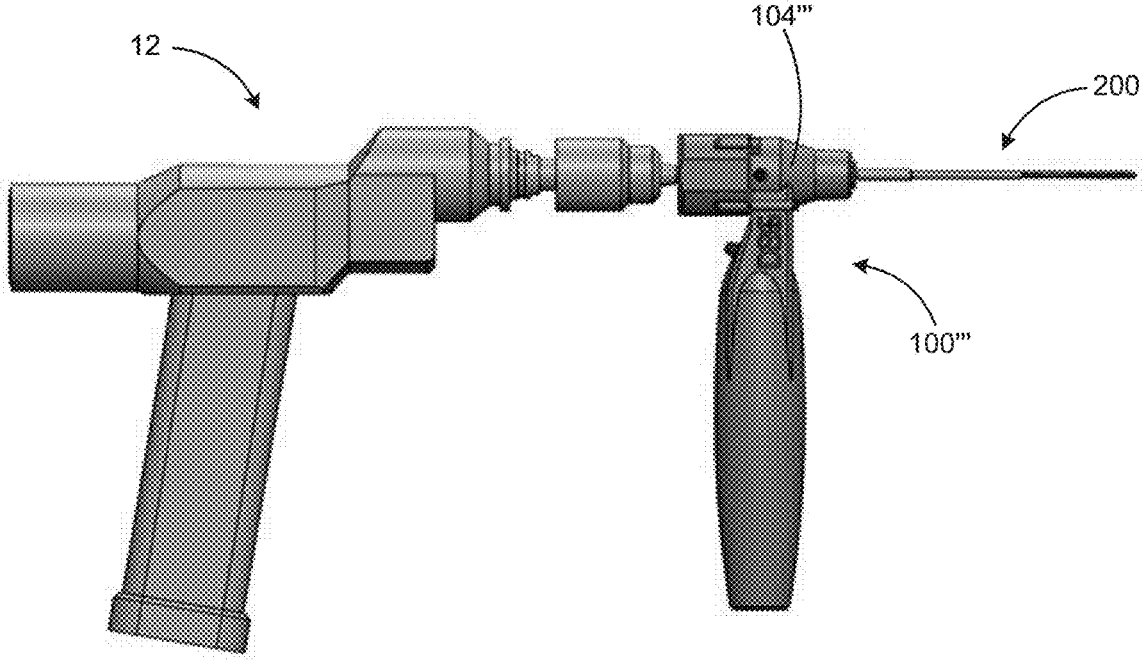
FIGS. 8A and 8B illustrate yet another alternative exemplary surgical drilling system constructed in accordance with the principles of the present disclosure.
Figure 8B:
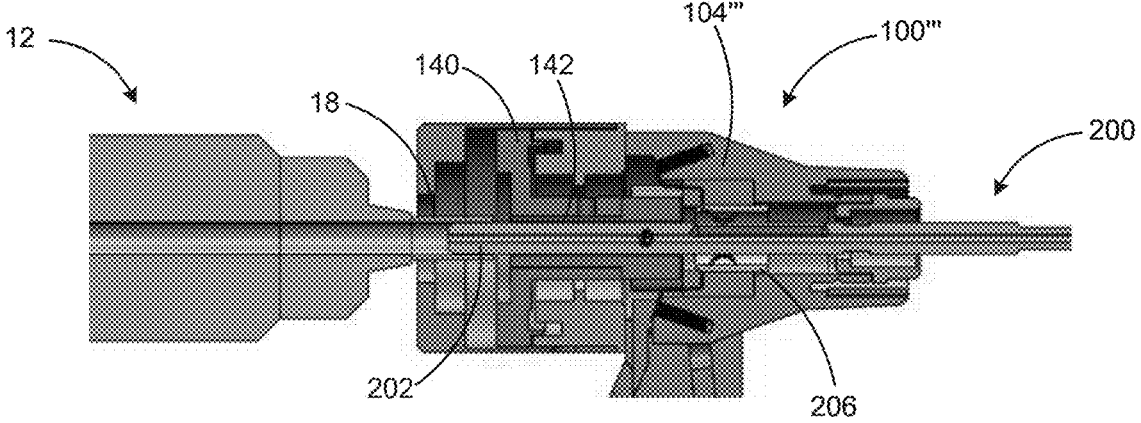

Referring now to FIGS. 8A and 8B, an adapter having a mechanical brake for use in a surgical drilling system is described. Adapter 100" may be constructed similarly to adapter 100 with similar components having like-triple prime reference numerals. For example, chuck 104" corresponds to chuck 104. Adapter 100" differs from adapter 100 in that adapter 100''' does not include selectively engageable first and second rotors for coupling surgical drill 12 to drill bit 200. Instead, drill bit 200 may be directly received by the chuck of surgical drill 12 for transmission of rotary motion from surgical drill 12 to drill bit 200. For example, the chuck of surgical drill 12 may have a receiving channel 18 for securely receiving proximal end 202 of drill bit 200. In addition, adapter 100" includes brake mechanism 140 having a channel extending therethrough for receiving proximal end 202 of drill bit 200 therethrough. Brake mechanism 140 may be engaged with drill bit 200 via at least one of a friction plate and pads, clamping jaws, or biting teeth.

Brake mechanism 140 is operatively coupled to controller 150, such that upon detection of a condition by condition detection module 168, adapter interface module 160 of controller 150 causes brake mechanism 140 to lock drill bit 200 relative to brake mechanism 140, and accordingly adapter 100". Accordingly, to stall the motor of surgical drill 12 to prevent transmission of rotary motion from surgical drill 12 to drill bit 200, the braking force/torque of braking mechanism 140 applied to drill bit 200 must be greater than the torque of surgical drill 12. For example, during operation, upon detection of the condition, controller 150 causes brake mechanism 140 to drill bit 200 relative to brake mechanism 140, which stops transmission of rotary motion from surgical drill 12 to drill bit 200. In a default condition, prior to actuation of surgical drill 12, brake mechanism 140 may be activated such that drill bit 200, and accordingly surgical drill 12, is locked relative to brake mechanism 140. Accordingly, upon actuation of surgical drill 12, controller 150 causes brake mechanism 140 to unlock drill bit 200 relative to brake mechanism 140 to thereby permit transmission of rotary motion from surgical drill 12 to drill bit 200.

Referring now to FIGS. 9A to 9D, an exemplary adapter for use with a surgical hand tool system such as a surgical hand tool and/or a conventional surgical drill is provided. For example, adapter 400 may be used with the hand tools described in U.S. Pat. No. 7,580,743, the entire contents of which are incorporated herein by reference, which device is commercially available from the assignee of the present application under the tradename PediGuard®. For example, the surgical hand tools may include a handle portion coupled to an elongated drilling portion having a distal end configured to contact and penetrate an anatomic portion, e.g., tissue and/or bone, via manual rotation of the handle. Moreover, the distal end of the surgical hand tool may include two or more electrodes as described above with regard to drill bit 200 of FIG. 2 coupled to an electric generator within the handle for measuring electrical conductivity in real time based on electric current(s) induced by the applied voltage(s) by the electrodes as the elongated drilling portion penetrates tissue and/or bone.

The electrodes may be operatively coupled to controller 450, e.g., an electric processing device mounted on a circuit board, which may determine a measurement parameter related to the electrical characteristic based on the measurement electric current(s), detect a breach condition based on the measurement parameter and/or penetration depth measurement of the elongated drilling portion, emit a warning signal corresponding to the measurement parameter and/or penetration depth measurement which may vary as a function of sensed electrical characteristics during penetration, and/or arrest further advancement of the surgical hand tool relative to adapter 400 if the distal end of the elongated drilling portion approaches an anatomic portion that should not be penetrated, e.g., a breach condition, as described in further detail below.

Additionally or alternatively, the electrodes may be operatively coupled to an electric processing device within the surgical hand tool, which is operatively coupled to controller 450 for transmitting data therebetween. As described above, the measurement parameter may in particular be a voltage, an intensity of the electric current, conductivity or resistivity, or may be the result of processing one or more measurement electric currents, such as by integration, averaging, or the like, or may be the result of frequency analysis. In addition, the surgical hand tools may include a device to supply electric power to the electric generator, e.g., a battery, as well as a communication interface communicating with controller 450, described below, by any suitable means, wired or wirelessly, e.g., via Bluetooth.

Figure 9A:
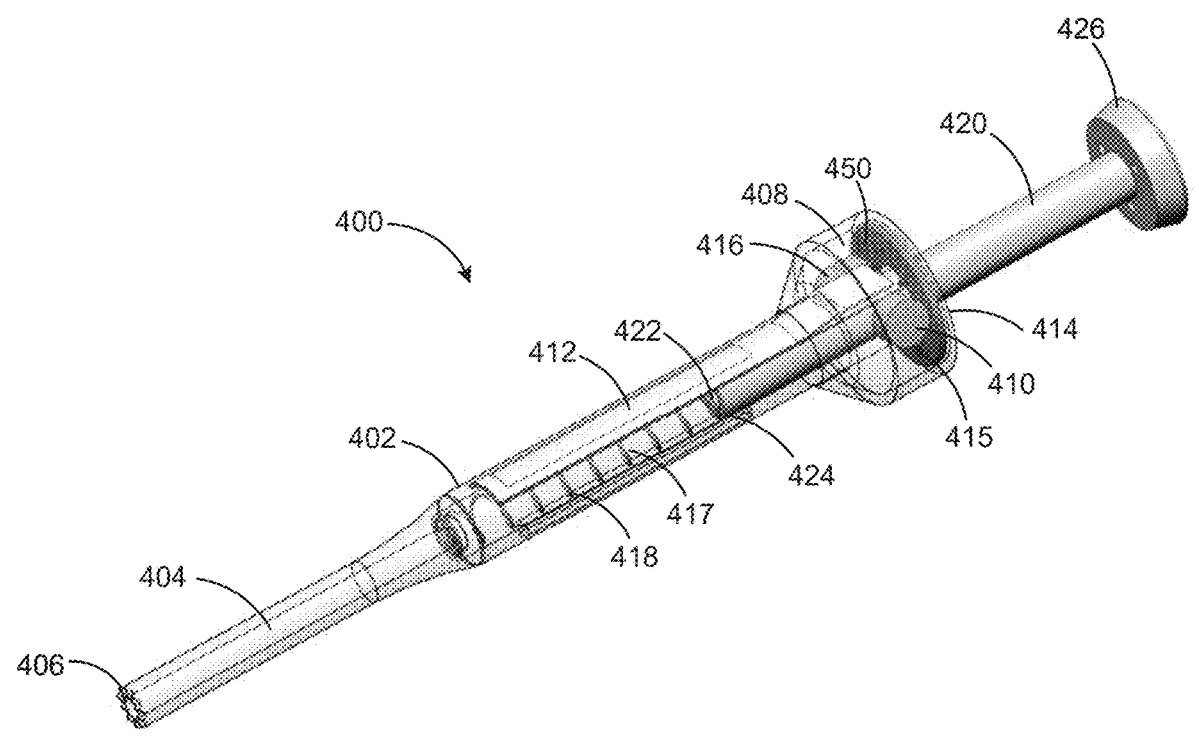
FIGS. 9A to 9D illustrate various views of an exemplary adapter for a surgical drilling system constructed in accordance with the principles of the present disclosure.
Figure 9B:
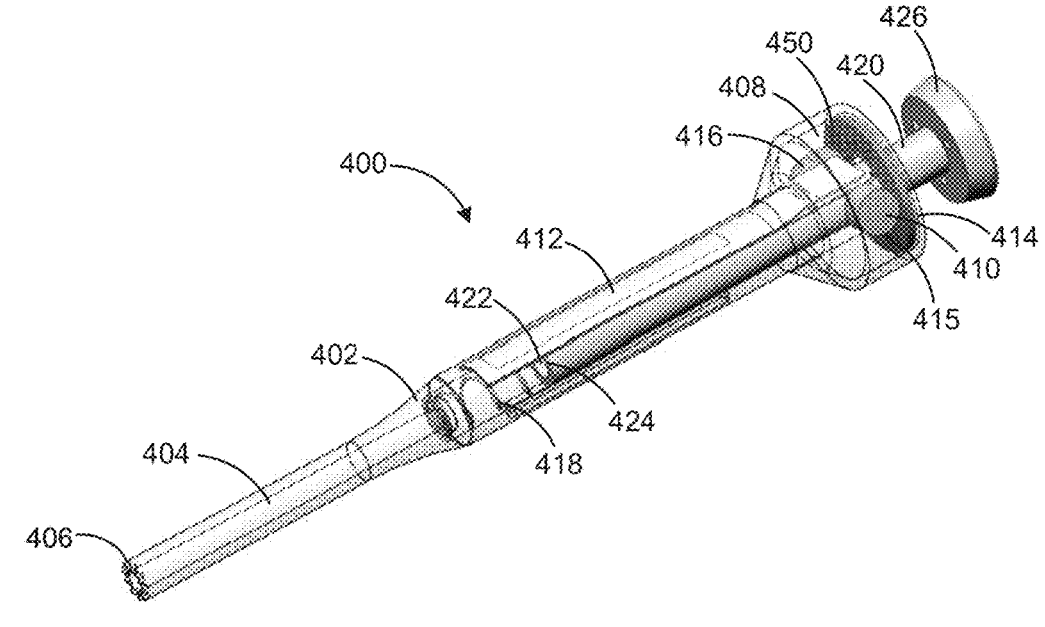
Figure 9C:
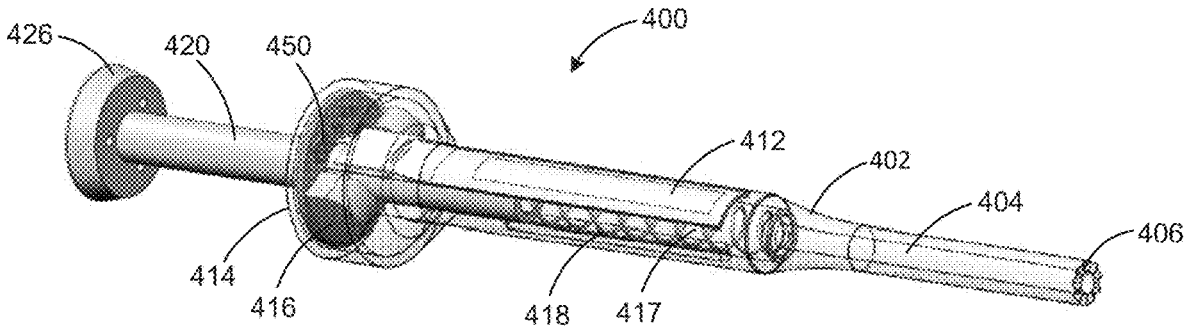

As shown in FIGS. 9A to 9D, adapter 400 may include a stationary component, e.g., sleeve 402, and plunger 420 slidably coupled to sleeve 402, e.g., via spring 418. Sleeve 402 may include lumen 404 extending therethrough from proximal end 414 to distal end 406, such that lumen 404 is sized and shaped to receive at least the elongated drilling portion of the surgical tool as the elongated drilling portion is advanced to penetrate tissue and/or bone. At least a portion of lumen 404 may include cavity 417 sized and shaped to have spring 418 disposed therein. Cavity 417 is further sized and shaped to receive the distal portion of plunger 420 therethrough. Distal end 424 of plunger 420 may be coupled to a proximal end of spring 418 to thereby provide tension to plunger 420. For example, spring 418 may apply a spring force to plunger 420 to bias plunger 420 in an extended configuration as shown in FIGS. 9A and 9C.

Figure 9D:
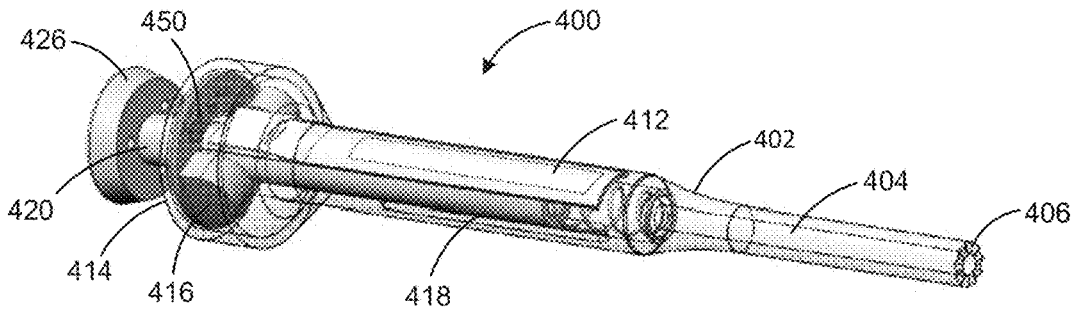

As shown in FIGS. 9B and 9D, upon application of a force to the proximal end of plunger 420, e.g., abutment portion 426 of plunger 420, by a stopper adjacent to the handle of the surgical hand tool, spring 418 may be compressed, such that plunger 420 advances distally through cavity 417 of sleeve 402, thereby forming a telescoping channel. As shown in FIGS. 9B and 9D, abutment portion 426 may comprise a flat profile. Abutment portion 426 may have an outer diameter that is larger than the outer diameter of the elongated shaft of plunger 420 that is received by cavity 417 to facilitate engagement with the stopper of the surgical hand tool. Advancement of plunger 420 within cavity 417 may be limited by the longitudinal length of cavity 417, such that plunger 420 cannot be advanced beyond the distal end of cavity 417 because the outer diameter of the elongated portion of plunger 420 may be larger than the diameter of the distal portion of lumen 404 of sleeve 402. Additionally or alternatively, advancement of plunger 420 within cavity 417 may be limited by the engagement of the proximal side of proximal end 414 of sleeve 402 and the distal side of abutment portion 426 of plunger 420, such that abutment portion 426 cannot be advanced beyond proximal end 414 because the outer diameter of abutment portion 426 may be larger than cavity 417 of sleeve 420.

Moreover, plunger 420 may include lumen 422 sized and shaped to receive the elongated drilling portion of the surgical tool as the elongated drilling portion is advanced to penetrate tissue and/or bone. Accordingly, lumen 422 may be concentrically aligned with lumen 404, such that the elongated drilling portion may be advanced through lumen

422, cavity 417, the distal portion of lumen 404, and out of distal end 406 of sleeve 402. Lumen 422 may have a diameter that is at least as large lumen 404. Distal end 406 may be sized and shaped to contact and press against a surface adjacent to the entry point of the elongated drilling portion into, e.g., tissue or bone. Accordingly, as the elongated drilling portion penetrates into an anatomic portion, distal end 406 will contact the surface adjacent to the entry point to cause spring 418 to contract axially as the distance between abutment portion 426 of plunger 420 and distal end 406 decreases as the elongated drilling portion advances into the anatomic portion.

The proximal region of sleeve 402 may include cavity 408 sized and shaped to house the electric components of adapter 400, e.g., controller 450, an electric generator, communication circuitry, depth sensor 410, brake mechanism 416, and/or sensor 415 for measuring the angle of adapter 400 relative to the space frame or the surface of the tissue or bone during penetration, e.g., a gravity angle sensor chip, an accelerometer, compass, and/or gyroscope. For example, sensor 415 may be configured to generate one or more signals indicative of the angle of adapter 400 in 3D space, e.g., about the x, y, and z axes in three planes, for transmission to controller 450. As will be understood by a person having ordinary skill in the art, although FIGS. 9A and 9B show sensor 415 disposed within cavity 408 of sleeve 402, sensor 415 may be disposed in other locations such as within cavity 417. Moreover, other components of the systems described herein (e.g., surgical drill 12, adapters 100, 100', 100", 100''', surgical hand tools 20, 30, 40, 50, sensing drill bit 500, etc.) may incorporate an angle sensor, e.g., within the respective handles or other suitable areas, for measuring the angle of the respective component relative to the surface of the tissue or bone during penetration in 3D space, and generating and transmitting signals indicative of the measured angle to controller 450.

As shown in FIGS. 9A to 9D, depth sensor 410 may be operatively coupled to a contact sensor, e.g., band 412, extending longitudinally within cavity 417, and a distal portion of the outer surface of plunger 420 may include one or more screws sized and shaped to engage with the inner surface of band 412 as plunger 420 is advanced through cavity 417, thereby generating an electrical impedance that varies as plunger 420 is advanced through cavity 417, such that the electrical impedance measured is indicative of penetration depth of the elongated drilling portion of the surgical hand tool. Depth sensor 410 may generate one or more signals indicative of the measured electrical impedance due to the engagement between the screw and band 412, and transmit the one or more signals to controller 450 for processing, e.g., determining the penetration depth based on the electrical impedance. Additionally or alternatively, depth sensor 410 may include at least one of a linear potentiometer, a laser distance sensor, an infrared distance sensor, an ultrasonic distance sensor, a Light Detection and Ranging (LiDAR) sensor, a 3D Time-of-Flight camera, linear magnetic or hall effect encoders, a reversible linear actuator such as a lead screw, or an inductive linear position sensor.

Figure 15:
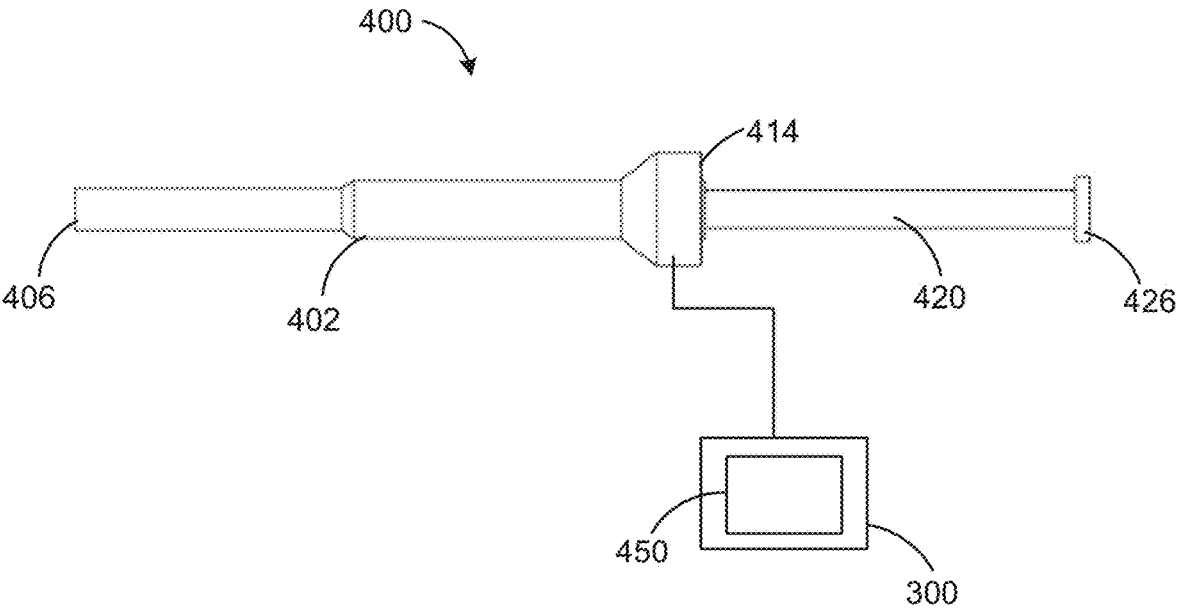
FIG. 15 illustrates the adapter of FIGS. 9A to 9D with an external computing device.

In addition, adapter 400 may include a device to supply electric power to the electrical components of adapter 400, e.g., an electric generator or battery, as well as a communication interface communicating with controller 450, described below, by any suitable means, wired or wirelessly, e.g., via Bluetooth. Although FIGS. 9A to 9D illustrate controller 450 within cavity 408 of sleeve 402, in an alternative embodiment, controller 450 and/or one or more of the other electric components of adapter 400 may be located remote from the body of adapter 400. For example, at least some of the components may be carried by an external computing device, e.g., device 300, as shown in FIG. 15.

As described in further detail below, controller 450 may execute one or more algorithms to detect a breach condition based on the measurement parameter from the surgical hand tool and/or the penetration depth measurement from depth sensor 410 of adapter 400, e.g., when changes in electrical conductivity, the depth of penetration of the elongated drilling portion, or electrical conductivity as a function of depth of penetration satisfy one or more predetermined conditions. Controller 450 may then transmit a warning signal to brake mechanism 416, e.g., upon detection of the breach condition, which is operatively coupled to plunger 420, to thereby cause brake mechanism 416 to lock plunger 420 relative to sleeve 402. For example, brake mechanism 416 may be engaged with plunger 420 via at least one of a friction plate and pads, clamping jaws, or biting teeth. As the engagement between the stopper of the surgical hand tool and abutment portion 426 of plunger 420 when the elongated drilling portion is advanced through lumen 422 of plunger 420 applies the force to plunger 420 to compress spring 418, locking plunger 420 relative to sleeve 402 upon detection of the breach via brake mechanism 416 prevents further advancement of the surgical hand tool relative to adapter 400.

Figure 10:
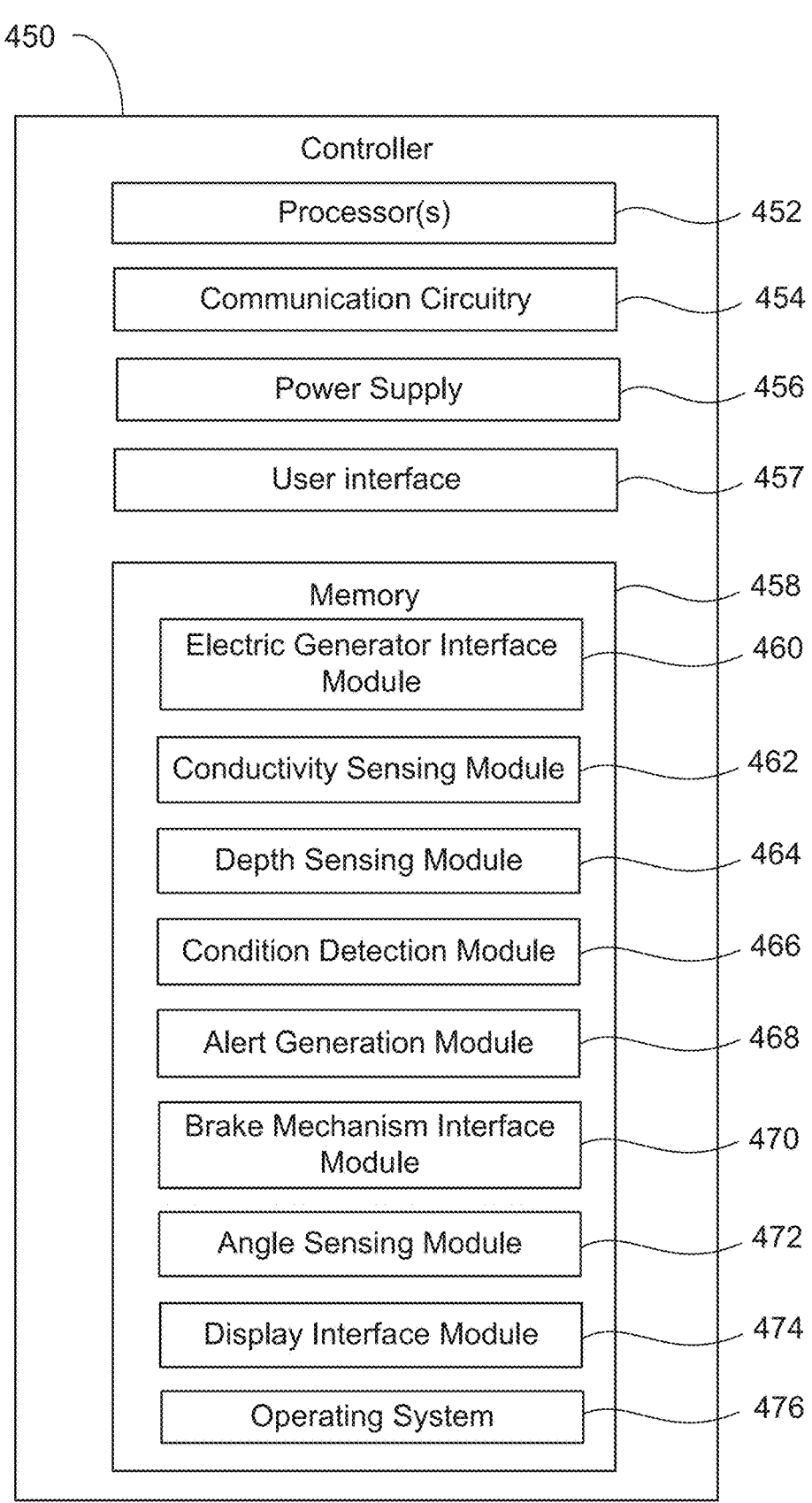
FIG. 10 is a schematic diagram of an alternative exemplary controller constructed in accordance with the principles of the present disclosure.

Referring now to FIG. 10, components that may be included in controller 450 used in conjunction with adapter 400 are described. Controller 450 may be operatively coupled to the electric components of adapter 400 and the surgical hand tool, such that controller 450 may receive signals indicative of electrical conductivity measurements from the surgical hand tool, e.g., based on electrical impedance of the surround tissue and/or bone, receive signals indicative of penetration depth measurement from depth sensor 410, detect a condition, e.g., a breach during a surgical drilling procedure, based on the signals, and instruct brake mechanism 416 to arrest advancement of the surgical hand tool relative to adapter 400 by locking plunger 420 relative to sleeve 402. Controller 450 may be disposed entirely within adapter 400, entirely within the surgical hand tool, or a combination or both adapter 400 and the surgical hand tool, or external to both adapter 400 and the surgical hand tool, e.g., in external computing device 300. Controller 450 may include one or more processors 452, communication circuitry 454, power supply 456, user interface 457, and/or memory 458.

Like memory 158, memory 458 may be RAM, ROM, Flash, or other known memory, or some combination thereof, and preferably includes storage in which data may be selectively saved. For example, programmable instructions may be stored to execute algorithms for detecting a breach or near breach of the elongated drilling portion during a surgical drilling procedure into bone. One or more electrical components and/or circuits may perform some of or all the roles of the various components described herein. Although described separately, it is to be appreciated that electrical components need not be separate structural elements. For example, controller 450 and communication circuitry 454 may be embodied in a single chip. In addition, while controller 450 is described as having memory, a memory chip(s) may be separately provided.

Controller 450 may incorporate processor 452, which may consist of one or more processors and may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. The controller also may be implemented as a combination of computing devices, e.g., a combination of a DSP and a microprocessor, a plurality of microprocessors, one or more microprocessors in conjunction with a DSP core, or any other such configuration.

Controller 450, in conjunction with firmware/software stored in the memory may execute an operating system (e.g., operating system 476), such as, for example, Windows, Mac OS, Unix or Solaris 5.10. Controller 450 also executes software applications stored in the memory. In one non-limiting embodiment, the software comprises, for example, Unix Korn shell scripts. In other embodiments, the software may be programs in any suitable programming language known to those skilled in the art, including, for example, C++, PHP, or Java.

Communication circuitry 454 may include circuitry that allows controller 450 to communicate with the electronic components of adapter 400, e.g., the electric generator, depth sensor 410, the power supply, an alarm system, and brake mechanism 416, and with the electronic components of the surgical hand tool, e.g., the electrodes, the power generator, and/or the electric processing device. Communication circuitry 454 may be configured for wired and/or wireless communication over a network such as the Internet, a telephone network, a Bluetooth network, and/or a WiFi network using techniques known in the art. Communication circuitry 144 may be a communication chip known in the art such as a Bluetooth chip and/or a WiFi chip. Communication circuitry 454 permits controller 450 to transfer information, such as signals indicative of a breach or near breach associated with spinal drilling, locally and/or to a remote location such as a server. Power supply 456 may be designed to supply power to the components of adapter 450 and/or the surgical hand tool, and may be constructed similar to power supply 156 described above.

User interface 457 may be used to receive inputs from, and/or provide outputs to, a user. For example, user interface 457 may provide information to the user on the detection of a breach or near breach during the drilling procedure, as well as information related to the penetration depth and/or angle measurement of the surgical hand tool. User interface 457 further may include an audible device and/or volume control to selectively increase or decrease an audio output. User interface 457 may include a touchscreen, switches, dials, lights, an LED, an LED matrix, other LED indicators, or other input/output devices for receiving inputs from, and/or providing outputs to, a user. In other embodiments, user interface 457 may not be present on the adapter, but is instead provided on a remote, external computing device communicatively connected to the adapter via the communication circuitry 454. User interface 457 also may be a combination of elements on the adapter and a remote computing device.

Memory 458, which is one example of a non-transitory computer-readable medium, may be used to store operating system (OS) 476, electric generator interface module 460, conductivity sensing module 462, depth sensing module 464, condition detection module 466, alert generation module 468, brake mechanism interface module 470, angle sensing nodule 472, and display interface module 474. The modules are provided in the form of computer-executable instructions that may be executed by processor 452 for performing various operations in accordance with the disclosure. Instructions may be stored, for example, for executing algorithms associated with the breach detection as described in U.S. Pat. No. 11,344,372 to Bourlion or U.S. Patent Appl. No. 2022/0361896 to Bette, the entire contents of each of which are incorporated herein by reference. Moreover, instructions may be stored for executing algorithms associated with breach detection based on changes in electrical conductivity, changes in electrical conductivity as a function of penetration depth measurement, and/or on penetration depth measurement.

Electric generator interface module 460 may be executed by processor 452 for causing the electric generator of the surgical hand tool to apply one or more voltages across the first and second contact surfaces, e.g., electrodes, of the surgical hand tool during penetration of the anatomic portion by the elongated drilling portion.

Conductivity sensing module 462 may be executed by processor 452 for receiving one or more signals from the electrodes of the surgical hand tool indicative of measured electrical conductivity as the elongated drilling portion penetrates the anatomic portion. Specifically, conductivity sensing module 462 may determine a measurement parameter related to the electrical characteristic, e.g., voltage, an intensity of the electric current, conductivity or resistivity, based on a measurement electric current(s) induced by the applied voltage(s). Accordingly, conductivity sensing module 462 may measure the electrical conductivity, e.g., based on electrical impedance of the tissue and/or bone surrounding the distal tip of the elongated drilling portion as it penetrates the anatomic portion in real-time.

Depth sensing module 464 may be executed by processor 452 for receiving one or more signals from depth sensor 410 of adapter 400, and determining the depth of penetration of the distal end of the elongated drilling portion into the anatomic portion based on the one or more signals. For example, the one or more signals may be indicative of electrical impedance of the engagement between the one or more screws of plunger 420 and band 412. Additionally or alternatively, the one or more signals may be indicative of depth as measured by at least one of a linear potentiometer, a laser distance sensor, an infrared distance sensor, an ultrasonic distance sensor, a Light Detection and Ranging (LiDAR) sensor, a 3D Time-of-Flight camera, linear magnetic or hall effect encoders, a reversible linear actuator such as a lead screw, or an inductive linear position sensor coupled to adapter 400.

Condition detection module 466 may be executed by processor 452 for detecting a condition, e.g., a breach during a surgical drilling procedure, based on signals indicative of at least one of the measured electrical conductivity by conductivity sensing module 462 and the determined depth of penetration of the elongated drilling portion of the surgical hand tool by depth sensing module 464. Specifically, condition detection module 466 may execute one or more algorithms stored therein to mathematically detect when changes in electrical conductivity, penetration depth, e.g., as the elongated drilling portion penetrates into the anatomic portion, and/or electrical conductivity as a function of depth of penetration satisfy one or more predetermined conditions. For example, based on the signals indicative of electrical conductivity and/or penetration depth measurements, condition detection module 466 may detect a breach condition such as transition to the inner layer of cortical bone delimiting the foramen, or transition to the outer layer of cortical bone near the nerve endings. A goal may be to arrest advancement of the elongated drilling portion relative to adapter 400 and the anatomic portion being penetration when rapid variations in the signals are observed, and a delay of more than one second may cause a breach at the end of drilling. Moreover, based on the signals indicative of electrical conductivity and/or penetration depth measurements, condition detection module 466 may determine that one or more additional predetermined conditions are satisfied, e.g., when a predetermined maximum depth of penetration is reached, when a predetermined depth of penetration a predetermined distance beyond the depth when a breach condition is detected is reached, e.g., 3 mm beyond the breach condition depth such that the cortex is completely perforated so that a bone screw may be inserted such that its first threads bite the cortical wall for a "bicortical fixation" technique, when a cancellous and/or cortical is reached, etc.

Alert generation module 468 may be executed by processor 452 for generating a warning signal when condition detection module 466 detects a condition, and optionally causing an alarm system operatively coupled to, e.g., adapter 400, the surgical hand tool, the sensing drill bit, and/or an external computing device carrying controller 450, to emit a warning, e.g., an audible, visual, and/or tactile warning, based on the warning signal. For example, alert generation module 468 may cause the alarm system, e.g., a speaker, to emit an audible warning signal frequency-modulated and possibly intensity-modulated, which may vary based on the change in electrical conductivity detected by condition detection module 462 or the penetration depth measurement determined by depth sensing module 464, or both. Additionally or alternatively, alert generation module 468 may cause one or more indicators to illuminate in a variety of colors, each color indicative of a predetermined range of measured electrical conductivity and/or depth of penetration, as described in further detail below with regard to FIGS. 17A and 17B.

Brake mechanism interface module 470 may be executed by processor 452 for receiving the warning signal generated by alert generation module 468, and causing brake mechanism 416 of adapter 400 to lock plunger 420 relative to sleeve 402, to thereby arrest advancement of the elongated drilling portion of the surgical hand tool relative to adapter 400 and the anatomic portion being penetrated. For example, as plunger 420 is locked relative to sleeve 402, abutment portion 426 of plunger 420 prevents the surgical hand tool from further advancement through lumen 422 of plunger 420 and lumen 404 of sleeve 402, as described in further detail below.

Angle sensing module 472 may be executed by processor 452 for receiving one or more signals from one or more angle sensors, e.g., a gravity angle sensor chip, an angular encoder, accelerometer, compass, and/or gyroscope, such as sensor 415 of adapter 400, or any other angle sensors incorporated in the surgical devices described herein (e.g., surgical drill 12, adapters 100, 100', 100", 100''', surgical hand tools 20, 30, 40, 50, sensing drill bit 500, etc.). Angle sensing module 472 may determine the angle of the associated surgical device, e.g., adapter 400, relative to the space frame and/or relative to the surface of the anatomic portion in 3D space, e.g., about the x, y, and z axes in three planes, based on the one or more signal received from the angle sensors. For example, angle sensing module 472 may calculate the angle based on the position of adapter 400 in 3D space, and not based on the position of the anatomic portion as adapter 400 is not tracked relatively to the anatomic portion, e.g., the spine. However, angle sensing module 472 may define the actual orientation of the anatomic portion, e.g., the spine or vertebrae, relative to adapter 400 during a calibration phase, e.g., at the beginning of the surgery or between each drilling procedure. For example, during the calibration phase, adapter 400 may be positioned vertically against the anatomic portion to be penetrated, e.g., a given vertebrae, while pointing one reference axis of adapter 400 in a cephalic direction, e.g., towards the head of the patient, and this orientation may be set as a reference.

In another example, during the calibration phase, adaptor 400 may be positioned along a surgeon estimated direction in space that corresponds to the local orientation of the vertebra, e.g., given from the orientation of the spinal process, or along the estimated drilling trajectory e.g., the pedicle, and this orientation may be set as a reference. Accordingly, the angle sensing module 472 may know both the space frame and the patient frame, such that angle sensing module 472 may determine the angle of adapter 400 relative to the surface of the anatomic portion. Alternatively, the reference orientation may be used by the surgeon to help match specific anatomic angles known in scientific literature, such as the vertebral pedicle convergence angle, and align the instrument according such angle. Additionally, or alternatively, the drilling orientation as well as the angles on one side of the patient may be displayed, allowing the surgeon to replicate the angles on the opposite side of the patient for subsequent drillings.

Display interface module 474 may be executed by processor 452 for rendering and transmitting data to a display operatively coupled to controller 450, e.g., disposed on user interface 457 and/or a remote computing device, for displaying information associated with the transmitted data. For example, display interface module 474 may generate or load virtual 3D models representative of one or more anatomic portions, e.g., the bone being penetrated, as well as indicators of the penetration path/angle, for display, as shown in FIG. 19A. As shown in FIG. 19A, information indicative of the angle of the penetration path, e.g., the sagittal angle and/or the axial angle, may be displayed alongside virtual 3D models of the bone and/or specific vertebrae being penetrated in real time. For example, the display may show the bone being penetrated at various angles. Moreover, display interface module 474 also may cause information indicative of the conductivity as determined by conductivity sensing module 462 and/or information indicative of the depth of penetration as determined by depth sensing module 464 to be displayed, as shown in FIGS. 19B to 19D. Moreover, display interface module 474 may cause the display to display an alert generated by alert generation module 468, e.g., when a breach is detected, as shown in FIG. 19D.

Referring now to FIGS. 11A to 11D, use of adapter 400 with an exemplary surgical hand tool is provided. Surgical hand tool 20 may be, for example, a modified straight PediGuard® device, commercially available from the assignee of the present application. As shown in FIG. 11A, surgical hand tool 20 may include handle 20 having stopper 28, and an elongated drilling portion including elongated shaft 24 and drill tip 26. Drill tip 26 may have a straight tip to facilitate penetration through an anatomic portion, e.g., tissue and/or bone. As shown in FIG. 11A, drill bit 26 may have an outer diameter that is smaller than the outer diameter of elongated shaft 24. As described above, surgical hand tool 20 may include two or more electrodes for applying voltages to induce electric currents, and electrical components for measuring electrical conductivity as drill tip 26 penetrates the anatomic portion, which may be housed within handle 22. Handle 22 is sized and shaped to be easily gripped and manually rotated by an operator, e.g., a surgeon. For example, handle 22 may be symmetric about its longitudinal axis.

Adapter 400 may be positioned against an anatomic portion such that distal end 406 of sleeve 402 presses against a surface of the anatomic portion, and lumen 404 is aligned with the desired entry point of the anatomic surface. As shown in FIG. 11B, drill tip 26 and elongated shaft 24 may be inserted through lumen 422 of plunger 420 and cavity 417 of sleeve 402. As the elongated drilling portion of surgical hand tool 20 is further advanced through 422 and cavity 417, drill tip 26 is inserted into lumen 404 of sleeve 402. In some embodiments, elongated shaft 24 also may be inserted through lumen 404 as surgical hand tool 20 is advanced through adapter 400. Alternatively, the outer diameter of elongated shaft 24 may be larger than lumen 404, such that surgical hand tool 20 may not be advanced beyond the point where the distal end of elongated shaft 24 contacts the distal end of cavity 417. Surgical hand tool 20 may be advanced through adapter 20 until stopper 28 engages with abutment portion 426 of plunger 426, at which point, further advancement of surgical hand tool 20 through adapter 400 causes spring 418 to compress and plunger 420 to advance distally within cavity 417 of sleeve 402. Depending on the length of elongated shaft 24, drill tip 26 may already be advanced beyond distal end 406 before stopper 28 engages with abutment portion 426. Surgical hand tool 20 may be further advanced and rotated such that drill tip 26 penetrates the desired anatomic portion.

As shown in FIGS. 11C and 11D, drill tip 26 may be advanced beyond distal end 406 until abutment portion 426 engages with proximal end 414 of sleeve 402. As described above, based on the measured electrical conductivity by surgical hand tool 20 and/or penetration depth measurement by adapter 400, controller 450 may cause brake mechanism 416 to lock plunger 420 relative to sleeve 402 while surgical hand tool 20 is advanced through adapter 400. For example, as described above, controller 450 may cause brake mechanism 416 to lock plunger 420 relative to sleeve 402 upon detection that one or more predetermined conditions are satisfied, e.g., when a breach condition is detected, when a maximum desired depth of penetration is reached, when a desired depth of penetration a predetermined distance beyond the depth when a breach condition is detected is reached, when a cancellous and/or cortical is reached, etc. Thus, as surgical hand tool 20 may still be rotated relative to adapter 400 when brake mechanism 416 is actuated, advancement of drill tip 26 is stopped.

Figure 12A:
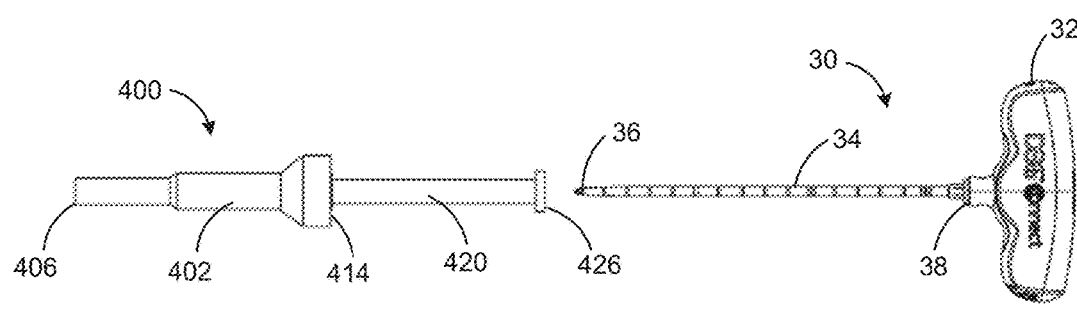
FIGS. 12A to 12D illustrate use of the adapter of FIGS. 9A to 9D with an alternative exemplary surgical hand tool in accordance with the principles of the present disclosure.

Referring now to FIGS. 12A to 12D, use of adapter 400 with another exemplary surgical hand tool is provided. Surgical hand tool 30 may be, for example, a cannulated PediGuard® device, commercially available from the assignee of the present application. As shown in FIG. 12A, surgical hand tool 30 may include handle 30 having stopper 38, and an elongated drilling portion including elongated shaft 34 and drill tip 36. Drill tip 36 may be a bevel or trocar to facilitate penetration through an anatomic portion, e.g., tissue and/or bone. Elongated shaft 34 may have a progressive diameter to ease insertion and removal. For example, elongated shaft 34 may have a graduated shaft to control the progression into bone. As described above, surgical hand tool 30 may include two or more electrodes for applying voltages to induce electric currents, and electrical components for measuring electrical conductivity as drill tip 36 penetrates the anatomic portion, which may be housed within handle 32. Handle 32 is sized and shaped to be easily gripped and manually rotated by an operator, e.g., a surgeon. For example, handle 32 may have a T-shape.

Figure 12B:
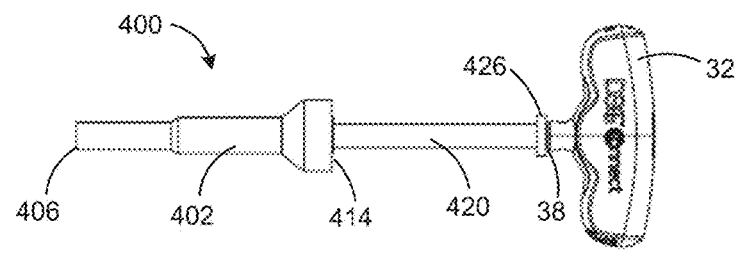

Like surgical hand tool 20, when distal end 406 of adapter 400 is positioned against the anatomic portion such that lumen 404 is aligned with the desired entry point of the anatomic surface, surgical hand tool 30 may be inserted through adapter 400. For example, drill tip 36 and elongated shaft 34 of surgical hand tool 30 may be advanced distally through lumen 422 of plunger 420 as well as cavity 417 and lumen 404 of sleeve 402 until stopper 38 engages with abutment portion 426, as shown in FIG. 12B. Depending on the length of elongated shaft 34, drill tip 36 may already be advanced beyond distal end 406. Further advancement of surgical hand tool 30 through adapter 400 causes spring 418 to compress and plunger 420 to advance distally within cavity 417, until engagement between proximal end 414 of sleeve 402 and abutment portion 426 of plunger 420 prevents further advancement of plunger 420, and accordingly, surgical hand tool 30 relative to sleeve 402.

Figure 12C:
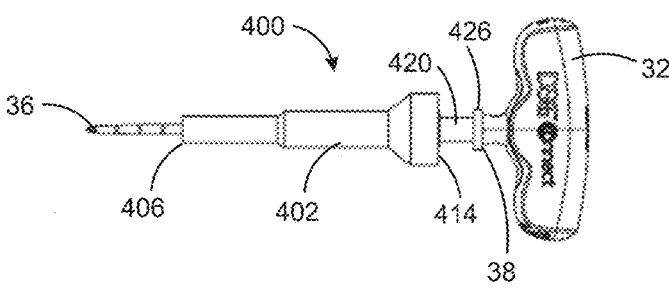
Figure 12D:
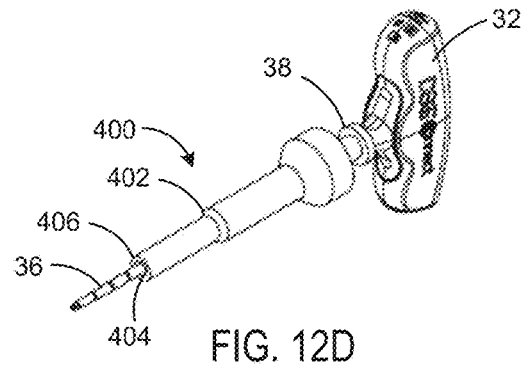

As described above, based on the measured electrical conductivity by surgical hand tool 30 and/or penetration depth measurement by adapter 400, controller 450 may cause brake mechanism 416 to lock plunger 420 relative to sleeve 402 while surgical hand tool 30 is advanced through adapter 400, e.g., before proximal end 414 of sleeve 402 engages with abutment portion 426 of plunger 420, as shown in FIGS. 12C and 12D. For example, as described above, controller 450 may cause brake mechanism 416 to lock plunger 420 relative to sleeve 402 upon detection that one or more predetermined conditions are satisfied, e.g., when a breach condition is detected, when a maximum desired depth of penetration is reached, when a desired depth of penetration a predetermined distance beyond the depth when a breach condition is detected is reached, when a cancellous and/or cortical is reached, etc. Thus, as surgical hand tool 30 may still be rotated relative to adapter 400 when brake mechanism 416 is actuated, advancement of drill tip 36 is stopped.

Figure 13A:
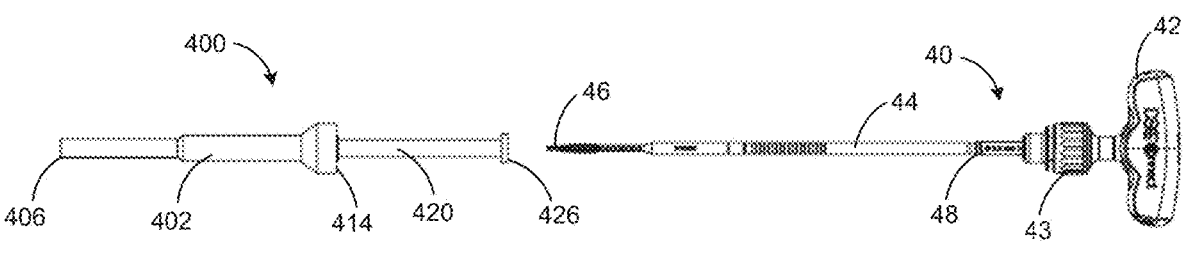
FIGS. 13A to 13D illustrate use of the adapter of FIGS. 9A to 9D with another alternative exemplary surgical hand tool in accordance with the principles of the present disclosure.

Referring now to FIGS. 13A to 13D, use of adapter 400 with another exemplary surgical hand tool is provided. Surgical hand tool 40 may be, for example, a threaded PediGuard® device, commercially available from the assignee of the present application. As shown in FIG. 13A, surgical hand tool 40 may include handle 40 operatively coupled to an elongated drilling portion including elongated shaft 44 and drill tip 46, via actuator 43. Elongated shaft 44 may include stopper 48. Drill tip 46 may have a threaded surface to facilitate penetration through an anatomic portion, e.g., tissue and/or bone. As shown in FIG. 13A, stopper 48 may be formed on elongated shaft 44, e.g., at a point where the outer diameter of elongated shaft 44 increases in a direction toward handle 42.

As described above, surgical hand tool 40 may include two or more electrodes for applying voltages to induce electric currents, and electrical components for measuring electrical conductivity as drill tip 46 penetrates the anatomic portion, which may be housed within handle 42. Handle 42 is sized and shaped to be easily gripped and manually rotated by an operator, e.g., a surgeon. For example, handle 42 may have a T-shape. Actuator 43 may be actuated between an unlocked state where rotation of handle 42 in a first direction causes rotation of the elongated drilling portion in the first direction, but rotation of handle 42 in an opposite direction does not cause rotation of the elongated drilling portion, and a locked state where rotation of handle 42 in a first direction causes rotation of the elongated drilling portion in the first direction, and rotation of handle 42 in the opposite direction causes rotation of the elongated drilling portion in the opposite direction.

Figure 13B:
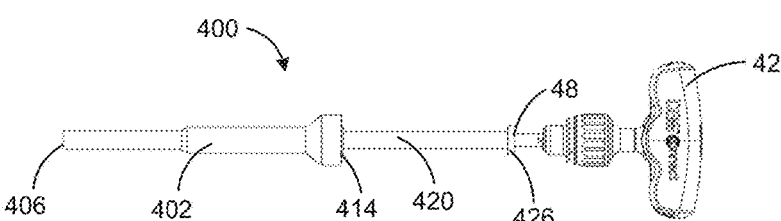

Like surgical hand tools 20, 30, when distal end 406 of adapter 400 is positioned against the anatomic portion such that lumen 404 is aligned with the desired entry point of the anatomic surface, surgical hand tool 40 may be inserted through adapter 400. For example, drill tip 46 and elongated shaft 44 of surgical hand tool 40 may be advanced distally through lumen 422 of plunger 420 as well as cavity 417 and lumen 404 of sleeve 402 until stopper 48 engages with abutment portion 426, as shown in FIG. 13B. Depending on the length of elongated shaft 44, drill tip 46 may already be advanced beyond distal end 406. Further advancement of surgical hand tool 40 through adapter 400 causes spring 418 to compress and plunger 420 to advance distally within cavity 417, until engagement between proximal end 414 of sleeve 402 and abutment portion 426 of plunger 420 prevents further advancement of plunger 420, and accordingly, surgical hand tool 40 relative to sleeve 402.

Figure 13C:
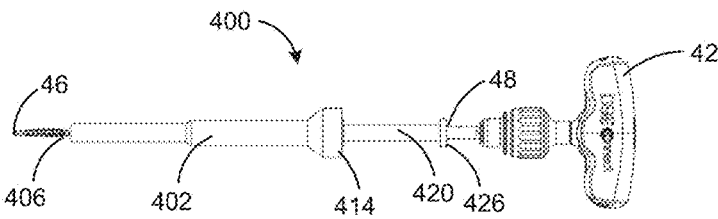
Figure 13D:
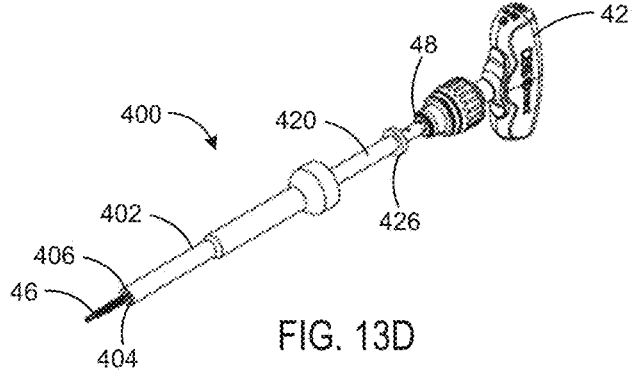

As described above, based on the measured electrical conductivity by surgical hand tool 40 and/or penetration depth measurement by adapter 400, controller 450 may cause brake mechanism 416 to lock plunger 420 relative to sleeve 402 while surgical hand tool 40 is advanced through adapter 400, e.g., before proximal end 414 of sleeve 402 engages with abutment portion 426 of plunger 420, as shown in FIGS. 13C and 13D. For example, as described above, controller 450 may cause brake mechanism 416 to lock plunger 420 relative to sleeve 402 upon detection that one or more predetermined conditions are satisfied, e.g., when a breach condition is detected, when a maximum desired depth of penetration is reached, when a desired depth of penetration a predetermined distance beyond the depth when a breach condition is detected is reached, when a cancellous and/or cortical is reached, etc. Thus, as surgical hand tool 40 may still be rotated relative to adapter 400 when brake mechanism 416 is actuated, advancement of drill tip 46 is stopped.

Figure 14A:
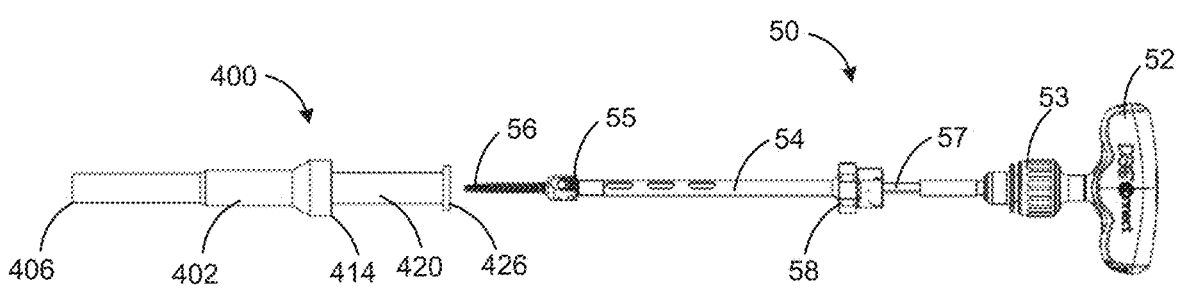
FIGS. 14A to 14D illustrate use of the adapter of FIGS. 9A to 9D with yet another alternative exemplary surgical hand tool in accordance with the principles of the present disclosure.

Referring now to FIGS. 14A to 14D, use of adapter 400 with another exemplary surgical hand tool is provided. Surgical hand tool 50 may be, for example, a DSG® smart screw device, commercially available from the assignee of the present application. As shown in FIG. 14A, surgical hand tool 50 may include handle 50 operatively coupled to inner elongated shaft 57 via actuator 53, and outer elongated shaft 54 rotatably disposed over at least a portion of inner elongated shaft 57. A proximal end of outer elongated shaft 54 may include stopper 58, and a distal end of outer elongated shaft 54 may be removably coupled to implantable drill tip 56 via connection 55, e.g., a threaded connection. Handle 52 is sized and shaped to be easily gripped and manually rotated by an operator, e.g., a surgeon. For example, handle 52 may have a T-shape. Actuator 53 may be actuated between an unlocked state where rotation of handle 52 in a first direction causes rotation of inner elongated shaft 57, and accordingly outer elongated shaft 54 and drill tip 56, in the first direction, but rotation of handle 52 in an opposite direction does not cause rotation of inner elongated shaft 57, and a locked state where rotation of handle 52 in a first direction causes rotation of inner elongated shaft 57, and accordingly outer elongated shaft 54 and drill tip 56, in the first direction, and rotation of handle 52 in the opposite direction causes rotation of inner elongated shaft 57, and accordingly outer elongated shaft 54 and drill tip 56, in the opposite direction. Stopper 58 may be actuated, e.g., rotated relative to inner elongated shaft 57, to cause the threaded distal end of outer elongated shaft 54 to engage or disengage threaded connection 55 of drill tip 56.

As described above, surgical hand tool 50 may include two or more electrodes for applying voltages to induce electric currents, and electrical components for measuring electrical conductivity as drill tip 56 penetrates the anatomic portion, which may be housed within handle 52. Drill tip 56 may have a threaded surface to facilitate penetration through an anatomic portion, e.g., tissue and/or bone, and further may include at least some of the electrical components, e.g., one or more electrodes, for measuring electrical conductivity. Accordingly, drill tip 56 may be electrically coupled to the electrical components of surgical hand tool 50, such that drill tip 56 may transmit signals therebetween.

Figure 14B:
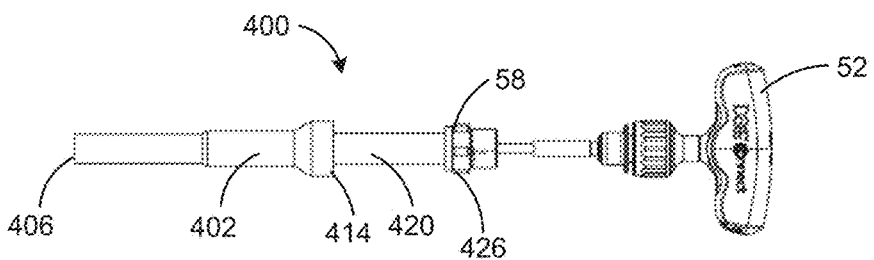

Like surgical hand tools 20, 30, 40, when distal end 406 of adapter 400 is positioned against the anatomic portion such that lumen 404 is aligned with the desired entry point of the anatomic surface, surgical hand tool 50 may be inserted through adapter 400. For example, drill tip 56, outer elongated shaft 54, and inner elongated shaft 57 of surgical hand tool 50 may be advanced distally through lumen 422 of plunger 420 as well as cavity 417 and lumen 404 of sleeve 402 until stopper 58 engages with abutment portion 426, as shown in FIG. 14B. Depending on the length of outer elongated shaft 54 and inner elongated shaft 57, drill tip 56 may already be advanced beyond distal end 406. Further advancement of surgical hand tool 50 through adapter 400 causes spring 418 to compress and plunger 420 to advance distally within cavity 417, until engagement between proximal end 414 of sleeve 402 and abutment portion 426 of plunger 420 prevents further advancement of plunger 420, and accordingly, surgical hand tool 50 relative to sleeve 402.

Figure 14C:
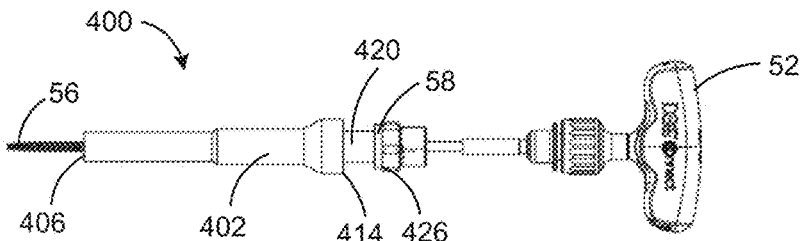
Figure 14D:
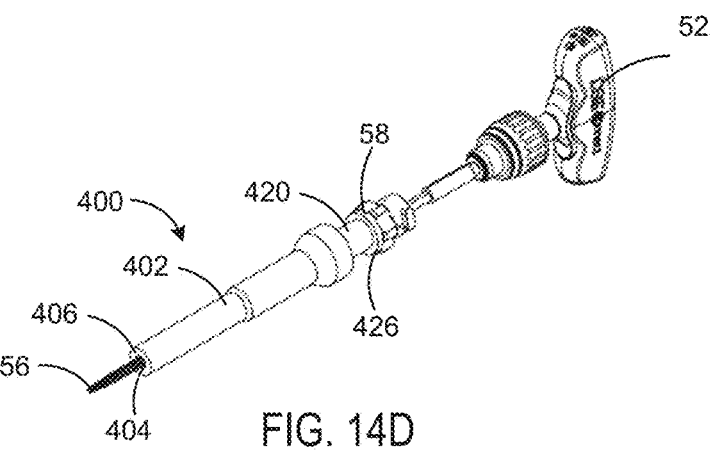

As described above, based on the measured electrical conductivity by surgical hand tool 50 and/or penetration depth measurement by adapter 400, controller 450 may cause brake mechanism 416 to lock plunger 420 relative to sleeve 402 while surgical hand tool 50 is advanced through adapter 400, e.g., before proximal end 414 of sleeve 402 engages with abutment portion 426 of plunger 420, as shown in FIGS. 14C and 14D. For example, as described above, controller 450 may cause brake mechanism 416 to lock plunger 420 relative to sleeve 402 upon detection that one or more predetermined conditions are satisfied, e.g., when a breach condition is detected, when a maximum desired depth of penetration is reached, when a desired depth of penetration a predetermined distance beyond the depth when a breach condition is detected is reached, when a cancellous and/or cortical is reached, etc. Thus, as surgical hand tool 50 may still be rotated relative to adapter 400 when brake mechanism 416 is actuated, advancement of drill tip 56 is stopped.

Referring now to FIG. 15, in some alternative embodiments, adapter 400 and/or the surgical hand tool may be operatively coupled to an external computing device, e.g., external computing device 300. For example, controller 450 may be disposed in external computing device 300, as opposed to within adapter 400 and/or the surgical hand tool. Accordingly, controller 450 may be operatively coupled to the electronic components of adapter 400 and/or the surgical hand tool via a wired connection, e.g., one or more cables, or a wireless connection, e.g., Bluetooth connection. In addition, power supply 456 may be positioned in external computing device 300 for powering the electronic components of adapter 400 and/or the surgical hand tool. In some embodiments, external computing device 300 may include a display screen for displaying information regarding the measured electrical conductivity, the penetration depth measurement, the measured electrical conductivity as a function of depth of penetration of the surgical hand tool, the angle measurement, and/or a visual warning message if a condition is detected, as described above.

Referring now to FIGS. 16A to 16E, use of adapter 400 with conventional surgical drill 12 via an exemplary sensing drill bit is provided. As described above, surgical drill 12 may be any conventional surgical drill configured to receive and transmit rotary motion to a drill bit. Accordingly, surgical drill 12 may be configured to receive and transmit rotary motion to sensing drill bit 500 having an integrated drill bit, which may be used in conjunction with adapter 400 for arresting advancement of sensing drill bit 500 and surgical drill 12 relative to adapter 400 and the anatomic portion being penetrated, e.g., when changes in electrical conductivity and/or the depth of penetration detected by sensing drill bit 500 indicates a breach condition.

Figure 16A:
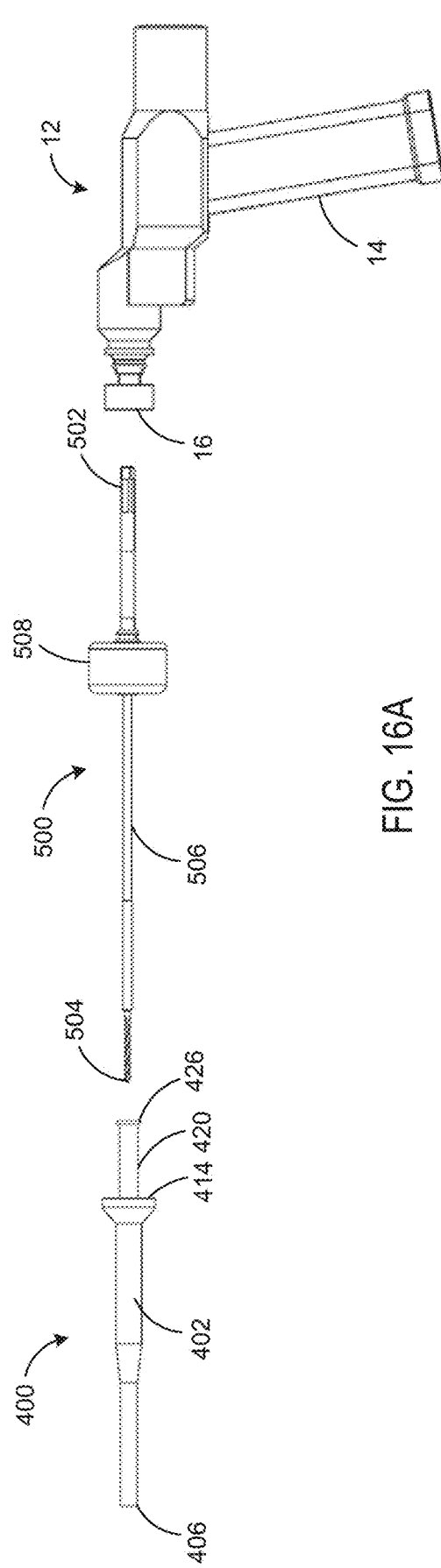
Figure 16B:
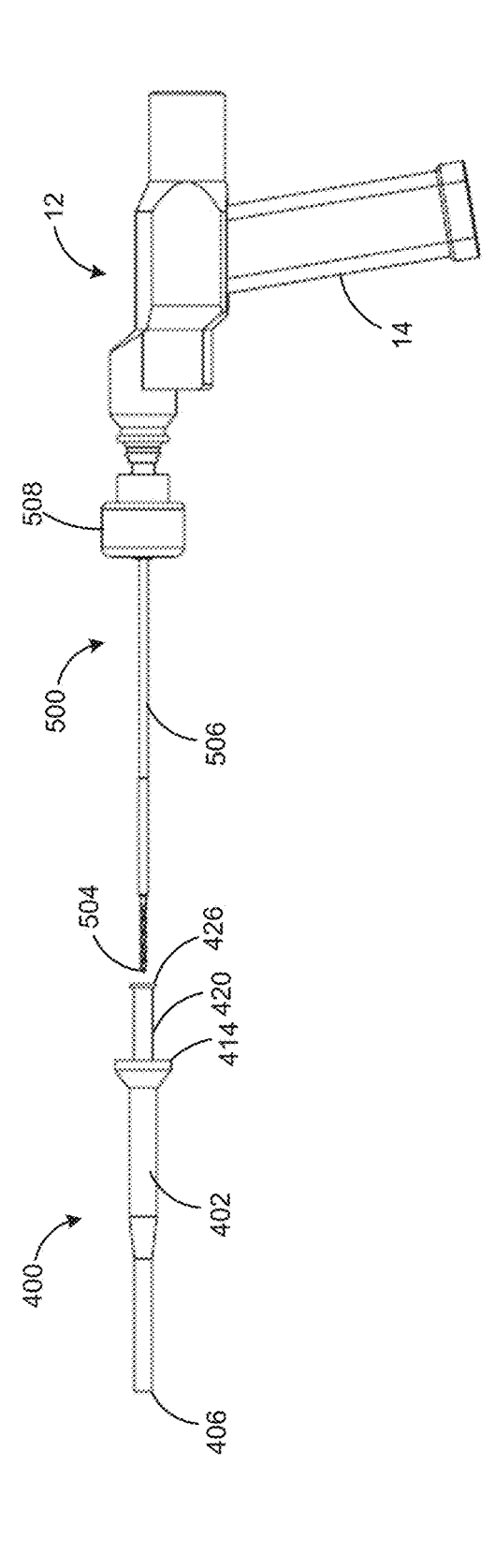

As shown in FIG. 16A, sensing drill bit 500 may include proximal end 502 sized and shaped to be received by surgical drill 12, e.g., chuck 16 of surgical drill 12, as shown in FIG. 16B. Sensing drill bit 500 further may include distal end 504 having an integrated drill bit tip configured to contact and penetrate, e.g., tissue and/or bone, and elongate shaft 506 extending between proximal end 502 and distal end 504. Distal end 504 of sensing drill bit 500 may be constructed similar to conductivity-sensing drill bit 200, such that sensing drill bit 500 may sense electrical characteristics of tissue and/or bone as it moves within an anatomic portion. For example, distal end 504 may include two or more electrodes for applying voltages to induce electric currents for measuring electrical conductivity. Moreover, sensing drill bit 500 may generate one or more signals indicative of the sensed electrical characteristics for transmission to, e.g., conductivity sensing module 462 of controller 450 of adapter 400, such that adapter 400 may arrest advancement of sensing drill bit 500 and surgical drill 12 relative to adapter 400, as described above.

Accordingly, sensing drill bit 500 may include hub 508 sized and shaped to house the electric components electrically coupled to distal end 504 for measuring electrical conductivity as distal end 504 penetrates the anatomic portion. Moreover, the electronic components of sensing drill bit 500 may be in electrical communication with controller 450 of adapter 400 for transmission of data therebetween. In some embodiments, sensing drill bit 500 may include a sensor for measuring the angle of sensing drill bit 500 relative to the surface of the tissue or bone during penetration, e.g., a gravity angle sensor chip, an accelerometer, and/or gyroscope. Such an angle sensor may be disposed within hub 508 or cavity 408 of adapter 400, or both. As shown in FIG. 16A, hub 508 may be disposed between elongated shaft 506 and proximal end 502. Moreover, hub 508 may have an outer diameter larger than abutment portion 426 of plunger 420 of adapter 400, such that as distal end 504 of sensing drill bit 500 is inserted through adapter 400, as shown in 16C, hub 508 may engage with abutment portion 426 as plunger 420 advances distally through cavity 417 of adaptor 400.

Like surgical hand tools 20, 30, 40, 50, when distal end 406 of adapter 400 is positioned against the anatomic portion such that lumen 404 is aligned with the desired entry point of the anatomic surface, sensing drill bit 500 coupled to surgical drill 12 may be inserted through adapter 400. For example, distal end 504 and elongated shaft 506 of sensing drill bit 500 may be advanced distally through lumen 422 of plunger 420 as well as cavity 417 and lumen 404 of sleeve 402 until hub 508 engages with abutment portion 426, as shown in FIG. 16C. Depending on the length of elongated shaft 506, distal end 504 may already be advanced beyond distal end 406. Further advancement of sensing drill bit 500 via surgical drill 12 through adapter 400 causes spring 418 to compress and plunger 420 to advance distally within cavity 417, until engagement between proximal end 414 of sleeve 402 and abutment portion 426 of plunger 420 prevents further advancement of plunger 420, and accordingly, sensing drill bit 500 and surgical drill 12 relative to sleeve 402, as shown in FIG. 16D.

As described above, based on the measured electrical conductivity by sensing drill bit 500 and/or penetration depth measurement by adapter 400, controller 450 may cause brake mechanism 416 to lock plunger 420 relative to sleeve 402 while sensing drill bit 500 is advanced through adapter 400, e.g., before proximal end 414 of sleeve 402 engages with abutment portion 426 of plunger 420, as shown in FIGS. 16D and 16E. For example, as described above, controller 450 may cause brake mechanism 416 to lock plunger 420 relative to sleeve 402 upon detection that one or more predetermined conditions are satisfied, e.g., when a breach condition is detected, when a maximum desired depth of penetration is reached, when a desired depth of penetration a predetermined distance beyond the depth when a breach condition is detected is reached, when a cancellous and/or cortical is reached, etc. Thus, as surgical drill 12 may continue to transmit rotary motion to sensing drill bit 500 such that sensing drill bit 500 rotates relative to adapter 400 when brake mechanism 416 is actuated, advancement of distal end 504 is stopped.

Referring now to FIGS. 17A to 17J, alternative exemplary hubs of the sensing drill bit is provided. As described above, hub 508 may be sized and shaped to house the electric components of sensing drill bit 500, e.g., the electric components electrically coupled to distal end 504 for measuring electrical conductivity as distal end 504 penetrates the anatomic portion, a sensor for measuring the angle of sensing drill bit 500 relative to the surface of the tissue or bone during penetration, e.g., a gravity angle sensor chip, an accelerometer, and/or gyroscope, and/or communication circuitry in electrical communication with controller 450 of adapter 400 for transmission of data therebetween. As shown in FIGS. 17A to 17J, hub 508 further may include one or more indicators, e.g., LED lights, each indicator configured to illuminate in one or more colors to thereby indicate a range of electrical conductivity measured during penetration by the sensing drill bit. In some embodiments, each indicator may be configured to illuminate in one or more colors to thereby indicate a range of depth penetration by the sensing drill bit.

Figure 17A:
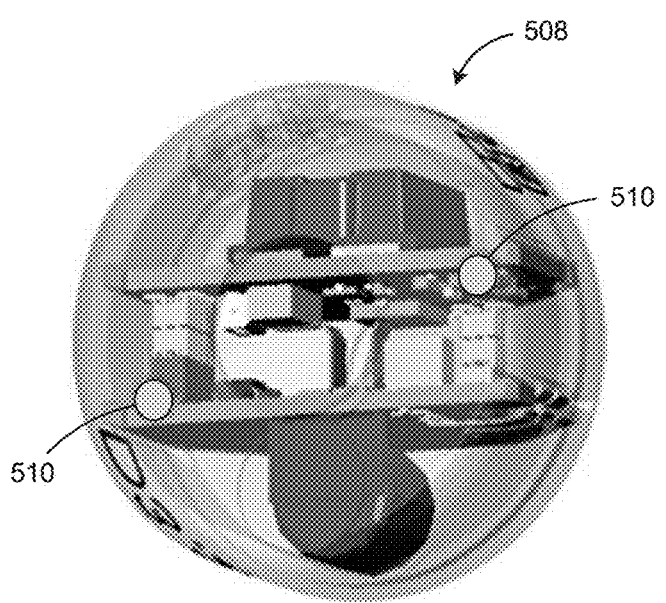
FIGS. 17A to 17J illustrate an alternative exemplary hub of the sensing drill bit of FIGS. 16A to 16E constructed in accordance with the principles of the present disclosure.
Figure 17A:
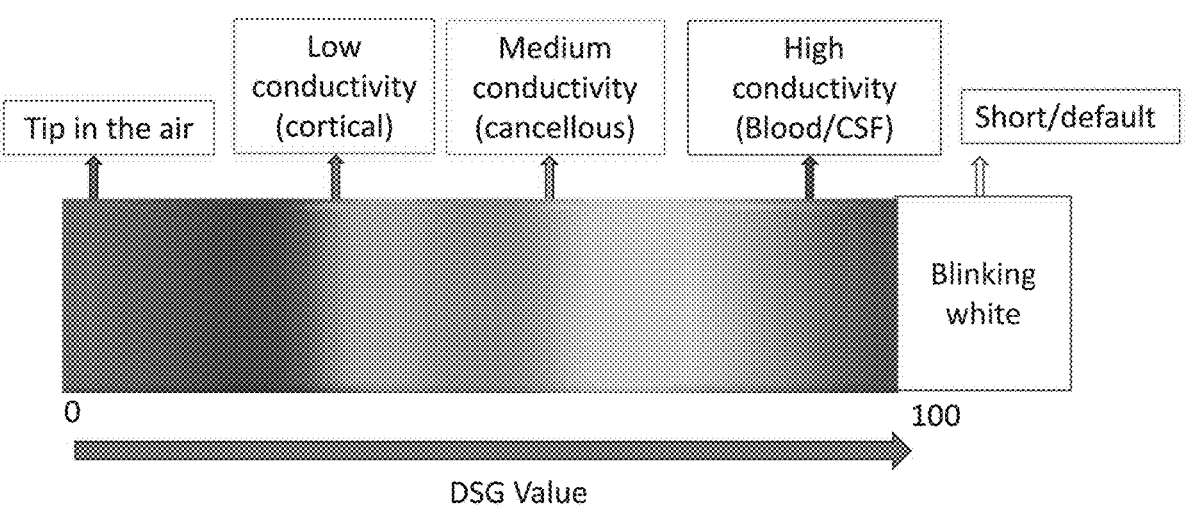

For example, as shown in FIG. 17A, hub 508 may include one or more indicators 510, e.g., LED lights, disposed on the backside of hub 508, e.g., the side of 508 observable by the user during operation. Indicators 510 may illuminate in a variety of colors, each color indicative of a range of electrical conductivity measured during penetration by the sensing drill bit and/or a range of depth penetration by the sensing drill bit. Accordingly, as hub 508 rotates along with sensing drill bit 500, e.g., via actuation of surgical drill 12, the illuminated colors of indicators 510 may be readily observable by the user. For example, as shown in FIG. 17A, indicators 510 may illuminate in a first color, e.g., purple, when the tip of the sensing drill bit is not in contact with bone/tissue, indicating that the tip of the sensing drill bit is in the air, a second color, e.g., blue, when the sensing drill bit measures a first predetermined range of electrical conductivity (e.g., low conductivity) and/or the measured depth of penetration is within a first predetermined depth range, indicating that the tip of the sensing drill bit is in a cortical, a third color, e.g., green, when the sensing drill bit measures a second predetermined range of electrical conductivity higher than the first predetermined range of electrical conductivity (e.g., medium conductivity) and/or the measured depth of penetration is within a second predetermined depth range greater than the first depth range, indicating that the tip of the sensing drill bit is in a cancellous bone, a fourth color, e.g., red, when the sensing drill bit measures a third predetermined range of electrical conductivity higher than the second predetermined range of electrical conductivity (e.g., high conductivity) and/or the measured depth of penetration is within a third predetermined depth range greater than the second depth range, indicating that the tip of the sensing drill bit is in blood, cerebral spinal fluid, or soft tissue, and a fourth color, e.g., blinking white, indicative of a short/default. As will be understood by a person having ordinary skill in the art, indicators 510 may illuminate in different colors, and each color may be indicative of a different and/or combination of the ranges of electrical conductivity and/or depths of penetration described above. For example, in one embodiment, indicators 510 may illuminate in a first color, e.g., green, when the sensing drill bit measures a first predetermined range of electrical conductivity (e.g., low to medium conductivity) and/or the measured depth of penetration is within a first predetermined depth range, indicating that the tip of the sensing drill bit is in a cortical or cancellous bone.

Figure 17B:
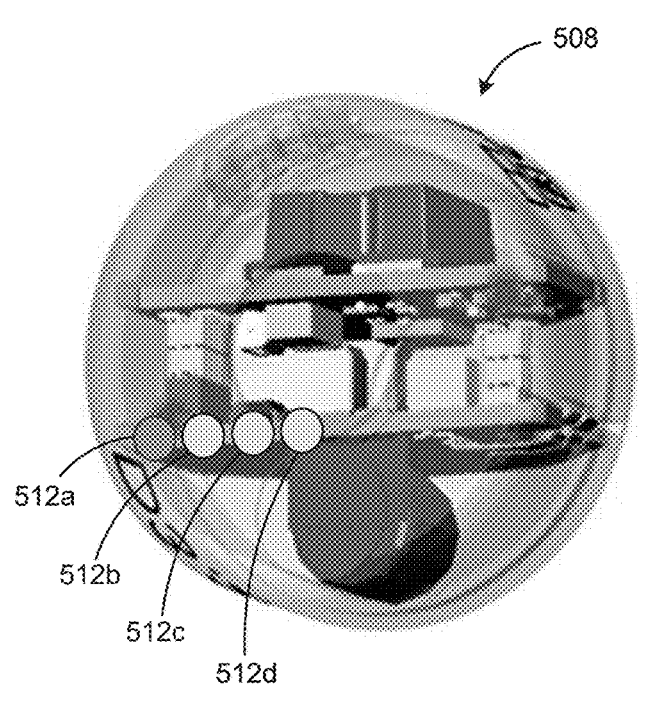
Figure 17C:
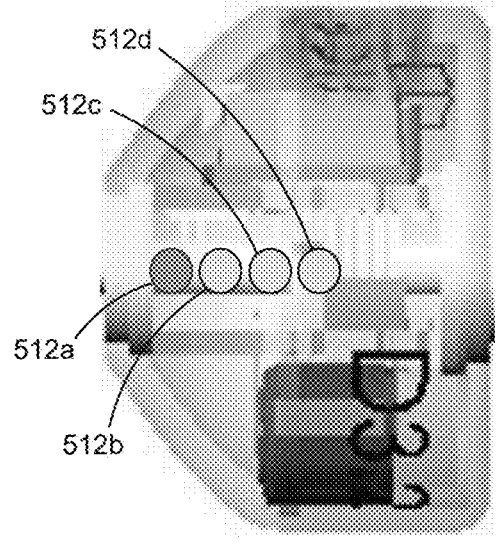

As shown in FIG. 17B, hub 508 may include a plurality of indicators, e.g., indicators 512a, 512b, 512c, 512d, disposed on the backside of hub 508. Indicators 512a, 512b, 512c, 512d may be independently configured to illuminate in the same color, e.g., green. In addition, the number of indicators that are illuminated may be indicative of the range of electrical conductivity measured during penetration by the sensing drill bit and/or the range of depth penetration by the sensing drill bit. For example, only indicator 512a may be illuminated to indicate low conductivity measured by the sensing drill bit during penetration, only indicators 512a, 512b may be illuminated to indicate medium conductivity measured by the sensing drill bit during penetration, only indicators 512a, 512b, 512c may be illuminated to indicate high conductivity measured by the sensing drill bit during penetration, and all of indicators 512a, 512b, 512c, 512d may be illuminated to indicate very high conductivity measured by the sensing drill bit during penetration. As will be understood by a person having ordinary skill in the art, more or less than four indicators may be used to indicate the range of electrical conductivity measured by the sensing drill bit during penetration. Additionally or alternatively, as shown in FIG. 17C, indicators 512a, 512b, 512c, 512d may be disposed on the lateral surface of hub 508, e.g., in a direction parallel with the longitudinal axis of hub 508, such that, during rotation of hub 508, the intensity of illumination via indicators 512a, 512b, 512c, 512d may be readily observable by the user.

Figure 17D:
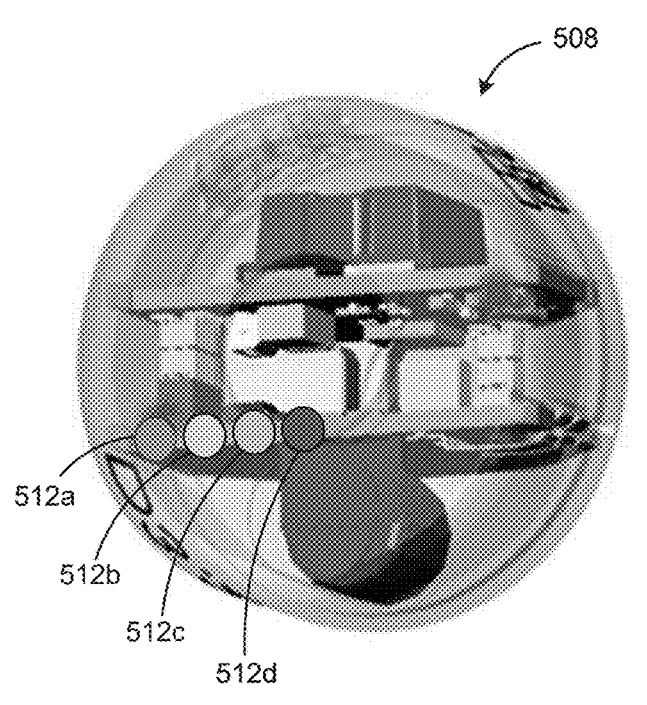
Figure 17E:
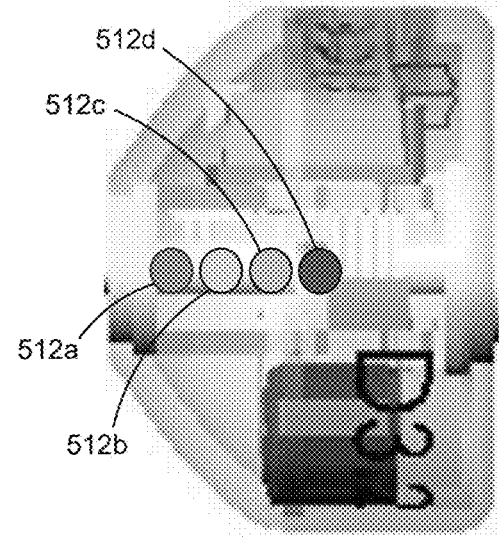

As shown in FIGS. 17D and 17E, each of indicators 512a, 512b, 512c, 512d may be configured to illuminate in a unique color, to thereby indicate the range of electrical conductivity measured by the sensing drill bit during penetration. For example, indicator 512a may be configured to illuminate in a first color, e.g., green, indicator 512b may be configured to illuminate in a second color, e.g., yellow, indicator 512c may be configured to illuminate in a third color, e.g., orange, and indicator 512d may be configured to illuminate in a fourth color, e.g., red. Accordingly, only indicator 512a may be illuminated (e.g., green) to indicate low conductivity measured by the sensing drill bit during penetration, only indicators 512a, 512b may be illuminated (e.g., green and yellow) to indicate medium conductivity measured by the sensing drill bit during penetration, only indicators 512a, 512b, 512c may be illuminated (e.g., green, yellow, and orange) to indicate high conductivity measured by the sensing drill bit during penetration, and all of indicators 512a, 512b, 512c, 512d may be illuminated (e.g., green, yellow, orange, and red) to indicate very high conductivity measured by the sensing drill bit during penetration. As will be understood by a person having ordinary skill in the art, more or less than four indicators may be used to indicate the range of electrical conductivity measured by the sensing drill bit during penetration. As shown in FIG. 17D, indicators 512a, 512b, 512c, 512d may be disposed on the backside of hub 508. Additionally or alternatively, indicators 512a, 512b, 512c, 512d may be disposed on the lateral surface of hub 508, as shown in FIG. 17E.

Figure 17F:
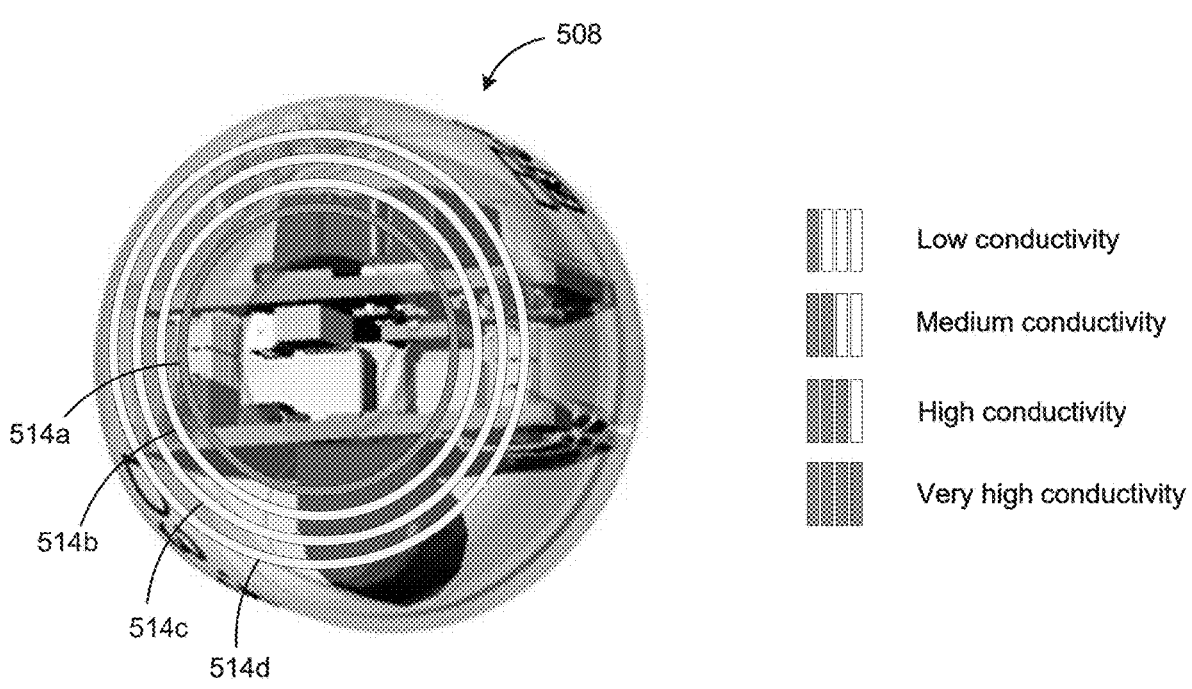
Figure 17G:
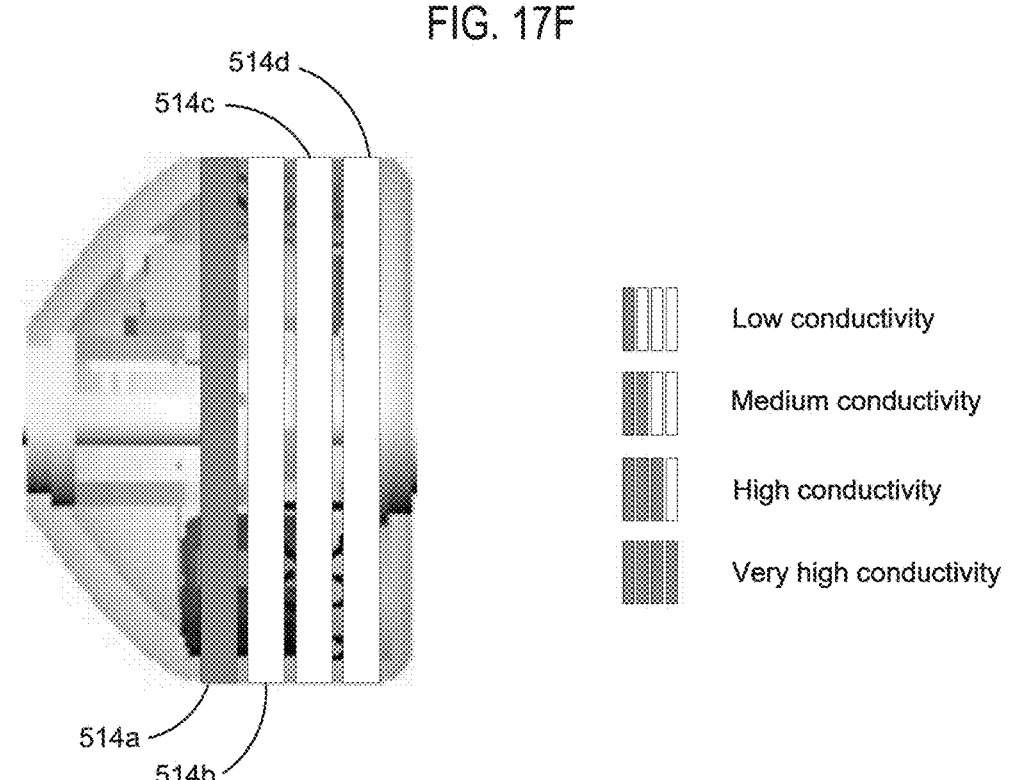

As shown in FIG. 17F, hub 508 may include a plurality of ring-shaped indicators, e.g., indicators 514a, 514b, 514c, 514d, disposed on the backside of hub 508. For example, indicators 514a, 514b, 514c, 514d may be coaxial with each other, such that indicator 514b has a larger diameter than indicator 514a, indicator 514c has a larger diameter than indicator 514b, and indicator 514d has a larger diameter than indicator 514c. Like indicators 512a, 512b, 512c, 512d, of FIGS. 17B and 17C, indicators 514a, 514b, 514c, 514d may be independently configured to illuminate in the same color, e.g., green. Accordingly, the number of indicators that are illuminated may be indicative of the range of electrical conductivity measured during penetration by the sensing drill bit and/or the range of depth penetration by the sensing drill bit. For example, only indicator 514a may be illuminated to indicate low conductivity measured by the sensing drill bit during penetration, only indicators 514a, 514b may be illuminated to indicate medium conductivity measured by the sensing drill bit during penetration, only indicators 514a, 514b, 514c may be illuminated to indicate high conductivity measured by the sensing drill bit during penetration, and all of indicators 514a, 514b, 514c, 514d may be illuminated to indicate very high conductivity measured by the sensing drill bit during penetration. As will be understood by a person having ordinary skill in the art, more or less than four indicators may be used to indicate the range of electrical conductivity measured by the sensing drill bit during penetration. Additionally or alternatively, as shown in FIG. 17G, indicators 514a, 514b, 514c, 514d may be disposed on the lateral surface of hub 508, e.g., in a direction parallel with the longitudinal axis of hub 508, such that, during rotation of hub 508, the intensity of illumination via indicators 514a, 514b, 514c, 514d may be readily observable by the user.

Figure 17H:
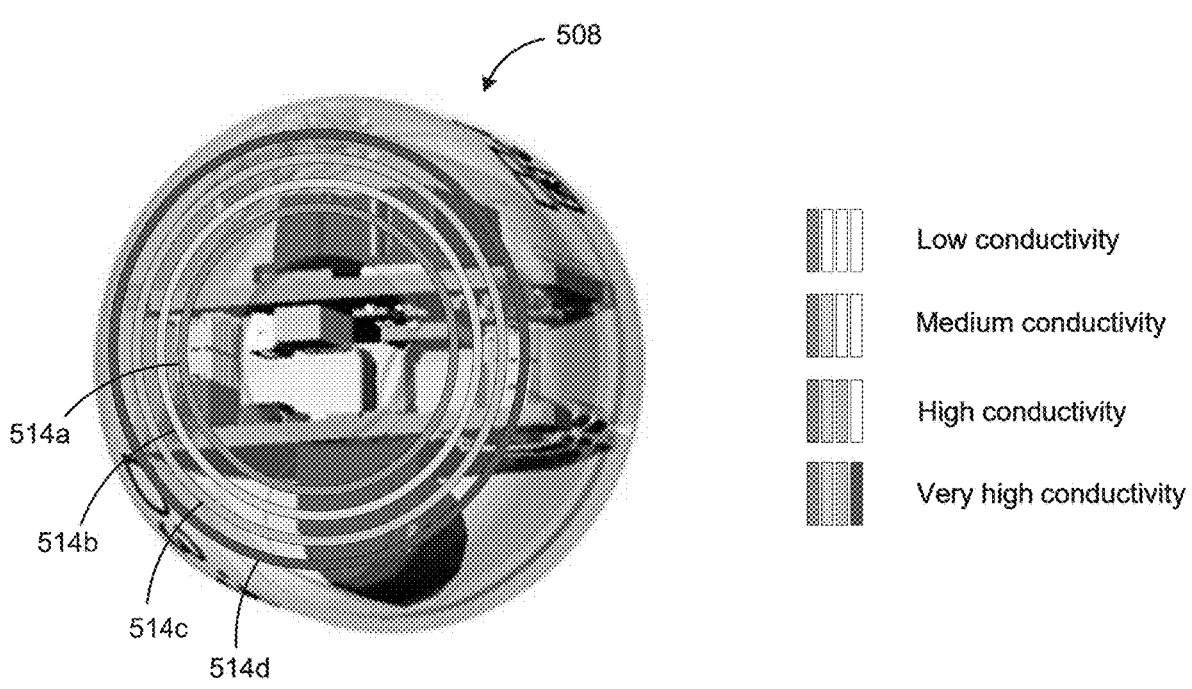
Figure 17I:
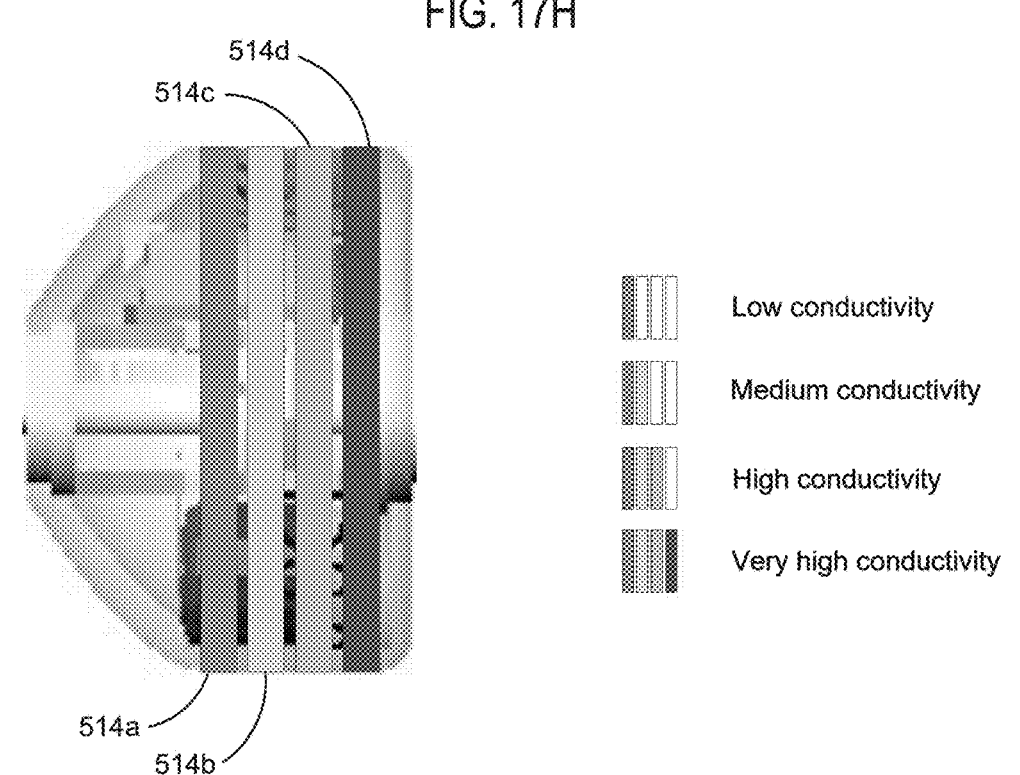

As shown in FIGS. 17H and 17I, like indicators 512a, 512b, 512c, 512d, of FIGS. 17D and 17E, each of ring-shaped indicators 514a, 514b, 514c, 514d may be configured to illuminate in a unique color, to thereby indicate the range of electrical conductivity measured by the sensing drill bit during penetration. For example, indicator 514a may be configured to illuminate in a first color, e.g., green, indicator 514b may be configured to illuminate in a second color, e.g., yellow, indicator 514c may be configured to illuminate in a third color, e.g., orange, and indicator 514d may be configured to illuminate in a fourth color, e.g., red. Accordingly, only indicator 514a may be illuminated (e.g., green) to indicate low conductivity measured by the sensing drill bit during penetration, only indicators 514a, 514b may be illuminated (e.g., green and yellow) to indicate medium conductivity measured by the sensing drill bit during penetration, only indicators 514a, 514b, 514c may be illuminated (e.g., green, yellow, and orange) to indicate high conductivity measured by the sensing drill bit during penetration, and all of indicators 514a, 514b, 514c, 514d may be illuminated (e.g., green, yellow, orange, and red) to indicate very high conductivity measured by the sensing drill bit during penetration. As will be understood by a person having ordinary skill in the art, more or less than four indicators may be used to indicate the range of electrical conductivity measured by the sensing drill bit during penetration. As shown in FIG. 17H, indicators 514a, 514b, 514c, 514d may be disposed on the backside of hub 508. Additionally or alternatively, indicators 514a, 514b, 514c, 514d may be disposed on the lateral surface of hub 508, as shown in FIG. 17I.

Figure 17J:
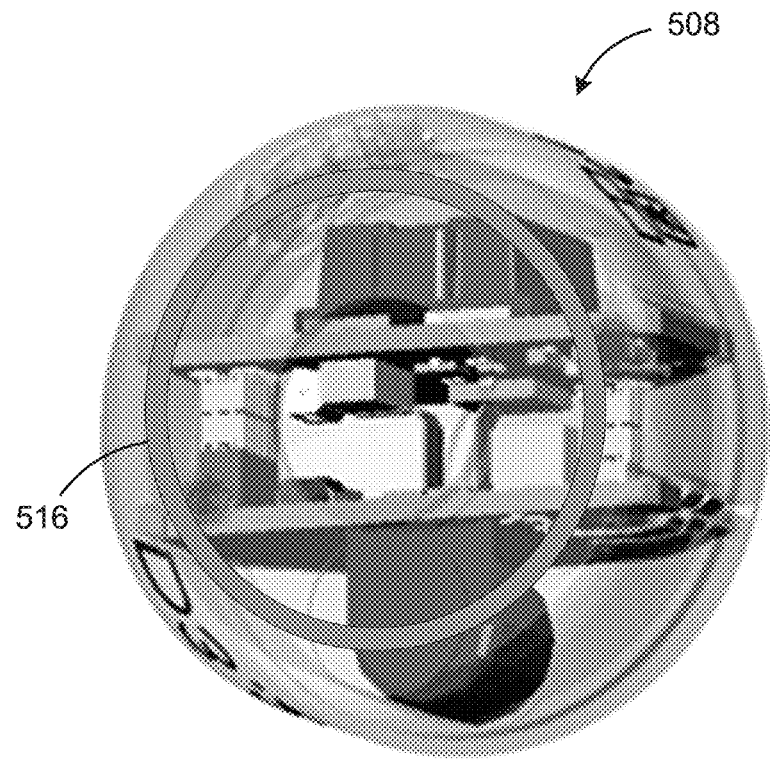

As shown in FIG. 17J, hub 508 may include a single ring-shaped indicator, e.g., indicator 516, disposed on the lateral surface of hub 508. Indicator 516 may be configured to illuminate in one or more colors, in a blinking manner with a pitch and cadence corresponding to the audio alert indicative of the range of electrical conductivity measured during penetration by the sensing drill bit and/or the range of depth penetration by the sensing drill bit, as described above. For example, the frequency of blinking of indicator 516 may increase as electrical conductivity measured by the sensing drill bit increases.

Figure 18A:
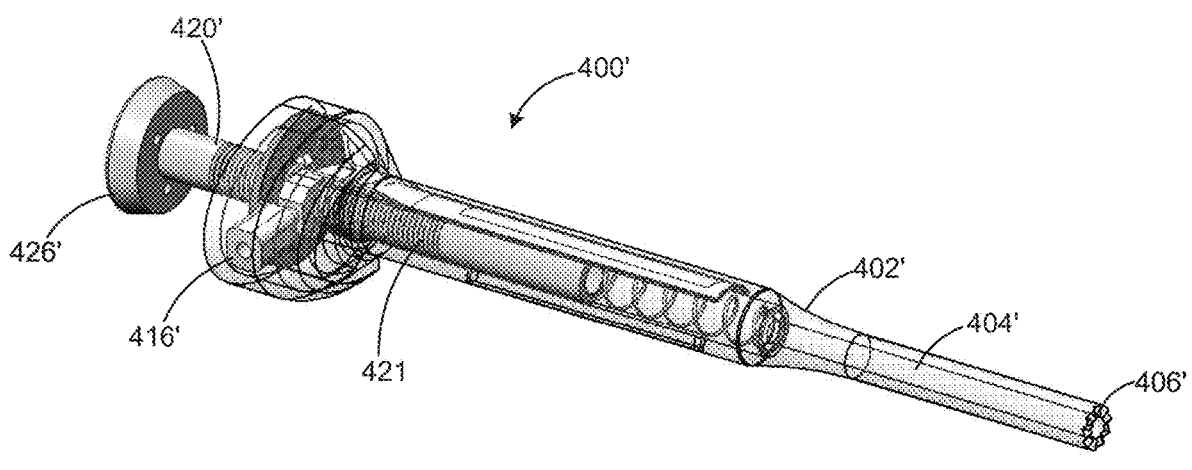
FIG. 18A illustrates an alternative exemplary adapter constructed in accordance with the principles of the present disclosure.
Figures 18B, 18C:
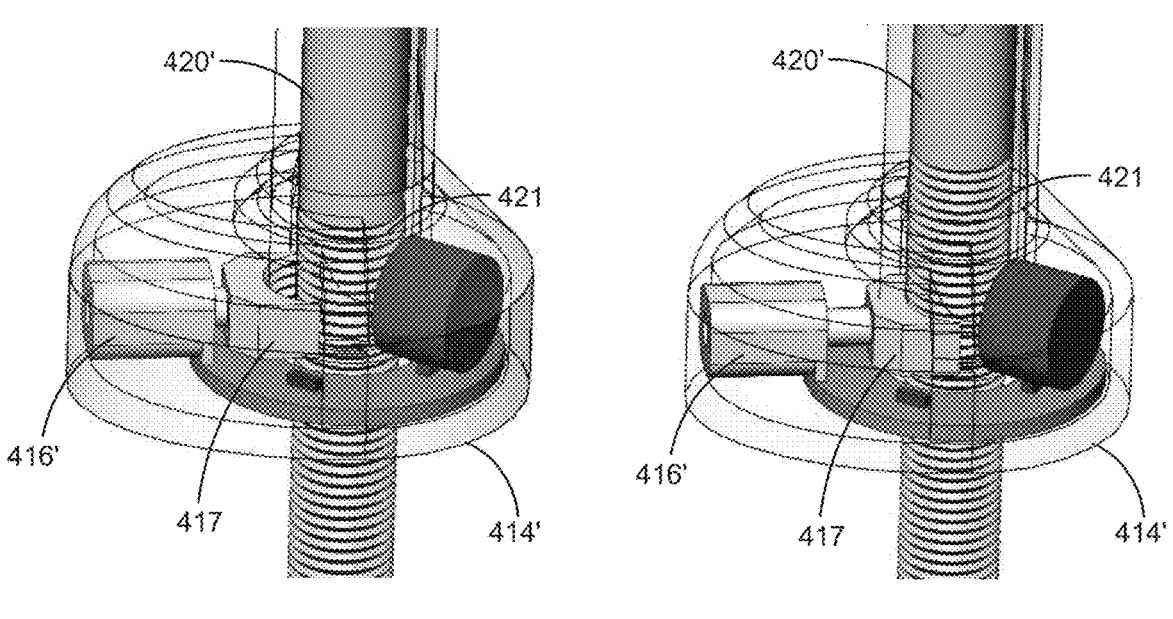
FIG. 18B illustrates the brake mechanism of the adapter of FIG. 18A in an unlocked state.
FIG. 18C illustrates the brake mechanism of the adapter of FIG. 18A in a locked state.

Referring now to FIGS. 18A to 18C, an alternative exemplary adapter is provided. Adapter 400' may be constructed similarly to adapter 400, with similar components having like-prime reference numerals. Unlike adapter 400, the outer surface of plunger 420' of adapter 400' may include first mating surface 421, e.g., a plurality of grooves, holes, or teeth, extending along at least a length of plunger 420', and braking mechanism 416' may include second mating surface 417, e.g., a fork, pin, or tooth, configured to be actuated to releasably engage with first mating surface 421 of plunger 420'. For example, braking mechanism 416' may comprise a linear actuator disposed orthogonal relative to plunger 420', such that second mating surface 417 may be actuated to transition between an unlocked state where second mating surface 417 is disengaged from plunger 420', as shown in FIG. 18B, and a locked state where second mating surface 417 is engaged with first mating surface 421 of plunger 420', as shown in FIG. 18C. In the locked state, the engagement between second mating surface 417 and first mating surface 421 arrests advancement of plunger 420' relative to sleeve 402'.

Figure 20:
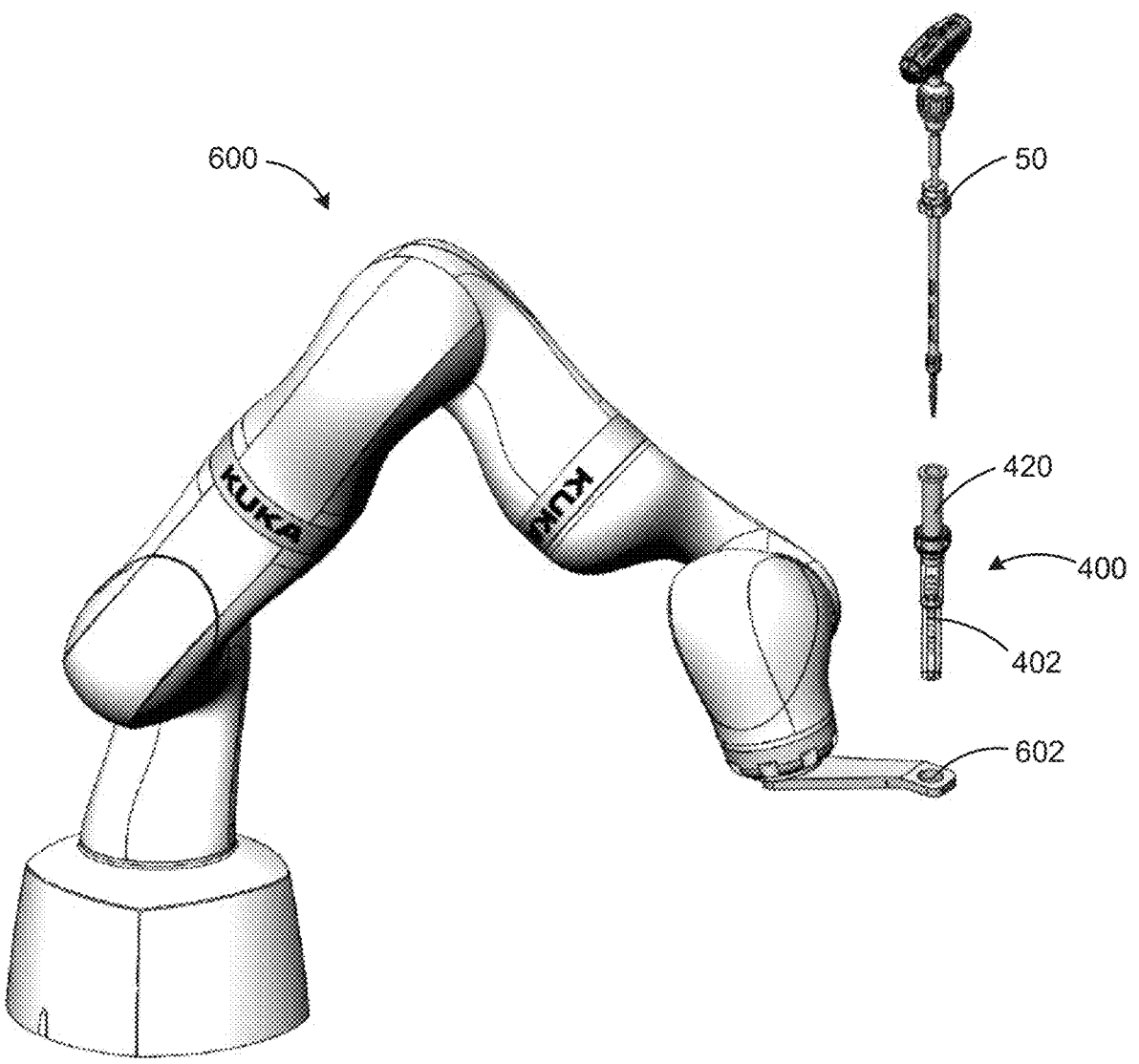
FIG. 20 illustrates the adapter integrated with a robot arm in accordance with the principles of the present disclosure.

Referring now to FIG. 20, in some alternative embodiments, adapter 400 may be integrated with robot arm 600 configured to automatically control and or position adapter 400 at the desired entry point of the anatomic structure. For example, robot arm 600 may be programmed to determine the entry point and/or trajectory of the surgical hand tool for a predetermined surgical procedure. Additionally or alternatively, robot arm 600 may be teleoperated via a master console operatively coupled to robot arm 600, such that robot arm 600 replicates movement at the master consoler. Robot arm 600 may be constructed, for example, as described in U.S. Pat. No. 11,344,372 and/or U.S. Patent Appl. No. 2022/0361896 to Bette, the entire contents of each of which are incorporated herein by reference. Additionally or alternatively, robot arm 600 may be another robot arm constructed in a manner within the ordinary skill in the art. As shown in FIG. 20, a distal end of robot arm 600 may include engagement portion 602 configured to be coupled to adapter 400. For example, adapter 400 may be integrated with, embedded in, or removably coupled to engagement portion 602. Accordingly, a surgical hand tool, e.g., surgical hand tool 50, may be inserted within adapter 400 as described above, such that adapter 400 may auto-lock the surgical hand tool relative to adapter 400 upon detection of a breach in accordance with the principles of the present disclosure described herein.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for use with a surgical drill, the system comprising:
a sensing drill bit comprising:
a proximal portion configured to be removably coupled to and receive rotary motion from the surgical drill; and
an elongated drilling portion having a distal end configured to penetrate an anatomic portion, the elongated drilling portion configured to sense electrical conductivity;
an adapter having a lumen sized and shaped to receive the elongated drilling portion of the sensing drill bit, the adapter comprising:
a stationary component comprising a spring;
a plunger coupled to the spring and configured to be slidably movable within the stationary component, the lumen extending through the plunger and the stationary component; and
a brake mechanism configured to be actuated to lock the plunger relative to the stationary component to thereby arrest advancement of the elongated drilling portion relative to the adapter; and
a controller operatively coupled to the elongated drilling portion and the brake mechanism, the controller programmed to:
receive a signal indicative of the electrical conductivity sensed by the elongated drilling portion as the elongated drilling portion penetrates the anatomic portion; and
responsive to the signal, cause the brake mechanism to arrest advancement of the elongated drilling portion and the surgical drill relative to the adapter.

2. The system of claim 1, wherein the sensing drill bit comprises a hub configured to house electronic components electrically coupled to the elongated drilling portion, the electronic components configured to generate and transmit the signal indicative of the electrical conductivity to the controller.

3. The system of claim 1, wherein the controller is configured to sense changes in electrical conductivity caused by the elongated drilling portion transitioning from a first tissue or fluid type to a second tissue or fluid type.

4. The system of claim 1, wherein the elongated drilling portion comprises at least two electrodes configured to sense electrical conductivity and to generate the signal indicative of the electrical conductivity sensed by the elongated drilling portion.

5. The system of claim 1, wherein the controller is further configured to:
detect a predetermined condition associated with a change of measured electrical conductivity based on the signal; and cause the brake mechanism to arrest advancement of the elongated drilling portion and responsive to detection of the predetermined condition.

6. The system of claim 1, wherein the controller is configured to generate an alarm upon detection of the signal satisfying a predetermined condition.

7. The system of claim 1, wherein a proximal end of the plunger comprises an abutment portion configured to engage with a hub of the sensing drill bit, such that the sensing drill bit applies the force to the plunger via the engagement between the abutment portion and the hub.

8. The system of claim 1, wherein an outer surface of the plunger comprises a first mating surface, and wherein the brake mechanism comprises a second mating surface configured to transition between an unlocked state where the second mating surface is disengaged from the plunger, and a locked state where the second mating surface releasably engages with the first mating surface of the plunger to thereby lock the plunger relative to the stationary component.

9. The system of claim 1, further comprising:
a sensor configured to measure an angle of the system relative to a surface of the anatomic portion in 3D space,
wherein the controller is configured to:
receive a signal indicative of the measured angle from the sensor; and
cause a display operatively coupled to the controller to display information indicative of the measured angle.

10. The system of claim 9, wherein the controller is configured to cause the display to display a virtual representation of the measured angle overlaid on a virtual model of the anatomic portion in real time.

11. The system of claim 9, wherein the sensor comprises at least one of a gravity angle sensor chip, an accelerometer, a compass, or gyroscope.

12. The system of claim 9, wherein the sensor is disposed on at least one of the adapter, the sensing drill bit, or the surgical drill.

13. The system of claim 9, wherein the controller is configured to, during a calibration phase, set a reference orientation of the system when the system is positioned vertically against the anatomic portion while a reference axis of the system points in a cephalic direction.

14. The system of claim 1, further comprising:
a sensor configured to measure a penetration depth of the elongated drilling portion within the anatomic portion,
wherein the controller is configured to:
receive a signal indicative of the penetration depth of the elongated drilling portion from the sensor; and
cause the brake mechanism to arrest advancement of the elongated drilling portion when changes in at least one of electrical conductivity, depth of penetration of the elongated drilling portion, or electrical conductivity as a function of depth of penetration satisfy one or more predetermined conditions.

15. The system of claim 14, wherein the controller is configured to cause a display operatively coupled to the controller to display information indicative of at least one of the electrical conductivity sensed by the elongated drilling portion or the penetration depth of the elongated drilling portion.

16. The system of claim 1, further comprising:
an external computing device operatively coupled to the adapter and the sensing drill bit via a wired or wireless connection, wherein the controller is disposed within the external computing device.

17. A system for use with a surgical drill, the system comprising:
a sensing drill bit comprising:
a proximal portion configured to be removably coupled to and receive rotary motion from the surgical drill; and
an elongated drilling portion having a distal end configured to penetrate an anatomic portion, the elongated drilling portion configured to sense electrical conductivity;
an adapter having a lumen sized and shaped to receive the elongated drilling portion of the sensing drill bit, the adapter comprising a brake mechanism configured to be actuated to arrest advancement of the elongated drilling portion relative to the adapter; and
a controller operatively coupled to the elongated drilling portion and the brake mechanism, the controller programmed to:
receive a signal indicative of the electrical conductivity sensed by the elongated drilling portion as the elongated drilling portion penetrates the anatomic portion; and
responsive to the signal, cause the brake mechanism to arrest advancement of the elongated drilling portion and the surgical drill relative to the adapter,
wherein the sensing drill bit comprises a hub configured to house electronic components electrically coupled to the elongated drilling portion, the electronic components configured to generate and transmit the signal indicative of the electrical conductivity to the controller, and
wherein the hub comprises one or more indicators configured to illuminate in one or more colors in a manner to indicate one or more predetermined ranges of electrical conductivity sensed by the elongated drilling portion, and wherein the controller is configured to cause the one or more indicators to illuminate in the one or more colors based on the signal indicative of the electrical conductivity sensed by the elongated drilling portion.

18. The system of claim 17, wherein the one or more indicators are configured to illuminate in a plurality of colors, each color of the plurality of colors indicative of a predetermined range of electrical conductivity sensed by the elongated drilling portion, and wherein the controller is configured to cause the one or more indicators to illuminate in a color of the plurality of colors based on the signal indicative of the electrical conductivity sensed by the elongated drilling portion.

19. The system of claim 17, wherein the one or more indicators are configured to illuminate in a plurality of intensities, each intensity of the plurality of intensities indicative of a predetermined range of electrical conductivity sensed by the elongated drilling portion, and wherein the controller is configured to cause the one or more indicators to illuminate in an intensity of the plurality of intensities based on the signal indicative of the electrical conductivity sensed by the elongated drilling portion.

20. The system of claim 17, wherein the one or more indicators are configured to illuminate in a blinking manner, and wherein the controller is configured to cause the one or more indicators to illuminate in the blinking manner with at least one of a pitch or cadence based on the signal indicative of the electrical conductivity sensed by the elongated drilling portion.

21. The system of claim 17, wherein the one or more indicators comprise one or more ring-shaped indicators.

22. The system of claim 17, wherein the adapter comprises:

a stationary component comprising a spring;

a plunger coupled to the spring, the plunger configured to be slidably movable within the stationary component responsive to a force applied by the sensing drill bit, wherein the lumen extends through the plunger and the stationary component, and wherein the brake mechanism is configured to lock the plunger relative to the stationary component to thereby arrest advancement of the elongated drilling portion relative to the adapter.

23. A computer implemented system for operating an adapter for use with a sensing drill bit comprising an elongated drilling portion configured to receive rotary motion from a surgical drill, the system comprising at least one processor configured to:

receive a signal indicative of the electrical conductivity sensed by the elongated drilling portion as the elongated drilling portion penetrates an anatomic portion through a lumen of a sleeve of the adapter via the surgical drill;

detect a predetermined condition associated with a change of measured electrical conductivity based on the signal;

cause a brake mechanism of the adapter to arrest advancement of the elongated drilling portion and the surgical drill relative to the adapter responsive to detection of the predetermined condition; and cause one or more indicators of the sensing drill bit to illuminate in a color of a plurality of colors or an intensity of a plurality of intensities based on the signal indicative of the electrical conductivity sensed by the elongated drilling portion, each color of the plurality of colors or each intensity of the plurality of intensities indicative of a predetermined range of electrical conductivity sensed by the elongated drilling portion.

24. The computer implemented system of claim 23, wherein the at least one processor is configured to:

detect a predetermined condition associated with a change of measured electrical conductivity based on the signal; and generate an alert when changes in electrical conductivity satisfy one or more predetermined conditions.

25. The computer implemented system of claim 23, wherein the at least one processor is configured to:

receive, from one or more sensors, a signal indicative of an angle of the adapter relative to a surface of the anatomic portion in 3D space as the elongated drilling portion penetrates the anatomic portion; and cause a display operatively coupled to the at least one processor to display information indicative of the angle.

26. The computer implemented system of claim 25, wherein the at least one processor is configured to cause the display to display a virtual representation of the angle overlaid on a virtual model of the anatomic portion in real time.

27. The computer implemented system of claim 23, wherein the at least one processor is configured to:

receive, from one or more depth sensors, a signal indicative of a depth of penetration of the elongated drilling portion within the anatomic portion; and cause the brake mechanism to arrest advancement of the elongated drilling portion when changes in at least one of electrical conductivity, depth of penetration of the elongated drilling portion, or electrical conductivity as a function of depth of penetration satisfy one or more predetermined conditions.

28. The computer implemented system of claim 23, wherein the at least one processor is configured to cause, responsive to detection of the predetermined condition, a first mating surface of the brake mechanism to transition from an unlocked state where the first mating surface is disengaged from a plunger of the adapter, to a locked state where the first mating surface releasably engages with a second mating surface disposed on an outer surface of the plunger to thereby lock the plunger relative to a stationary component of the adapter and arrest advancement of the elongated drilling portion and the surgical drill relative to the adapter.

29. A computer implemented system for operating an adapter for use with a sensing drill bit comprising an elongated drilling portion configured to receive rotary motion from a surgical drill, the system comprising at least one processor configured to:

receive a signal indicative of the electrical conductivity sensed by the elongated drilling portion as the elongated drilling portion penetrates an anatomic portion through a lumen of a sleeve of the adapter via the surgical drill;

detect a predetermined condition associated with a change of measured electrical conductivity based on the signal;

cause a brake mechanism of the adapter to arrest advancement of the elongated drilling portion and the surgical drill relative to the adapter responsive to detection of the predetermined condition; and cause one or more indicators of the sensing drill bit to illuminate in a blinking manner with at least one of a pitch or cadence indicative of a predetermined range of electrical conductivity sensed by the elongated drilling portion.

* * * * *